United States Patent [19]
Binger et al.

[11] Patent Number: 6,008,342
[45] Date of Patent: Dec. 28, 1999

[54] DNA ENCODING EIMERIA ANTIGEN

[75] Inventors: Mary-Helen Binger, Hopewell, N.J.; Luis Pasamontes, Trimbach, Switzerland

[73] Assignee: Roche Vitamins Inc., Parsippany, N.J.

[21] Appl. No.: 08/770,035

[22] Filed: Dec. 19, 1996

Related U.S. Application Data

[62] Division of application No. 08/257,392, Jun. 9, 1994, Pat. No. 5,688,513, which is a division of application No. 07/729,099, Jul. 12, 1991, Pat. No. 5,403,581.

[51] Int. Cl.$^6$ .................. C07H 21/04; A61K 39/012; C12P 21/04; C12N 1/20
[52] U.S. Cl. .................. 536/23.7; 424/271.1; 435/69.3; 435/71.1; 435/252.3; 435/252.33; 435/320.1; 536/22.1
[58] Field of Search ................... 536/22.1, 23.7; 435/69.1, 69.3, 71.1, 320.1, 252.3, 252.33; 424/271.1

[56] References Cited

U.S. PATENT DOCUMENTS

| | | | |
|---|---|---|---|
| 4,639,372 | 1/1987 | Murray et al. | 424/88 |
| 4,650,676 | 3/1987 | Schenkel et al. | 424/88 |
| 4,710,377 | 12/1987 | Schenkel et al. | 424/88 |
| 4,808,404 | 2/1989 | Bhogal | 424/88 |
| 4,874,705 | 10/1989 | Andrews et al. | 435/252.33 |
| 5,001,230 | 3/1991 | Brown et al. | 536/7 |
| 5,122,471 | 6/1992 | Jenkins et al. | 435/252.3 |
| 5,187,080 | 2/1993 | Andrews et al. | 435/69.3 |

FOREIGN PATENT DOCUMENTS

| | | | |
|---|---|---|---|
| 1204057 | 5/1986 | Canada | A61K 39/012 |
| 135 073 | 3/1985 | European Pat. Off. | C12P 21/00 |
| 135 712 | 4/1985 | European Pat. Off. | C12P 21/00 |
| 164 176 | 12/1985 | European Pat. Off. | A61K 39/012 |
| 167 443 | 1/1986 | European Pat. Off. | A61K 39/012 |
| 0291173 | 4/1987 | European Pat. Off. | . |
| 223 710 | 5/1987 | European Pat. Off. | A61K 39/012 |
| 231 537 | 8/1987 | European Pat. Off. | C12N 15/00 |
| 241 139 | 10/1987 | European Pat. Off. | C12N 15/00 |
| 256 536 | 2/1988 | European Pat. Off. | A61K 39/012 |
| 324 647 | 7/1989 | European Pat. Off. | C15N 15/00 |
| 337 589 | 10/1989 | European Pat. Off. | C12N 15/00 |
| 344 808 | 12/1989 | European Pat. Off. | C12N 15/00 |
| 349 071 | 1/1990 | European Pat. Off. | C12N 15/30 |
| 390 267 A1 | 10/1990 | European Pat. Off. | A61K 39/012 |
| 439 056 | 7/1991 | European Pat. Off. | C07K 13/00 |
| 519 547 | 12/1992 | European Pat. Off. | C12N 15/30 |
| 86/00528 | 1/1986 | WIPO | A61K 39/02 |
| 137 512 | 5/1987 | WIPO | . |
| 88/06629 | 9/1988 | WIPO | C12P 21/00 |
| 89/07650 | 8/1989 | WIPO | C12P 21/00 |

OTHER PUBLICATIONS

Houghten et al Vaccines 86, pp. 21–25, 1986.
Perkus et al., Science 229:981 (1985).
Smith et al., Gene 25:21 (1983).
Zemcik et al., Immunol. Methods 91:265 (1986).
Moss et al., Ann. Rev. Immunol. 5:305 (1987).
Mockett and Rose, Parasite Immunol. 8:481–489 (1986).
Crane et al., Parasite Immunol. 8:467–480 (1986).
Tomley et al., Coccidia and Intestinal coccidiomorphs, Vth International Conference, Tours (France) Oct. 1989, Ed. INRA Publ. pp. 569–573.
Mackett et al., DNA cloning, vol. II, ed. by Glover, Cancer Research Campaign, Eukaryotic Mol. Genetics Res. Group, Dept. of Biochem., Imperial College of Science and Technology, London (1985) Chapter 7, pp. 191–211.
Good et al., Science 235:1059–1062 (1987).
Danforth et al., Poultry Sci. 67 (Suppl. 1) Ann. Mtg. 75th Poultry Sci. Assn. abstract (1986) p. 30.
Jenkins and Dame, Fed. Proc. 46(3) abstract 2696 (1987) p. 778.
Thammana and Amran, Fed. Proc. 45(4) abstract 4083 (1986) p. 857.

(List continued on next page.)

*Primary Examiner*—James C. Housel
*Assistant Examiner*—Ja-Na Hines
*Attorney, Agent, or Firm*—George W. Johnston; William H. Epstein; Briana C. Buchholz

[57] ABSTRACT

The invention provides an immunogenic polypeptide having the amino acid sequence

```
M A K S M L S G I V F A G L V A A A A
S S A N S A A N V S V L E S G P A V Q E
V P A R T V T A R L A K P L L L L S A L
A A T L A A A F L V L Q C F N I I S S N
N Q Q T S V R R L A A G G A C G D E E D
A D E G T S Q Q A S R R R R K P D T P A
A D K Y D F V G G T P V S V T E P N V D
E V L I Q I R N K Q I F L K N P W T G Q
E E Q V L V L E R Q S E E P I L I V A R
T R Q T L E G Y L G S Q A L A Q D G K T
A K E E K V E G G K T H R R Y K V K S S
D P G Y G F P Y T T V L D G V P V G T D
E D G Y V V E V L M K T G P H G G V D M
M T S T A S Q G K F C G V L M D D G K G
N L V D G Q G R K I T A V I G M L T Q P
D T E F R S G P G D D E D D E (SEQ ID NO:1)
``` and fragments thereof,
which polypeptides are capable of inducing an immune response against Eimeria parasites, and the DNA encoding such polypeptides, as well as recombinant vectors and recombinant viruses containing the said DNA or fragments thereof and transformed microorganisms containing such vectors and viruses and coccidiosis vaccines comprising such polypeptides.

6 Claims, 50 Drawing Sheets

OTHER PUBLICATIONS

Wisher, J. Cell. Biochem. 7 (Suppl.) 12th Ann. Mtg. UCLA abstract 0059 (1983) p. 25.
Clarke et al., J. Cell. 10 (Suppl.) 15th Ann. Mtg. UCLA abstract C87 (1986) p. 145.
Bhogal et al., Infection and Immunity 56:1113–1119 (1988).
Clarke et al., Molecular Strategies of Parasitic Invasion, ed. Agabian et al. (Alan R. Liss, Inc. 1987) pp. 701–711.
Clarke et al., Mol. and Biochem. Para. 22:79–87 (1987).
Jenkins et al., Mol. and Biochem. Para. 32:153–162 (1989).
Jenkins et al., 77th Ann. Mtg. Poultry Sci. Assn. 67(1) abstract (1988) p. 100.
Kim et al., 77th Ann. Mtg. Poultry Sci. Assn. 67(1) abstract (1988) p. 103.
Lillehoj et al., 77th Ann. Mtg. Poultry Sci. Assn. 67(1) abstract (1988) p. 111.
Augustine and Danforth, Molecular Strategies of Parasitic Invasion, ed. Agabian et al. (Alan R. Liss, Inc. 1987) pp. 511–520.
Murray et al., Proc. of the Georgia Coccidiosis Conf., ed. by McDougald et al. (Nov. 1985) pp. 564–573.
Augustine, Proc. of the Georgia Coccidiosis Conf., ed. by McDougald et al. Nov. 1985) pp. 602–608.
Wong and Thammana, Proc. of the Georgia Coccidiosis Conf., ed. by McDougald et al. (Nov. 1985) pp. 591–601.
Danforth, Proc. of the Georgia Coccidiosis Conf., ed. by McDougald et al. (Nov. 1985) pp. 574–590.
Lillehoj, Proc. of the Georgia Coccidiosis Conf., ed. by McDougald et al. (Nov. 1985) pp. 470–481.
Files et al., Molecular Strategies of Parasitic Invasion, ed. Agabian et al. (Alan R. Liss, Inc. 1987) pp. 713–723.
Liberator et al., Nucleic Acids Res. 17:7104 (1989).
Binger et al., J. Cell. Biochem. (Suppl.) 15th Ann. Mtg. UCLA abstract C83 (1986) p. 144.
Paul et al., J. Cell. Biochem. (Suppl.) 15th Ann. Mtg. UCLA abstract C157 (1986) p. 169.
McAndrew et al., J. Cell. Biochem. (Suppl.) 15th Ann. Mtg. UCLA abstract C97 (1986) p. 149.
Files et al., J. Cell. Biochem. (Suppl.) 15th Ann. Mtg. UCLA abstract C92 (1986) p. 147.
Danforth et al., Fed. Proc. 44(4) abstract 5398 (1985) p. 1334.
Brothers et al., Mol. and Biochem. Parasitol. 28:235–248 (1988).
Bianco et al., Proc. Natl. Acad. Sci. USA 83:8713–8717 (1986).
McDonald et al., Parasitology 93:1–7 (1986).
Danforth and Augustine, 77th Ann. Mtg. Poultry Sci. Assn. 67(1) abstract (1988) p. 72.
Jenkins et al., 77th Ann. Mtg. Poultry Sci. Assn. 67(1) abstract (1988) p. 100.
Clare and Danforth, 77th Ann. Mtg. Poultry Sci. Assn. 67(1) abstract (1988) p. 68.
Hyun et al., Vet. Imm. & Immunopath., 13:321–330 (1986).
Davidson et al., J. of Gen. Vir. 67:1759–1816 (1986).
Kobayashi et al., The J. of Biol. Chem., 264:18247–18259 (1989).
Shuster, Nucleic Acid Res., Jul. 20, 1990.

```
                                                                          60
GCTTTTGCGTCGGAGATAGTCGTTGCGTGTTGCCGATCACCCGCGAACTTCTCTACCA
|----+----|----+----|----+----|----+----|----+----|----+----|
CGAAAACGCAGCCTCTATCAGCAACACACAAACGCGTAGTGGGCGCTTGAAGAGATGGT

120
ACTGAAAATGGCTAAGTCTATGCTTTCTGGAATTGTTTTTGCTGGTCTTGTTGCTGCTGC
|----+----|----+----|----+----|----+----|----+----|----+----|
TGACTTTTACCGATTCAGATACGAAAGACCTTAACAAAAACGACCAGAACAACGACGACG
          M   A   K   S   M   L   S   G   I   V   F   A   G   L   V   A   A   A

180
AGCGGGCCAGTTCGGCCAACGCCGCCAACGTCTCCGTTTTGGAGAGTGGCCCCGCTGT
|----+----|----+----|----+----|----+----|----+----|----+----|
TCGCCCGGTCAAGCCGGTTGCGGCGGTTGCAGGAGGCAAACCTCTCACCCGGGCGACA
  A   S   S   A   A   N   S   A   A   N   V   S   V   L   E   S   G   P   A   V

240
GCAGGAAGTGCCAGCGCGCACGGTCACAGCTCGCCTGGCGAGCCTTTGCTGCTTCTTTC
|----+----|----+----|----+----|----+----|----+----|----+----|
CGTCCTTCACGGTCGCGCGTGCCAGTGTCGAGCGGACTCGGAAACGACGAAGAAAG
  Q   E   V   P   A   R   T   V   T   A   R   L   A   K   P   L   L   L   S
```

FIG. 1a

```
TGCTCTTGCTGCTGGACTTTGGCAGCAGCTTTCCTCGTTTTGCAATGCTTCAACATCATCTC
     ---------+---------+---------+---------+---------+---------+  300
ACGAGAACGACGACCTGAAACCGTCGTCGAAAGGAGCAAAACGTTACGAAGTTGTAGTAGAG
  A  L  A  A  T  L  A  A  A  F  L  V  L  Q  C  F  N  I  I  S

CAGCAACAACCAGCAAACCAGCGTCAGGAGACTGCCGCCGGAGGTGCAGCGGAGATGA
     ---------+---------+---------+---------+---------+---------+  360
GTCGTTGTTGGTCGTTTGGTCGCAGTCCTCTGACGGCGGCCTCCACGTCGCCTCTACT
  S  N  N  Q  Q  T  S  V  R  R  L  A  A  G  G  A  C  G  D  E

GGAAGATGCAGATGAGGGAACTTCACAGCAGGCCAGCCGGGAGGAGAAAACCTGATAC
     ---------+---------+---------+---------+---------+---------+  420
CCTTCTACGTCTACTCCCTTGAAGTGTCGTCCGGTCGGCCCTCCTCTTTTGGACTATG
  E  D  A  D  E  G  T  S  Q  Q  A  S  R  R  R  R  K  P  D  T

CCCTGCAGCAGATAAATACGATTTTGTGGCGGAACTCCAGTTTCGGTCACTGAGCCCAA
     ---------+---------+---------+---------+---------+---------+  480
GGGACGTCGTCTATTTATGCTAAAACACCGCCTTGAGGTCAAAGCCAGTGACTCGGGTT
  P  A  A  D  K  Y  D  F  V  G  G  T  P  V  S  V  T  E  P  N

TGTTGATGAAGTCCTTATCCAAATTAGAAATAAACAAATCTTTTGAAGAACCCATGGAC
     ---------+---------+---------+---------+---------+---------+  540
ACAACTACTTCAGGAATAGGTTTAATCTTTATTGTTTAGAAAACTTCTTGGGTACCTG
  V  D  E  V  L  I  Q  I  R  N  K  Q  I  F  L  K  N  P  W  T
```

FIG. 1b

```
                                                                    600
TGGACAAGAAGAACAAGTTCTAGTACTGGACGACAAAGTGAAGAACCCATTCTGATTGT
ACCTGTTCTTCTTGTTCAAGATCATGACCTGCTGTTTCACTTCTTGGGTAAGACTAACA
 G  Q  E  E  Q  V  L  V  L  E  R  Q  S  E  E  P  I  L  I  V
                                                                    660
GGCGAGGACAAGACAAACACTTGAAGGATATCTTGGTAGTCAAGCTCTTGCACAGGACGG
CCGCTCCTGTTCTGTTTGTGAACTTCCTATAGAACCATCAGTTCGAGAACGTGTCCTGCC
 A  R  T  R  Q  T  L  E  G  Y  L  G  S  Q  A  L  A  Q  D  G
                                                                    720
AAAGACTGCTAAAGAAGAGAAAGTTGAAGGAGGCAAAACTCACAGAAGATATAAAGTCAA
TTTCTGACGATTTCTTCTCTTTCAACTTCCTCCGTTTTGAGTGTCTTCTATATTTCAGTT
 K  T  A  K  E  E  K  V  E  G  G  K  T  H  R  R  Y  K  V  K
                                                                    780
GAGCAGGCGACCAGGATATGGATTCCCATACACACCGGTTCCTGACGGGGTTCCTGTGGG
CTCGTCGCTGGTCCTATACCTAAGGGTATGTGTGGCCAAGGACTGCCCCAAGGACACCC
 S  S  D  P  G  Y  G  F  P  Y  T  T  V  L  D  G  V  P  V  G
```

FIG. 1c

```
AACAGACGAAGACGGATACGTCGTCGAAGTTCTTATGAAAACCGGACCCCATGGAGGAGT
    ----+----|----+----|----+----|----+----|----+----|----+----|   840
TTGTCTGCTTCTGCCTATGCAGCAGCTTCAAGAATACTTTTGGCCTGGGGTACCTCCTCA

T  D  E  D  G  Y  V  V  E  V  L  M  K  T  G  P  H  G  G  V

CGACATGATGACTAGCACACAAGGAAAATTCTGCGGAGTGCTTATGGATGACGG
    ----+----|----+----|----+----|----+----|----+----|----+----|   900
GCTGTACTACTGATCGTGTCGTAGTTCCTTTTAAGACGCCTCACGAATACCTACTGCC

D  M  M  T  S  T  A  S  Q  G  K  F  C  G  V  L  M  D  D  G

AAAAGGAAACCTAGTCGATGGACAAGGAGAAAAATTACCGCCGTTATCGGCATGCTAAC
    ----+----|----+----|----+----|----+----|----+----|----+----|   960
TTTTCCTTTGGATCAGCTACCTGTTCCCTCTTTTTAATGGCGGCAATAGCCGTACGATTG

K  G  N  L  V  D  G  Q  G  R  K  I  T  A  V  I  G  M  L  T

CAACCGGATACCGAGTTTAGAAGCGGAGTCAAATCTTCGCCTGGTCCTCTGCTCCTCACTC
    ----+----|----+----|----+----|----+----|----+----|----+----|   1020
AGTTGGCCTATGGCTCAAATCTTCGCCTCAGTTTAGAAGCGGACGAGGACGACGAGTGAGTGAG

Q  P  D  T  E  F  R  S  G  P  G  D  D  E  D  D  E  -

CGGAGTTGGCTTTGTCCCTGTTGATGCCGTTGCCCACTTTCGCAGCTTGCTTGTTCCT
    ----+----|----+----|----+----|----+----|----+----|----+----|   1080
GCCTCAACCGAAAACAGGGACAACTACGGCAACGGGTGAAAGCGTCGAACGAACAAAGGA
```

FIG. 1d

```
GGGCCTTGCCTGTGTGCCGCGACATGCCGCTTGGCGTTCCGCCTGAGTTCTTTCGGACTGTTT
   |----|----|----|----|----|----|----|----|----|----|----|----|
GCCCTCAACCGAAACACAGGGACAACTACGGCAACGGGTGAAAGCGTCGAACAAGGA         1140

AACTTTTAATTCATTTTCTACTGCGGCAAAAAAAAAAAAAAAAAAAAAA
   |----|----|----|----|----|----|----|----|----|
TTGAAAATTAAGTAAAAGATGACGCCGTTTTTTTTTTTTTTTTTTTTTT                 1197
```

FIG. 1e

```
     XhoI
  1  CTCGAGAAAT  CATAAAAAAT  TTATTGCTT   TGTGAGCGGA  TAACAATTAT

EcoRI
 51  AATAGATTCA  ATTGTGAGCG  GATAACAATT  TCACACAGAA  TTCATTAAAG

BamHI  SalI            PstI       HindIII
101  AGGAGAAATT  AACTATGAGA  GGATCCGTCG  ACCTGCAGCC  AAGCTTAATT
                 MetArg      GlySerValA  spLeuGlnPr  oSerLeuIle 151  AGCTGAGCTT  GGACTCCTGT  TGATAGATCC  AGTAATGACC  TCAGAACTCC
     Ser

201  ATCTGGATTT  GTTCAGAACG  CTCGGTTGCC  GCCGGGGCGTT TTTTATTGGT

251  GAGAATCCAA  GCTAGCTTGG  CGAGATTTTC  AGGAGCTAAG  GAAGCTAAAA

301  TGGAGAAAAA  AATCACTGGA  TATACCACCG  TTGATATATC  CCAATGGCAT

351  CGTAAAGAAC  ATTTTGAGGC  ATTTCAGTCA  GTTGCTCAAT  GTACCTATAA

401  CCAGACCGTT  CAGCTGGATA  TTACGGCCTT  TTTAAAGACC  GTAAAGAAAA

451  ATAAGCACAA  GTTTTATCCG  GCCTTTATTC  ACATTCTTGC  CCGCCTGATG

501  AATGCTCATC  CGGAATTTCG  TATGGCAATG  AAAGACGGTG  AGCTGGTGAT

551  ATGGGATAGT  GTTCACCCTT  GTTACACCGT  TTTCCATGAG  CAAACTGAAA

FIG. 5a
```

```
601  CGTTTTCATC GCTCTGGAGT GAATACCACG ACGATTTCCG GCAGTTTCTA
651  CACATATATT CGCAAGATGT GGCGTGTTAC GGTGAAAACC TGGCCTATTT
701  CCCTAAAGGG TTTATTGAGA ATATGTTTTT CGTCTCAGCC AATCCCTGGG
751  TGAGTTTCAC CAGTTTTTGAT TTAAACGTGG CCAATATGGA CAACTTCTTC
801  GCCCCCGTT  TCACCATGGG CAAATATTAT AGCCAAGGCG ACAAGGTGCT
851  GATGCCGCTG GCGATTCAGG TTCATCATGC CGTCTGTGAT GGCTTCCATG
901  TCGGCAGAAT GCTTAATGAA TTACAACAGT ACTGCGATGA GTGGCAGGGC
951  GGGGCGTAAT TTTTTTAAGG CAGTTATTGG TGCCCTTAAA CGCCTGGGGT
1001 AATGACTCTC TAGCTTGAGG CATCAAATAA AACGAAAGGC TCAGTCGAAA
1051 GACTGGGCCT TTCGTTTTAT CTGTTGTTTG TCGGTGAACG CTCTCCTGAG
          Xbal
1101 TAGGACAAAT CCGCCGCTCT AGAGCTGCCT CGCGCCGTTC GGTGATGACG
```

FIG. 5b

```
1151  GTGAAAACCT  CTGACACATG  CAGCTCCCGG  AGACGGTCAC  AGCTTGTCTG
1201  TAAGCGGATG  CCGGGAGCAG  ACAAGCCCGT  CAGGGCCGCGT CAGCGGGTGT
1251  TGGCGGGTGT  CGGGGCGCAG  CCATGACCCA  GTCACGTAGC  GTAAGCGGAG
1301  TGTATACTGG  CTTAACTATG  CGGCATCAGA  GCAGATTGTA  CTGAGAGTGC
1351  ACCATATGCG  GTGTGAAATA  CCGCACAGAT  GCGTAAGGAG  AAAATACCGC
1401  ATCAGGCGCT  CTTCCGCTTC  CTCGCTCACT  GACTCGCTGC  GCTCGGTCTG
1451  TCGGCTGCGG  CGAGCGGTAT  CAGCTCACTC  AAAGGCGGTA  ATACGGTTAT
1501  CCACAGAATC  AGGGGATAAC  GCAGGAAAGA  ACATGTGAGC  AAAAGGCCAG
1551  CAAAAGGCCA  GGAACCCTAA  AAAGGCCCGCG TTGCTGGCGT  TTTTCCATAG
1601  GCTCCGCCCC  CCTGACGAGC  ATCACAAAAA  TCGACGCTCA  ATGCAGAGGT
1651  GGCGAAACCC  GACAGGACTA  TAAAGATACC  AGGCGTTTCC  CCCTGGAAGC
1701  TCCCTCGTGC  GCTCTCCTGC  TCCGACCCTG  CCGCTTACG  GATACCTGTC
1751  CGCCTTTCTC  CCTTCGGGAA  GCGTGGCGCT  TTCTCAATGC  TCACGCTGTA
```

FIG. 5c

```
1801  GGTATCTCAG  TTCGGTGTAG  GTCGTTCGCT  CCAAGCTGGG  CTGTGTGCAC
1851  GAACCCCCCG  TTCAGCCCGA  CCGCTGCGCC  TTATCCGGTA  ACTATCGTCT
1901  TGAGTCCAAC  CCGGTAAGAC  ACGACTTATC  CGCACTGGCA  GCAGCCACTG
1951  GTAACAGGAT  TAGCAGAGCG  AGGTATGTAG  GCGGTGCTAC  AGAGTTCTTG
2001  AAGTGGTGGC  CTAACTACGG  CTACACTAGA  AGGACAGTAT  TTGGTATCTG
2051  CGCTCTGCTG  AAGCCAGTTA  CCTTCGGAAA  AAGAGTTGGT  AGCTCTTGAT
2101  CCGGCAAACA  AACCACCGCT  GGTAGCGGTG  GTTTTTTGT   TTGCAAGCAG
2151  CAGATTACGC  GCAGAAAAAA  AGGATCTCAA  GAAGATCCTT  TGATCTTTTC
2201  TACGGGGTCT  GACGCTCAGT  GGAACGAAAA  CTCACGTTAA  GGGATTTTGG
2251  TCATGAGATT  ATCAAAAAGG  ATCTTCACCT  AGATCCTTTT  AAATTAAAAA
2301  TGAAGTTTTA  AATCAATCATA AAGTATATAT  GAGTAAACTT  GGTCTGACAG
2351  TTACCAATGC  TTAATCAGTG  AGGCACCTAT  CTCAGCGATC  TGTCTATTTC
2401  GTTCATCCAT  AGTTGCCTGA  CTCCCCGTCG  TGTAGATAAC  TACGATACGG
2451  GAGGGCTTAC  CATCTGGCCC  CAGTGCTGCA  ATGATACCGC  GAGACCCACG
```

FIG. 5d

```
2501  CTCACCGGCT  CCAGATTTAT  CAGCAATAAA  CCAGCCAGCC  GGAAGGGCCG
2551  AGGCAGAAG   TGGTCCTGCA  ACTTTATCCG  CAGGGGCCGT  GTCTATTAAT
2601  TGTTGCCGGG  AAGCTAGAGT  AAGTAGTTTCG CCAGTTAATA  GTTTGCGCAA
2651  CGTTGTTGCC  ATTGCTACAG  GCATCGTGGT  GTCACGCTCG  TCGTTTGGTA
2701  TGGCTTCATT  CAGCTCCGGT  TCCCAACGAT  CAAGGCGAGT  TACATGATCC
2751  CCCATGTTGT  GCAAAAAAGC  GGTTAGCTCC  TTCGGTCCTC  CGATCGTTGT
2801  CAGAAGTAAG  TTGGCCGCAG  TGTTATCACT  CATGGTTATG  GCAGCACTGC
2851  ATAATTCTCT  TACTGTCATG  CCATCCGTAA  GATGCTTTTC  TGTGACTGGT
2901  GAGTACTCAA  CCAAGTCATT  CTGAGAATAG  TGTATGCGGC  GACCGATTTG
2951  CTCTTGCCCG  GCGTCAATAC  GGGATAATAC  CGCGCCACAT  AGCAGAACTT
3001  TAAAAGTGCT  CATCATTGGA  AAACGTTCTT  CGGGGCCAAA  ACTCTCAAGG
3051  ATCTTACCGC  TGGTGAGATC  CAGTTCGATG  TAACCCACTC  GTGAACCCAA
3101  CTGATCTTCA  GCATCTTTTA  CTTTCACCAG  CGTTTCTGGG  TGAGCAAAAA
3151  CAGGAAGGCA  AAATGCCGCA  AAAAAGGGAA  TAAGGGCGAC  ACGGAAATGT
3201  TGAATACTCA  TACTCTTCCT  TTTTCAATAT  TATTGAAGCA  TTTATCAGGG
3251  TTATTGTCTC  ATGAGCGGAT  ACATATTTGA  ATGTATTTGA  AAAATAAAC
3301  AAATAGGGGT  TCCGCGCACA  TTTCCCCGAA  AGTGCCACC   TGACGTCTAA
3351  GAAACCATTA  TTATCATGAC  ATTAACCTAT  AAAAATAGGC  GTATCACGAG
3401  GCCCTTTCGT  CTTCAC
```

FIG. 5e

```
      Xhol
    1 CTCGAGAAAT CATAAAAAAT ATTGTGAGCG TTATTTGCTT TGTGAGCGGA TAACAATTAT
                                                                 EcoRI
   51 AATAGATTCA                        GATAACAATT                TCATTAAAG
                                         BamHI  Sall              Hindlll
                                                     Pstl
  101 AGGAGAAATT AACTATGAGG GATCCGTCGA CCTGCAGCCA AGCTTAATTA
                    MetArg   AspProSerT hrCysSerGl nAla
  151 GCTGAGCTTG GACTCCTGTT GATAGATCCA GTAATGACCT CAGAACTCCA
  201 TCTGGGATTTG TTCAGAACGC TCGGTTGCCG CCGGGCGTTT TTTATTGGTG
  251 AGAATCCAAG CTAGCTTGGC GAGATTTTCA GGAGCTAAGG AAGCTAAAAT
  301 GGAGAAAAAA ATCACTGGAT ATACCACCGT TGATATATCC CAATGGCATC
  351 GTAAAGAACA TTTTGAGGCA TTTCAGTCAG TTGCTCAATG TACCTATAAC
  401 CAGACCGTTC AGCTGGATAT TACGGCCTTT TTAAAGACCG TAAAGAAAAA
  451 TAAGCACAAG TTTTATCCGG CCTTTATTCA CATTCTTGCC CGCCTGATGA
  501 ATGCTCATCC GGAATTTCGT ATGGCAATGA AAGACGGTGA GCTGGTGATA
  551 TGGGATAGTG TTCACCCCTTG TTACACCGTT TTCCATGAGC AAACTGAAAC
  601 GTTTTCATCG CTCTGGAGTG AATACCACGA CGATTTCCGG CAGTTTCTAC
```

FIG. 7a

```
651   ACATATATTC   GCAAGATGTG   GCGTGTACG    GTGAAAACCT   GGCCTATTTC
701   CCTAAAGGGT   TTATTGAGAA   TATGTTTTC    GTCTCAGCCA   ATCCCTGGGT
751   GAGTTTCACC   AGTTTTGATT   TAAACGTGGC   CAATATGGAC   AACTTCTTCG
801   CCCCCGTTTT   CACCATGGGC   AAATATTATA   CGCAAGGCGA   CAAGGTGCTG
851   ATGCCGCTGG   CGATTCAGGT   TCATCATGCC   GTCTGTGATG   GCTTCCATGT
901   CGGCAGAAATG  CTTAATGAAT   TACAACAGTA   CTGCGTGAG    TGGCAGGGCG
951   GGGGCGTAAT   TTTTTAAGGC   AGTTATTGGT   GCCCTTAAAC   GCCTGGGGTA
1001  ATGACTCTCT   AGCTTGAGGC   ATCAAATAAA   ACGAAAGGCT   CAGTCGAAAG
                  Xbal
1051  ACTGGGCCTT   TCGTTTTATC   TGTTGTTTGT   CGGTGAACGC   TCTCCTGAGT
1101  AGGACAAATC   CGCCGCTCTA   GAGCTGCCTC   GCGCGTTTCG   GTGATGACGG
```

FIG. 7b

```
1151  TGAAACCTC  TGACACATGC  AGCTCCCGGA  GACGGTCACA  GCTTGTCTGT
1201  AAGCGGATGC  CGGGAGCAGA  CAAGCCCGTC  AGGGCGCGTC  AGCGGGTGTT
1251  GGCGGGTGTC  GGGGCGCAGC  CATGACCCAG  TCACGTAGCG  ATAGCGGAGT
1301  GTATACTGGC  TTAACTATGC  GGCATCAGAG  CAGATTGTAC  TGAGAGTGCA
1351  CCATATGCGG  TGTGAAATAC  CGCACAGATG  CGTAAGGAGA  AAATACCGCA
1401  TCAGGCGCTC  TTCCGCTTCC  TCGCTCACTG  ACTCGCTGCG  CTCGGTCTGT
1451  CGGCTGCGGC  GAGCGGTATC  AGCTCACTCA  AAGGCGGTAA  TACGGTTATC
1501  CACAGGAATC  GGGGATAACG  CAGGAAAGAA  CATGTGAGCA  AAAGGCCAGC
1551  AAAAGGCCAG  GAACCGTAAA  AAGGCCCGCGT  TGCTGGCGTT  TTTCCATAGG
1601  CTCCGCCCCC  CTGACGAGCA  TCACAAAAAT  CGACGCTCAA  GTCAGAGGTG
1651  GCGAAACCCG  ACAGGACTAT  AAAGATACCA  GGCGTTTCCC  CCTGGAAGCT
1701  CCCTCGTGCG  CTCTCCTGTT  CCGACCCTGC  CGCTTACCGG  ATACCTGTCC
1751  GCCTTTCTCC  CTTCGGGAAG  CGTGGCGCTT  TCTCAATGCT  CACGCTGTAG
1801  GTATCTCAGT  TCGGTGTAGG  TCGTTCGCTC  CAAGCTGGGC  TGTGTGCACG
```

FIG. 7c

```
1851  AACCCCCCGT  TCAGCCCGAC  CGCTGCGCCT  TATCCGGTAA  CTATCGTCTT
1901  GAGTCCAACC  CGCTAAGACA  CGACTTATCG  CCACTGGCAG  CAGCCACTGG
1951  TAACAGGATT  AGCAGAGCGA  GGTATGTAGG  CGGTGCTACA  GAGTTCTTGA
2001  AGTGGTGGCC  TAACTACGGC  TACACTAGAA  GGACAGTATT  TGGTATCTGC
2051  GCTCTGCTGA  AGCCAGTTAC  CTTCGGAAAA  AGAGTTGGTA  GCTCTTGATC
2101  CGGCAAACAA  ACCACCGCTG  GTAGCGGGTGG  TTTTTTTGTT  TGCAAGCAGC
2151  AGATTACGCG  CAGAAAAAAA  GGATCTCAAG  AAGATCCTTT  GATCTTTTCT
2201  ACGGGGTCTG  ACGCTCAGTG  GAACGAAAAC  TCACGTTAAG  GGATTTTGGT
2251  CATGAGATTA  TCAAAAGGA   TCTTCACCTA  GATCCTTTA   AATTAAAAAT
2301  GAAGTTTTAA  ATCCCTCTAA  AGTATATATG  AGTAAACTTG  GTCTGACAGT
2351  TACCAATGCT  TAATCAGTGA  GGCACCTATC  TCAGCGATCT  GTCTATTTCG
2401  TTCATCCATA  GCTGCCTGAC  TCCCCGTCGT  GTAGATAACT  ACGATACGCG
2451  AGGGCTTACC  ATCTGGCCCC  AGTGCTGCAA  TGATACCGCG  AGACCCACGC
```

FIG. 7d

```
2501  TCACCGGCTC  CAGATTTATC  AGCAATAAAC  CAGCCAGCCG  GAAGGGCCGA
2551  GCGCAGAAGT  GGTCCTGCAA  CTTTATCCGC  CTCCATCCAG  TCTATTAATT
2601  GTTGCCGGGA  AGCTAGAGTA  AGTAGTTCGC  CAGTTAATAG  TTTGCGCAAC
2651  GTTGTTGCCA  TTGCTACAGG  CATCGTGGTG  TCACGCTCGT  CGTTTGGTAT
2701  GGCTTCATTC  AGCTCCGGTT  CCCAACGATC  AAGGCGAGTT  ACATGATCCC
2751  CCATGTTGTG  CAAAAAAGCG  GTTAGCTCCT  TCGGTCCTCC  GATCGTTGTC
2801  AGAAGTAAGT  TGGCCCGCAGT  TGGCCCGCAGT  ATGGTTATGG  CAGCACTGCA
2851  TAATTCTCTT  ACTGTCATGC  CATCCGTAAG  ATGCTTTCT  GTGACTGGTG
2901  AGTACTCAAC  CAAGTCATTC  TGAGAATAGT  GTATGCGGGCG  ACCGAGTTGC
2951  TCTTGCCCGG  CGTCAATACG  GGATAATACC  GCGCCACATA  GCAGAACTTT
3001  AAAAGTGCTC  ATCATTGGAA  AACGTTCTTC  GGGGCGAAAA  CTCTCAAGGA
3051  TCTTACCGCT  GTTGAGATCC  AGTTCGATGT  AACCCACTCG  TGCACCCAAC
3101  TGATCTTCAG  CATCTTTTAC  TTTCACCAGC  GTTTCTGGGT  GAGCAAAAAC
3151  AGGAAGGCAA  AATGCCGCAA  AAAAGGGAAT  AAGGGCGACA  CGGAAATGTT
3201  GAATACTCAT  ACTCTTCCTT  TTTCAATATT  ATTGAAGCAT  TTATCAGGGT
3251  TATTGTCTCA  TGAGCGGATA  CATATTTGAA  TGTATTTAGA  AAAATAAACA
3301  AATAGGGGTT  CCGCGCACAT  TTCCCCGAAA  AGTGCCACCT  GACGTCTAAG
3351  AAACCATTAT  TATCATGACA  TTAACCTATA  AAAATAGGCG  TATCACGAGG
3401  CCCTTTCGTC  TTCAC
```

FIG. 7e

```
                                                                    Xhol
  1    CTCGAGAAAT  CATAAAAAAT  ATTGTGAGCG  TTATTGCTT   TGTGAGCGGA  TAACAATTAT 51    AATAGATTCA  ATTGTGAGCG  GATAACAATT                          EcoRI
                                           TCACACAGAA  TTCATTAAAG BamHI       Sall        Pstl    HindIII
101    AGGAGAAATT  AACTATGAGG  ATCCGTCGAC  CTGCAGCCAA  GCTTAATTAG
                   MetArg      IleArgArgP  roAlaAlaLy  sLeuAsn

151    CTGAGCTTGG  ACTCCTGTTG  ATAGATCCAG  TAATGACCTC  AGAACTCCAT

201    CTGGATTTGT  TCAGAACGCT  CGGTTGCCGC  CGGGCGTTT   TTATTGGTGA

251    GAATCCAAGC  TAGCTTGGCG  AGATTTTCAG  GAGCTAAGGA  AGCTAAAATG

301    GAGAAAAAA   TCACTGGATA  TACCACCGTT  GATATATCCC  AATGGCATCG

351    TAAAGAACAT  TTTGAGGCAT  TTCAGTCAGT  TGCTCAATGT  ACCTATAACC

401    AGACCGTTCA  GCTGGATATT  ACGGCCTTT   TAAAGACCGT  AAAGAAAAT

451    AAGCACAAGT  TTTATCCGGC  CTTTATTCAC  ATTCTTGCCC  GCCTGCTGAA

501    TGCTCATCCG  GAATTTCGTA  TGGCAATGAA  AGACGGTGAG  CTGGTGATAT

551    GGGATAGTGT  TCACCCTTGT  TACACCGTTT  TCCATGAGCA  AACTGAAACG
```

FIG. 9a

```
601   TTTCATCGC  TCTGGAGTGA  ATACCACGAC  GATTTCCGGC  AGTTTCTACA
651   CATATATTCG  CAAGATGTGG  CGTGTTACGG  TCTCAGCCAA  GCCTATTTCC
701   CTAAAGGGT   TATTGAGAAT  ATGTTTTCG   TCTCAGCCAA  TCCCTGGGTG
751   AGTTTCACCA  GTTTTGATTT  AAACGTGGCC  AATATGGACA  ACTTCTTCGC
801   CCCCGTTTC   ACCATGGGCA  AATATTATAC  GCAAGGCGAC  AAGGTGCTGA
851   TGCCGCTGGC  GATTCAGGTT  ACAACAGTAC  CATCATGCCG  TCTGTGATGG
901   GGCAGAATGC  TTAATGAATT  GTTATTGGTG  TGCGATGAGT  GGCAGGGCGG
951   GGCGTAATTT  TTTTAAGGCA  TCAAATAAAA  CCCTTAAACG  CCTGGGGTAA
1001  TGACTCTCTA  GCTTGAGGCA  GTTGTTTGTC  CGAAAGGCTC  AGTCGAAAGA
1051  CTGGGCCTTT  CGTTTTATCT  AGCTGCCTCG  GGTGAACGCT  CTCCTGAGTA
                              Xbal
1101  GGACAAATCC  GCCGCTCTAG  AGCTGCCTCG  CGCGTTTCGG  TGATGACGGT
```

FIG. 9b

```
1151  GAAAACCTCT  GACACATGCA  GCTCCCGGAG  ACGGTCACAG  CTTGTCTGTA
1201  AGCGGATGCC  GGGAGCAGAC  AAGCCCGTCA  GGGCGCGTCA  GCGGGTGTTG
1251  GCGGGTGTCG  GGGCGCAGCC  ATGACCCAGT  CACGTAGCGA  TAGCGGAGTG
1301  TATACTGGCT  TAACTATGCG  GCATCAGAGC  AGATTGTACT  GAGAGTGCAC
1351  CATATGCGGT  GTGAAATACC  GCACAGATGC  GTAAGGAGAA  AATACCGCAT
1401  CAGGCGCTCT  TCCGCTTCCT  CGCTCACTGA  CTCGCTGCGC  TCGGTCTGTC
1451  GGCTGCGGCG  AGCGGTATCA  GCTCACTCAA  AGGCGGTAAT  ACGGTTATCC
1501  ACAGAATCAG  GGGATAACGC  AGGAAAGAAC  ATGTGAGCAA  AAGGCCAGCA
1551  AAAGGCCAGG  AACCGTAAAA  AGGCCGCGTT  GCTGGCGTTT  TTCCATAGGC
1601  TCCGCCCCCC  TGACGAGCAT  CACAAAAATC  GACGATCAAG  TCAGAGGTGG
1651  CGAAACCCGA  CAGGACTATA  AAGATACCAG  GCGTTTCCCC  CTGGAAGCTC
1701  CCTCGTGCGC  TCTCCTGTTC  CGACCCTGCC  GCTTACCGGA  TACCTGTCCG
1751  CCTTTCTCCC  TTCGGGAAGC  GTGGCGCTTT  CTCAATGCTC  ACGCTGTAGG
1801  TATCTCAGTT  CGGTGTAGGT  CGTTCGCTCC  AAGCTGGGCT  GTGTGCACGA
```

FIG. 9c

```
1851  ACCCCCCGTT  CAGCCCGACC  GCTGCGCCTT  ATCCGGTAAC  TATCGTCTTG
1901  AGTCCAACCC  GGTAAGACAC  GACTTATCGC  CACTGGCAGC  AGCCACTGGT
1951  AACAGGATTA  GCAGAGCGAG  GTATGTAGGC  GGTGCTACAG  AGTTCTTGAA
2001  GTGGTGGCCT  AACTACGGCT  ACACTAGAAG  GACAGTATTT  GGTATCTGCG
2051  CTCTGCTGAA  GCCAGTTACC  TTCGGAAAAA  GAGTTGGTAG  CTCTTGATCC
2101  GGCAAACAAA  CCACCFGCTG  TAGCGGTGGT  TTTTTGTTT  GCAAGCAGCA
2151  GATTACGCGC  AGAAAAAAAG  GATCTCAAGA  AGATCCCTTG  ATCTTTTCTA
2201  CGGGGTCTGA  CGCTCAGTGG  AACGAAAACT  CACGTTAAGG  GATTTTGGTC
2251  ATGAGATTAT  CAAAAAGGAT  CTTCACCTAG  ATCCTTTTAA  ATTAAAAATG
2301  AAGTTTTAAA  TCAATCTAAA  GTATATATGA  GTAAACTTGG  TCTGACAGTT
2351  ACCAATGCTT  AATCAGTGAG  GCACCTATCT  CAGCGATCTG  TCTATTTCGT
2401  TCATCCATAG  CTGCCTGACT  CCCCGTCGTG  TAGATAACTA  CGATACGGGA
2451  GGGCTTACCA  TCTGGCCCCA  GTGCTGCAAT  GATACCGCGA  GACCCACGCT
```

FIG. 9d

```
2501  CACCGGCTCC AGATTTATCA GCAATAAACC AGCCAGCCGG AAGGGCCGAG
2551  CGCAGAAGTG GTCCTGCAAC TTTATCCGCC TCCATCCAGT CTATTAATTG
2601  TTGCCGGGAA GCTAGAGTAA GTAGTTCGCC AGTTAATAGT TTGCGCAACG
2651  TTGTTGCCAT TGCTACAGGC ATCGTGGTGT CACGCTCGTC GTTTGGTATG
2701  GCTTCATTCA GCTCCGGTTC CCAACGATCA AGGCGAGTTA CATGATCCCC
2751  CATGTTGTGC AAAAAAGCGG TTAGCTCCTT CGGTCCTCCG ATCGTTGTCA
2801  GAAGTAAGTT TTATCACTCA TTATCACTCA TGGTTATGGC AGCACTGCAT
2851  AATTCTCTTA CTGTCATGCC ATCCGTAAGA TGCTTTTCTG TGACTGGTGA
2901  GTACTCAACC AAGTCATTCT GAGAATAGTG TATGCGGGCA CCGAGTTGCT
2951  CTTGCCCGGC GTCAATACGG GATAATACCG CGCCACATAG CAGAACTTTA
3001  AAAGTGCTCA TCATTGGAAA ACGTTCTTCG GGGCGAAAAC TCTCAAGGAT
3051  CTTACCGCTG TTGAGATCCA GTTCGATGTA ACCCACTCGT GCACCCAACT
3101  GATCTTCAGC ATATTTTACT TTCACCAGCG TTTCTGGGTG AGCAAAAACA
3151  GGAAGGCAAA ATGCCGCAAA AAAGGGAATA AGGGCGAATA GGAAATGTTG
3201  AATACTCATA CTCTTCCTTT TTCAATATTA TTGAAGCATT TATCAGGGTT
3251  ATTGTCTCAT GAGCGGATAC ATATTTGAAT GTATTTAGAA AAATAAACAA
3301  ATAGGGGTTC CGCGCACATT TCCCCGAAAA GTGCCACCTG ACGTCTAAGA
3351  AACCATTATT ATCATGACAT TAACCTATAA AAATAGGCGT ATCACGAGGC
3401  CCTTTCGTCT TCAC
```

FIG. 9e

```
        HindIII
   1    AAGCTTCACG  CTGCCGCAAG  CACTCAGGGC  GCAAGGGCTG  CTAAAGGAAG
  51    CGGAACACGT  AGAAGCCAG   TCCGCAGAAA  CGGTGCTGAC  CCCGGATGAA
 101    TGTCAGCTAC  TGGGCTATCT  GGACAAGGGA  AAACGCAAGC  GCAAAGAGAA
 151    AGCAGGTAGC  TTGCAGTGGG  CTTACATGGC  GATAGCTAGA  CTGGGCGGTT
 201    TTATGGACAG  CAAGCGAACC  GGAATTGCCA  GCTGGGGCCGC CCTCTGGTAA
 251    GGTGGGAAG   CCCTGCAAAG  TAAACTGGAT  GGCTTCTTG   CCGCCAAGGA
 301    TCTGATGGCG  CAGGGATCA   AGATCTGATC  AAGAGACAGG  ATGAGGATCG
 351    TTTCGCATGA  TTGAACAAGA  TGGATTGCAC  GCAGGTTCTC  CGGCCGCTTG
         Met
 401    GGTGGAGAGG  CTATTCGGCT  ATGACTGGGC  ACAACAGACA  ATCGGCTGCT
 451    CTGATGCCGC  CGTGTTCCGG  CTGTCAGCGC  AGGGGCGCCC  GGTTCTTTT
 501    GTCAAGACCG  ACCTGTCCGG  TGCCCTGAAT  GAACTGCAGG  ACGAGGCAGC
 551    GCGGCTATCG  TGGCTGGCCA  CGACGGGCGT  TCCTTGCGCA  GCTGTGCTCG
 601    ACGTTGTCAC  TGAAGCGGGA  AGGGACTGGC  TGCTATTGGG  CGAAGTGCCG
 651    GGGCAGGATC  TCCTGTCATC  TCACCTTGCT  CCTGCCGAGA  AAGTATCCAT
```

FIG. 11a

```
 701  CATGGCTGAT  GCAATGCGGC  GGCTGCATAC  GCTTGATCCG  GCTACCTGCC
 751  CATTCGACCA  CCAAGGCAAA  CATCGCATCG  AGCGAGCACG  TACTCGGATG
 801  GAAGCCGGTC  TTGTCGATCA  GGATGATCTG  GACGAAGAGC  ATCAGGGGCT
 851  CGCGCCAGCC  GAACTGTTCG  CCAGGCTCAA  GGCGGCATG   CCCGACGGCG
 901  AGGATCTCGT  CGTGACCCAT  GGCGATGCCT  GCTTGCCGAA  TATCATGGTG
 951  GAAAATGGCC  GCTTTTCTGG  ATTCATCGAC  TGTGGCCGGC  TGGGTGTGGC
1001  GGACCGCTAT  GCTTTTCTGG  ATTCATCGAC  TGTGGCCGGC  TGGGTGTGGC
1051  TTGGGGCGA   ATGGGCTGAC  CGCTTCCTCG  TGCTTTACGG  TATCGCCGCT
1101  CCCGATTCGC  AGCCGCATCGC CTTCTATCGC  CTTCTTGACG  AGTTCTTCTG
                                                     Phe
1151  AGCGGGACTC  TGGGGTTCGA  AATGACCGAC  CAAGCGACGC  CCAACCTGCC
```

FIG. 11b

```
1201  ATCACGAGAT  TTCGATTCCA  CCGCCGCCCT  CTATGAAAGG  TTGGGCTTCG
1251  GAATCGTTTT  CCGGGACGCC  GGCTGGATGA  TCCTCCAGCG  CGGGGCTCTC
1301  ATGCTGGAGT  TCTTCGCCCA  CCCCGGGCTC  GATCCCCTCG  CGAGTTGGTT
1351  CAGCTGCTGC  CTGAGGCTGG  ACGACCTCGC  GGAGTTCTAC  CGGCAGTGCA
1401  AATCCGTCGG  CATCCAGGAA  ACCAGCAGCG  GCTATCCGCG  CATCCATGCC
                                                              Sal I
1451  CCCGAACTGC  AGGAGTGGGG  AGGCACGATG  GCCGCTTTGG  TCGACAATTC
1501  GCGCTAACTT  ACATTAATTG  CGTTGCGCTC  ACTGCCCGCT  TTCCAGTCGG
                                          (Gln)
1551  GAAACCTGTC  GTGCCAGCTG  CATTAATGAA  TCGGCCAACG  CGCGGGGAGA
1601  GGCGGTTTGC  GTATTGGGCG  CCAGGGTGGT  TTTTCTTTTC  ACCAGTGAGA
1651  CGGGCAACAG  CTGATTGCCC  TTCACCGCCT  GGCCCTGAGA  GAGTTGCAGC
1701  AAGCGGTCCA  CGCTGGTTTG  CCCCAGCAGG  CGAAAATCCT  GTTTGATGGT
1751  GGTTAACGGC  GGGATATAAC  ATGAGCTGTC  TTCGGTATCG  TCGTATCCCA
1801  CTACCGAGAT  ATCCGCACCA  ACGCGCAGCC  CGGACTCGGT  AATGGCGCGC
```

FIG. 11c

```
1851  ATTGCGCCCA GCGCCATCTG ATCGTTGGCA ACCAGCATCG CAGTGGGAAC
1901  GATGCCCTCA TTCAGCATTT GCATGGTTTG TTGAAACCG GACATGGCAC
1951  TCCAGTCGCC TTCCCGTTCC GCTCTCGGCT GAATTTGATT GCGAGTGAGA
2001  TATTTATGCC AGCCAGCCAG ACGCAGACGC GCCGAGACAG AACTTAATGG
2051  GCCCGCTAAC AGCGCGATTT GCTGGTGACC CAATGCGACC AGATGCTCCA
2101  CGCCCAGTCG CGTACCGTCT TCATGGGAGA AAATAATACT GTTGATGGGT
2151  GTCTGGTCAG AGACATCAAG AAATAACGCC GGAACATTAG TGCAGGCAGC
2201  TTCCACAGCA ATGGCATCCT GGTCATCCAG CGGATAGTTA ATGATCAGCC
2251  CACTGACGCG TTGCGCGAGA AGATTGTGCA CCGCCGCTTT ACAGGCTTCG
2301  ACGCCGCTTC GTTCTACCAT CGACACCACC ACGCTGGCAC CCAGTGATC
2351  GGCGCGAGAT TTAATCGCCG CGACAATTTG CGACGGCGCG TGCAGGGCCA
2401  GACTGGAGGT GGCAACGCCA ATCAGCAACG ACTGTTTGCC CGCCAGTTGT
```

FIG. 11d

```
TCGGCGGTTTCGGTGATGACGGTGAAAACCTCTGACACATGCAGCTCCCGGAGACGGTCA
                                                              60
AGCGCGCAAAGCCACTACTGCCACTTTGGAGACTGTGTACGTCGAGGGCCTCTGCCAGT

CAGCTTGTCTGTAAGCGGATGCCGGGAGCAGACAAGCCCGTCAGGGCGCGTCAGCGGGTG
                                                              120
GTCGAACAGACATTCGCCTACGGCCCTCGTCTGTTCGGGCAGTCCCGCGCAGTCGCCCAC

TTGGCGGGTGTCGGGGCTGGCTTAACTATGCGGCATCAGAGACAGATTGTACTGAGAGTGC
                                                              180
AACCGCCCACAGCCCCGACCGAATTGATACGCCGTAGTCTCGTCTAACATGACTCTCACG

ACCATATGCGGTGTGAAATACCGCACAGATGCGTAAGGAGAAATACCGCATCAGGCGCC
                                                              240
TGGTATACGCCACACTTTATGGCGTGTCTACGCATTCCTCTTTATGGCGTAGTCCGCGG

ATTCGCGCCATTCAGGCTGCGCAACTGTTGGGAAGGGCGATCGGTGCGGGCCTCTTGCTAT
                                                              300
TAAGCGCGGTAAGTCCGACGCGTTGACAACCCTTCCCGCTAGCCACGCCCGGAGAAGCGATA

TACGCCAGCTGGGCGAAAGGGGGATGTGCTGCAAGGCGATTAAGTTGGGTAACGCCAGGGT
                                                              360
ATGCGGTCGACCGGCTTTCCCCCTACACGACGTTCCGCTAATTCAACCCATTGCGGTCCCA
```

FIG. 14a

```
TTTCCAGTCACGACGTTGTAAAACGACGGCCAGTGCCAAGCTAGCTTTTGCGATCAATA
                                                              420
AAAGGGTCAGTGCTGCAACATTTGCTGCCGGTCACGTTCGATCGAAAACGCTAGTTAT
                                                              480
AACTGGATCACAACCAGTATCTCTTAACGATGTCTTCGCAGATGATGATTCATTTTTA
TTGACCTAGTGTTGGTCATAGAGAATTGCTACAGAAGCGTCTACTACTAAGTAAAAAT
                                                              540
AGTATTGGCTAGTCAAGATGATGAATCTTCATTATCTGATATATTGCAAATCACTCAAT
TCATAAACGATCAGTTCTACTACTAGAGAAGTAATAGACTATATAACGTTAGTGAGTTA
                                                              600
ATCTAGAGACTTTCTGTTATTATTATTGATCCAATCAAAAATAAATTAGAAGCCGTGGGTC
TAGATCTGAAAGACAATAATAACTAGGTTAGTTTTTATTAATCTTCGGCACCCAG
ATTGTTATGAATCTCTTTCAGAGGAATACAGAGACAAAATTCACAGACTTTCAAG
                                                              660
TAACAATACTAGAGAAAGTCTCCTATGTCTGTTAACTGTTTAAGTGTCTGAAAGTC
```

FIG. 14b

```
ATTTTAAAAAACTGTTAACAAGGTCCCTATTGTTACAGATGGAAGGGTCAAACTTAATA
                                                              720
TAAAATTTTTGACAAATTGTTCCAGGGATAACAATGTCTACCTTCCCAGTTTGAATTAT
                                                              780
AAGGATATTTCTTCGACTTTGTGATTAGTTTGATGCGATTCAAAAAGAATCCTCTCTAG

TTCCTATAAGAAGCTGAAACACTAATCAAACTACGCTAAGTTTTTCTTAGGAGAGATC
                                                              840
CTACCACGCAATAGATCCTGTTAGATACATAGATCCTCGTCGCAATATCGCATTTTCTA

GATGGTGGCGTTATCTAGGACAATCTATGTATCTAGGAGCAGGCGTTATAGCGTAAAGAT
                                                              900
ACGTAGTGGATATATTAAAGTCGAATAAAGTGAACAATAATAATTCTTATTGTCATCA

TGCATCACCTATATAATTCAGCTTATTCACTGTTATTAATTAAGAAATAACAGTAGT
                                                              960
TGAACGGCGGACATATTCAGTTGATAATCGGCCCATGTTTTCAGGTAAAGTACAGAAT

ACTTGCCGCCTGTATAAGTCAACTATTAGCCGGGGTACAAAAGTCCATTTCATGTCTTA
                                                              1020
TAATTAGACGAGTTAGACGTTATCAAATAGCTCAATATAAATGCGTGACTATAAATATT

ATTAATCTGCTCAATCTGCAATAGTTTTATCGAGTTATATTACGCACTGATATTTTATAA
```

FIG. 14c

```
CTAACGATAATAGATACGGAAGGGACTATGGAGGACGCATGATAAGAATAATTTGAAGCAT
------------------------------------------------------------  1080
GATTGCTATTATCTATGCCTTCCCCTGATACCTGCTACTATTCTTATTAAAACTTCGTA
------------------------------------------------------------  1140
TGGAAGCAACTAAACTATGTGATGTCTTGGAATCAATTACAGATTTCTCCGTGATAGGTA
------------------------------------------------------------  1200
ACCTTCGTTGATTGATACACTACAGAACCTAGTAATGTCTAAAGAGGCACTATCCAT
TCGACATCTATATACTATATAGTAATACCAATACTCAAGACTACGAAACTGATACAATCT
AGCTGTAGATATATGATATCATTATGGTTATGAGTTCTGATGCTTTGACTATGTTAGA
------------------------------------------------------------  1260
CTTATCATGTGGGTAATGTTCTCGATGTCGAATAGCCATATGCCGGTAGTTCGCATATAC
GAATAGTACACCCATTACAAGAGCTACAGCTTATCGGTATACGGCCATCAAGGCTATATG
------------------------------------------------------------  1320
ATAAACTGATCACTAATTCCAAACCCACCCGCTTTTATAGTAAGTTTTCACCGATAAA
TATTTGACTAGTGATTAAGGTTTGGGTGGGCGAAAAATATCATTCAAAAAGTGGCTATT
```

FIG. 14d

```
TAATAAATACAATAATTAATTTCTCGTAAAAGTAGAAAATATATTCTAATTTATTGCACG
                                                              1380
ATTATTTATGTTATTAATTAAAGAGCATTTCATCTTTATATAAGATTAAATAACGTGC
                                                              1440
GTAAGGAAGTAGAATCATAAAGAAGTCAGATCGGGAATTCGGCTTTTGCGTCGGAGAT
CATTCCTTCCTCATCTTAGTATTTCTTGTCAGTCTCTAGCCCCTTAAGCCGAAAACGCAGCCTCTA
                                                              1500
AGTCGTTGTGTGTTGCGCGATCACCCGGCGAACTTCTCTACCAACTGAAAATGGCTAAGT
                                                                M A K S
TCAGCAACACACAAACGCGCTAGTGGGCGCTTGAAGAGATGGTTGACTTTTACCGATTCA
                                                              1560
CTATGCTTTCTGGAATTGTTTTTGCTGGTCTTGTTGCTGCAGCGGCCAGTTCGGCCA
 M  L  S  G  I  V  F  A  G  L  V  A  A  A  A  S  S  A
GATACGAAAGACCTTAACAAAAACGACCAGAACAACGACGTCGCGGTCAAGCCGGT
    N
                                                              1620
ACAGCGCCGCCAACGTCTCCGTTTTGGAGAGTGGGCCCGCTGTGCAGGAAGTGCCAGCGC
 S  A  A  N  V  S  V  L  E  S  G  P  A  V  Q  E  V  P  A  R
TGTCGCGGGGTTGCAGAGGCAAACCTCTCACCCGGGCGACACGTCCTTCACGGTCGCG
```

FIG. 14e

```
GCACGGTCACAGCTCGGCCTGGCGAAGCCTTTGCTGCTCTTTCTGCTCTCTTGCTCTGCTGACTT
                                                              1680
CGTGCCAGTGTCGAGCGGACCGCTTCGGAAGCGACGAAGAGAACGACGAGCTGAA
 T  V  T  A  R  L  A  K  P  L  L  L  L  S  A  L  A  A  T  L

TGGCAGCAGCTTTCCTCGTTTGCAATGCTTCAACAGCATCTCCAGCAACAACCAGCAAA
                                                          1740
ACCGTCGTCGAAAGGAGCAAACGTTACGAAGTGTGTAGAGGTCGTTGTTGGTCGTT
 A  A  A  F  L  V  L  Q  C  F  N  T  I  S  S  N  N  Q  Q  T

CCAGCGGTCAGGAGACTGGGCCGCCGAGGTGCATGCCGGAGATGAGGAAGATGCAGATGAGG
                                                           1800
GGTCGCCAGTCCTCTGACCCGGCGGCTCCACGTACGGCCTCTACTCCTTCTACGTCTACTCC
 S  V  R  R  L  A  A  G  G  A  C  G  D  E  E  D  A  D  E  G

GAACTTCACAGCAGCCGGAGCCGGGAGGAGAGAAAACCTGATACCCCTGCAGCAGATAAAT
                                                             1860
CTTGAAGTGTCGTCGGCCTCGGCCCTCCTCTCTTTTGGACTATGGGGACGTCGTCTATTTA
 T  S  Q  Q  A  S  R  R  R  R  K  P  D  T  P  A  A  D  K  Y
```

FIG. 14f

```
ACGATTTGTTGGGCGGAACTCCAGTTTCGGTCACTGAGCCGAATGTTGATGAAGTCCTTA
                                                                    1920
TGCTAAACAACCGCCCTTGAGGTCAAAGCCAGTGACTCGGCTTACAACTACTTCAGGAAT

D   F   V   G   G   T   P   V   S   V   T   E   P   N   V   D   E   V   L   I

TCCAAATTAGAAATAAACAAATGTTTTAGAAAACTTCTGGGTACCTGACTGGACAAGAACAAG
                                                                    1980
AGGTTTAATCTTTATTTGTTTACAAAATCTTTTGAAGACCCATGGACTGACCTGTTCTTGTTC

Q   I   R   N   K   Q   I   F   L   K   N   P   W   T   G   Q   E   E   Q   V

TTCTAGTACTGGAACGACAAAGTGAAGAACCCATTCTGATTGTGGCGAGGACAAGACAAA
                                                                    2040
AAGATCATGACCTTGCTGTTCACTTCTTGGGTAAGACTAACACCGCTCCTGTTCTGTTT

L   V   L   E   R   Q   S   E   E   P   I   L   I   V   A   R   T   R   Q   T

CACTTGAAGGATATCTTGGTAGTCAAGCTCTTGCACAGGACGGAAAGACTGCTAAAGAAG
                                                                    2100
GTGAACTTCCTATAGAACCATCAGTTCGAGAACGTGTCCTGCCTTTCTGACGATTTCTTC

L   E   G   Y   L   G   S   Q   A   L   A   Q   D   G   K   T   A   K   E   E

AGAAAGTTGAAGGAGGCAAAACTCACAGAAGATATAAAGTCAAGAGAGCAGGACCCAGGAT
                                                                    2160
TCTTTCAACTTCCTCCGTTTGAGTGTCTTCTATATTCAGTTCTGCTGCGTGGTCCTA
```

FIG. 14g

```
K V E G G K T H R R Y K V K S S D D P G Y
ATGGATTCCCATACACCACGGTCGTCGACGGGTTCCTGTGGAACAGACGAAGACGGAT   2220
TACCTAAGGGTATGTGGTGCCACGAGCTGCCCAAGGACACCCTTGTCTGCTTCTGCCTA

G F P Y T T V L D G V P V G T D E D G Y
ACGTCGTCGAAGTTCTTATGAAAACCGGACCCCATGGAGGAGTCGACATGATGACTAGCA   2280
TGCAGCAGCTTCAAGAATACTTTTGGCCTGGGGTACCTCCTCAGCTGTACTACTGATCGT

V V E V L M K T G P H G G V D M M T S T
CAGCATCACAAGGAAAATTCTGCGGAGTGCTTATGATGACGGAAAAGGAAACCTAGTCG   2340
GTCGTAGTGTTCCTTTTAAGACGCCTCACGAATACCTACTGCCTTTCCTTTGGATCAGC

A S Q G K F C G V L M D D G K G N L V D
ATGGACAAGGAGAAAAATTACCGCCGTTATCGGCATGCTAACTCAACCGGATACCGAGT   2400
TACCTGTTCCCTCTTTTTAATGGCGGCAATAGCCGTTGAGTTGGCCTATGGCTCA

```
TTAATAATATTTGAATCTTATTCCATTATCTGAAATGGTGGTAAAACTAACTGCTGTG
                                                              ───── 2460
AATCTTCGGCCTGGTCCTGCTGCTGCTCCTGCTCACTCGCCTCAACCGAAAACAG

CCTGTTGATGCCGTTGCCCTGCAGCTTCGCCACTTCGCAGCTTGCTGTTCCTGGCTTGCCTGTGCCGC
                                                              ───── 2520
  R   S   G   P   G   D   D   E   D   D   E   -
GGACAACTACGGCAACGGGTGAAAGGCGTCGAACGAACAAAGGACCCGAACGGACACGGCG

GACATGCGCTTGGGCGTTCCGCCTGAGTTCTTTAACTTTAATTCATTT
                                                              ───── 2580
CTGTACGCGAACCGCAAGGCGGACTCAAGAAAGCCTGACAAATTGAAATTAAGTAAAA

CTACTGCGGGCAAAAAAAAAAAAAAAAAACGAATTCTGTGAGCGTATG
                                                              ───── 2640
GATGACGCCGTTTTTTTTTTTTTTTTTGGCTAAGACACTCGCATAC

GCAAACGAAGGAGAAAATAGTTATAGTAGCCGCACTCGATGGGACATTTCAACGTAAACCG
                                                              ───── 2700
CGTTTGCTTCCTTTTATCAATATCATCGGCGTGAGCTACCCTGTAAAGTTGCATTGGC
```

FIG. 14i

```
TTTAATAATATTTTGAATCTTATTCCATTATCTGAAATGGTGGTAAAACTAACTGCTGTG
                                                              2760
AAATTATTATAAACTTAGAATAAGGTAATAGACTTTACCACCATTTTGATTGACGACAC

TGTATGAAATGCTTTAAGGAGGCTCCTTTTCTAAACGATTGGGTGAGGAAACCGAGATA
                                                              2820
ACATACTTTACGAAATTCCTCCGAAGGAAAAGATTGCTAACCCACTCCTTGGCTCTAT

GAAATAATAGGAGGTAATGATATCAATCGGTGTGTAGAAAGTGTTACATCGACTCA
                                                              2880
CTTTATTCCTCCATTACTATACATAGTTAGCCACACATCTTCACAATGTAGCTGAGT

TAATATTATATTTTTATCTAAAAAACTAAAAAATAAACATTGATTAAATTTAATATAAT
                                                              2940
ATTATATATAAAAATAGATTTTTGATTTTATTGTAACTAATTAAAATTATATTA

ACTTAAAAATGGATGTGTGTCGTTAGATAAACCGTTATGTATTTGAGGAAATTGATA
                                                              3000
TGAATTTTTACCTACAACACAGCAATCTATTGGCAAATACATAAAACTCCTTAACTAT

ATGAGTTAAATTACGAACCAGAAAGTGCAAATGAGGCCGCAAAAAACTGCCGTATCAAG
                                                              3060
TACTCAATTAATGCTTGGTCTTTCACGTTACTCCGGGCGTTTTTGACGGCATAGTTC
```

FIG. 14j

```
GACAGTTAAAACTATTACTAGGAGAATTATTTTTCTTAGTAAGTTACAGGCGACACGGTA
                                                            3120
CTGTCAATTTGATAATGATCCTCTTAATAAAAAGAATCATTCAATGTCGCTGTGCCAT

TATTAGATGGTGCCACCGTAGTGTATATAGGATCTGCTCCCCGTAATCATGGTCATAGCT
                                                            3180
ATAATCTACCACGGTGGCATCACATATATCCTAGACGAGGGCATTAGTACCAGTATCGA

GTTTCCTGTGTGAAATTGTTATCCGCTCACAATTCCAGAGAAGATACGAGCCGGAAGCAT
                                                            3240
CAAAGGACACACTTTAACAATAGGCGAGTGTTAAGGTGTGTTGTATGCTCGGCCTTCGTA

AAAGTGTAAAGCCTGGGGTGCCTAATGAGTGAGCTAACTCACATTAATTGCGTTGCGCTC
                                                            3300
TTTCACATTTCGGACCCCACGGATTACTCACTCGATTGAGTGTAATTAACGCAACGCGAG

ACTGCCCGCTTTCCAGTCGGGAAACCTGTCGTGCCAGCTGCATTAATGAATCGGCCAACG
                                                            3360
TGACGGGCGAAAGGTCAGCCCTTTGGACAGCACGGTCGACGTAATTACTTAGCCGGTTGC

CGCGGGGAGAGGCGGTTTGCGTATTGGGCGCTCTTCCGCTTCCTCGCTCACTGACTCGCT
                                                            3420
GCGCCCCTCTCCGCCAAACGCATAACCCGCGAGAAGGCGAAGGAGCGAGTGACTGAGCGA
```

FIG. 14k

```
GCGCTCGGTCGTTGCGGGCGAGCGGTATCAGCTCACTCAAAGGCGGTAATACGGTT   3480
CGCGAGCCAGCAAGCCCGACGCCCGCTCGCCATAGTCGAGTTTCCGCCATTATGCCAA

ATCCACAGAATCAGGGGATAACGCAGGAAAAGAACATGTGAGCAAAAGGCCAGCAAAAGGC   3540
TAGGTGTCTTAGTCCCCTATTGCGTCCTTTCTTGTACACTCGTTTCCG

CAGGAACCGTAAAAAGGACCGCGTTGCTGGCGTTTTTCCATAGGCTCCGCCCCCCTGACGA   3600
GTCCTTGGCATTTTTCCGGCGCAACGACCGCAAAAAGGTATCCGAGGCGGGGACTGCT

GCATCACAAAAATCGACGCTCAAGTCAGAGGTGGCGAAACCCGACAGGACTATAAAGATA   3660
CGTAGTGTTTTTAGCTGCGAGTTCAGTCTCCACGCTTTGGGCTGTCCTGATATTTCTAT

CCAGGGCGTTTCCCCCTGGAAGCTCCCTCGTGCGCTCTCCTGTTCCGACCCTGCCGCTTAC   3720
GGTCCGCAAAGGGGGACCTTCGAGGGAGCACGCGAGAGGACAAGGCTGGGACGGGCGAATG
```

FIG. 141

```
CGGATACCTGTGTCCGGCCTTTCTCCCTTCGGGAAGCGTGGCGCTTTCTCAATGCTCACGCTG
                                                                ——— 3780
GCCTATGGACAGGGCGGAAAGAGGGAAGCCCCTTCGCACCGCGAAAGAGTTACGAGTGCGAC

TAGGTATCTCAGTTCGGTGTAGGTCGTTCGCTCCAAGCTGGGCTGTGTGCACGAACCCCC
                                                                ——— 3840
ATCCATAGAGTCAAGCCACATCCAGCAAGCGAGGTTCGACCCGAGTCCAACCGGTAAG

CGTTCAGCCCGACCGCTGCGCCTTATCCGGTAACTATCGTCTTGAGTCCAACCGGTAAG
                                                                ——— 3900
GCAAGTCGGGCGACGCGGAATAGGCCATTGATAGCAGAACTCAGGTTGGGCCATTC

ACACGACTTATCGCCACTGGCAGCAGCCACTGTAACAGGATTAGCAGAGCGAGGTATGT
                                                                ——— 3960
TGTGCTGAATAGCGGTGACCGTGTCGGTGACCATTGTCCTAATCGTCTCGCTCCATACA

AGGCGGGTGCTACAGAGTTCTTGAAGTGGCCTAACTACGGCTACACTAGAAGGACAGT
                                                                ——— 4020
TCCGCCACGATGTCTCAAGAACTTCACCACCGGATTGATGCCGATGTGATCTTCCTGTCA

ATTTGGTATCTCGGCTCTGCTGAAGCCAGTTACCTTCGGAAAAGAGTTGGTAGCTCTTG
                                                                ——— 4080
TAAACCATAGAGCGCGAGACTTCGGTCAATGGAAGCCTTTTCTCAACCATCGAGAAC
```

FIG. 14m

```
ATCCGGCAAACAAACCACCGCTGGTAGCGGTGGTTTTTGTTGCAAGCAGCAGATTAC
                                                        4140
TAGGCCGTTGTTGGTGGCGACCATCGCCACCAAAAACAAACGTTCGTGTCTAATG

GCGCAGAGAAAAAGGATCTCAAGAAGATCCTTTGATCTCTTTCTACGGGGTCTGACGCTCA
                                                        4200
CGCGTCTCTTTTTCCTAGAGTTCTTCTAGGAAACTAGAAAGATGCCCCAGACTGCGAGT

GTGGAACGAAAACTCACGTTAAGGGATTTTGGTCATGAGATTATCAAAAAGGATCTTCAC
                                                        4260
CACCTTGCTTTTGAGTGCAATTCCCTAAAACCAGTACTCTAATAGTTTTCCTAGAAGTG

CTAGATCCTTTAAATTAAAAATGAAGTTTAAATCAATCTAAAGTATATATGAGTAAAC
                                                        4320
GATCTAGGAAATTTAATTTTACTTCAAATTTAGTTAGATTCATATATACTCATTTG

TTGGTCTGACAGTTACCAATGCTTAATCAGTGAGGCACCTATCTCAGCGATCTGTCTATT
                                                        4380
AACCAGACTGTCAATGGTTACGAATTAGTCACTCCGTGGATAGAGTCGCTAGACAGATAA
```

FIG.14n

```
TCGTTCATCCATAGTTGCCTGACTCCCCGTGTCTGTAGATAACTACGATACGGGAGGGCTT
AGCAAGTAGGTATCAACGGACTGAGGGGCAGCACATCTATTGATGCTATGCCCTCCCGAA  4440
ACCATCTGGCCCCAGTGCTGCAATGATACCGGAGACCCACGCTCACCGGCTCCAGATTT   4500
TGGTAGACCGGGGTCACGACGTTACTATGGCGCTCTGGGTGCGAGTGGCCGAGGTCTAAA
ATCAGCAATAAACCAGCCGGAAGGGCCGAGCGCAGAAGTGGTCCTGCAACTTTATC      4560
TAGTCGTTATTTGGTCGGTCGGCCTTCCCGGCTCGGTCTTCACCAGGACGTTGAAATAG
CGCCTCCATCCAGTCTATTAATTGTTGCGGGAAGCTAGAGTAAGTAGTTCGCCAGTTAA   4620
GCGGAGGTAGGTCAGATAATTAACAACGGCCCTTCGATCTCATTCATCAAGCGGTCAATT
TAGTTTGCGCAACGTTGTTGCCATTGCTACAGGCATGTCACGCTCGTGTCGTTTGG      4680
ATCAAACGCGTTGCAACAACGGTAACGATGTCCGTAGCACCACAGTGCGAGCAGCAAACC
TATGGCTTCATTCAGCTCCGGTTCCCAACGATCAAGGCGAGTTACATGATCCCCATGTT   4740
ATACCGAAGTAAGTCGAGGCCAAGGGTTGCTAGTTCCGCTCAATGTACTAGGGGGTACAA
```

FIG. 14o

```
GTGCAAAAAGCGGGTTAGCTCTCCTTCGGTCCTCCGATCGTTGTCAGAAGTAAGTTGGCCGC
------------------------------------------------------------ 4800
CACGTTTTTCGCCCAATCGAGAGGAAGCCAGGAGGCTAGCAACAGTCTTCATTCAACCGGCG

AGTGTTATCACTCATGGTTATGGCAGCACTGCATAATTCTCTACTGTCATGCCATCCGT
------------------------------------------------------------ 4860
TCACAATAGTGAGTACCAATATACCGTCGTGACGTATTAAGAGAATGACAGTACGGTAGGCA

AAGATGCTTTCTGTGACTGGTGAGTACTCAACCAGTCATTCTGAGAATAGTGTATGCG
------------------------------------------------------------ 4920
TTCTACGAAAGACACTGACCACTCATGAGTTGGTCAGTAAGACTCTTATCACATACGC

GCGACCGAGTTGCTCTGCCCGGGTCAATACGGGATAATACCGCCACATAGCAGAAC
------------------------------------------------------------ 4980
CGCTGGCTCAACGAGAACGGGCCCAGTTATGCCCTATTATGGCGGTGTATCGTCTTG

TTTAAAAGTGCTCATCATTGGAAAACGTTCTTCGGGGGCGAAAACTCTCAAGGATCTTACC
------------------------------------------------------------ 5040
AAATTTTCACGAGTAGTAACCTTTTGCAAGAAGCCCCGCTTTTGAGAGTTCCTAGAATGG
```

FIG. 14p

```
GCTGTTGAGATCCAGTTCGATGTAACCCACTCGTGCACCCAACTGATCTTCAGCATCTTT
     ---------+---------+---------+---------+---------+---------+  5100
CGACAACTCTAGGTCAAGCTACATTGGGTGAGCACGTGGGTTGACTAGAAGTCGTAGAAA

TACTTTCACCAGCGTTTCTGGGTGAGCAAAAACAGGAAGGCAAAATGCCGCAAAAAAGGG
     ---------+---------+---------+---------+---------+---------+  5160
ATGAAAGTGGTCGCAAAGACCCACTCGTTTTGTCCTTCCGTTTTACGGCGTTTTTCCC

AATAAGGGCGACACGGAAATGTTGAATACTCATACTCTTCCTTTTCAATATTATTGAAG
     ---------+---------+---------+---------+---------+---------+  5220
TTATTCCCGCTGTGCCTTTACAACTTATGAGTATGAGAAGGAAAAGTTATAATAACTTC

CATTTATCAGGGTTATTGTCTCATGAGCGGATACATATTGAATGTATTAGAAAAATAA
     ---------+---------+---------+---------+---------+---------+  5280
GTAAATAGTCCCAATAACAGAGTACTCGCCTATGTATAACTTACATAAATCTTTTATT

ACAAATAGGGGTTCCGCGCACATTTCCCCGAAAAGTGCCACCTGACGTCTAAGAAACCAT
     ---------+---------+---------+---------+---------+---------+  5340
TGTTTATCCCCAAGGCGCGTGTAAAGGGGCTTTTCACGGTGGACTGCAGATTCTTTGGTA

AATTATCATGACATTAACCTATAAAAATAGGCGTATCACGAGGCCCTTTCGTC
     ---------+---------+---------+---------+---------+  5393
ATAATAGATCTGTAATTGGATATTTTATCCGCATAGTGCTCCGGAAAAGCAG
```

FIG. 14q

DNA ENCODING EIMERIA ANTIGEN

This is a division of application Ser. No. 08/257,392, filed Jun. 9, 1994, now U.S. Pat. No. 5,688,513, which is a Division of Ser. No. 729,099, filed Jul. 12, 1991 (now U.S. Pat. No. 5,403,581).

TECHNICAL FIELD

This application relates to a novel antigen of Eimeria protozoan parasites. This antigen can be used, through various routes of administration, to protect poultry against coccidiosis.

BACKGROUND OF THE INVENTION

Coccidiosis is a disease of poultry caused by intracellular protozoan parasites of the genus Eimeria. The disease is endemic in large, intensive poultry breeding establishments. The estimated cost of control of the disease through chemotherapy exceeds $100 million each year in the United States of America alone. The development of resistance to the known anti-coccidial drugs necessitates a continuing development of new agents, at a time when drug development is becoming increasingly expensive and consumer acceptance of drug residues in food animals is diminishing.

Protective immunity to natural coccidiosis infection has been well documented. Controlled, daily administration of small numbers of viable oocysts for several weeks has been shown to result in complete immunity to a challenge infection of a normally virulent dose [Rose et al., Parasitology 73:25 (1976); Rose et al., Parasitology 88:199 (1984)]. The demonstration of acquired resistance to infection suggests the possibility of constructing a vaccine to induce immunity in young chickens, circumventing the need for chemical coccidiostats. In fact, such a concept has been tested in the Coccivac™ formulation of Sterwin Laboratories, Opelika, Ak.

With a view to producing a coccidiosis vaccine, Murray et al., European Patent Application, Publication No. 167, 443, prepared extracts from sporozoites or sporulated oocysts of *Eimeria tenella* which contain at least 15 polypeptides, many of which were associated with the surface of the sporozoite. Injection of these extracts into chickens reduced cecal lesions following oral inoculation with virulent *E. tenella* sporulated oocysts.

More recently, Schenkel et al., U.S. Pat. No. 4,650,676, disclosed the production of monoclonal antibodies against *E. tenella* merozoites. Using these antibodies, Schenkel et al. identified a number of antigens against which the antibodies were directed. By pre-incubating *E. tenella* sporozoites with these antibodies and then introducing the treated sporozoites into the ceca of chickens, Schenkel et al. were able to show some reduction in cecal lesion scores, compared to untreated sporozoite controls.

Using recombinant DNA methodology, Newman et al. (European Patent Application, Publication No. 164 176) have cloned a gene from the sporozoite stage coding for a 25,000 dalton antigen from *Eimeria tenella*. Sera from chickens immunized by repeated immunization with killed *E. tenella* sporozoites immunoprecipitated this antigen from iodinated sporocyst and sporozoite membrane preparations. More recently, Jenkins [Nucleic Acids Res. 16:9863 (1988)] has described a cDNA encoding a part of a 250,000 dalton merozoite surface protein from *Eimeria acervulina*. The expression product of this cDNA was recognized by antiserum against the organism.

Advances in recombinant DNA technology have made another approach available, i.e. a subunit vaccine. Examples of such subunit vaccines are described e.g. in European Patent Application, Publication Nos. 324 648, 337 589 and 344 808.

SUMMARY OF THE INVENTION

The present invention provides immunogenic polypeptides having the amino acid sequence (1)(SEQ ID NO: 1)

M A K S M L S G I V F A G L V A A A A

S S A N S A A N V S V L E S G P A V Q E

V P A R T V T A R L A K P L L L L S A L

A A T L A A A F L V L Q C F N I I S S N

N Q Q T S V R R L A A G G A C G D E E D

A D E G T S Q Q A S R R R R K P D T P A

A D K Y D F V G G T P V S V T E P N V D

E V L I Q I R N K Q I F L K N P W T G Q

E E Q V L V L E R Q S E E P I L I V A R

T R Q T L E G Y L G S Q A L A Q D G K T

A K E E K V E G G K T H R R Y K V K S S

D P G Y G F P Y T T V L D G V P V G T D

E D G Y V V E V L M K T G P H G G V D M

M T S T A S Q G K F C G V L M D D G K G

N L V D G Q G R K I T A V I G M L T Q P

D T E F R S G P G D D E D D E (SEQ ID NO:1)

which polypeptides are capable of inducing an immune response against Eimeria parasites, for example in chickens. The Eimeria merozoite surface antigen precursor protein described herein has sequences which correspond to sequence (1)(SEQ ID NO: 1).

The preferred polypeptide of the present invention is an immunogenic polypeptide having the amino acid sequence (1)(SEQ ID NO: 1) but lacking the signal peptide sequence at the N-terminus, which signal peptide sequence comprises essentially the first twenty amino acids in the said sequence. The present invention also relates to a functional equivalent polypeptide thereof having an amino acid sequence which is related to the said amino acid sequence by deletions, insertions or substitutions without essentially changing the immunological properties of the said polypeptide.

This invention still further provides a DNA encoding all or part of the Eimeria merozoite surface antigen precursor protein such as the DNA having the nucleotide sequence (A)(SEQ ID NO: 2)

```
ATGGCTAAGTCTATGCTTTCTGGAATTGTTTTTGCTGGTCTTGTTGCTGCTGCAGCG

GCCAGTTCGGCCAACAGCGCCGCCAACGTCTCCGTTTTGGAGAGTGGGCCCGCTGTG

CAGGAAGTGCCAGCGCGCACGGTCACAGCTCGCCTGGCGAAGCCTTTGCTGCTTCTT

TCTGCTCTTGCTGCGACTTTGGCAGCAGCTTTCCTCGTTTTGCAATGCTTCAACATC

ATCTCCAGCAACAACCAGCAAACCAGCGTCAGGAGACTGGCCGCCGGAGGTGCATGC

GGAGATGAGGAAGATGCAGATGAGGGAACTTCACAGCAGGCCAGCCGGAGGAGGAGA

AAACCTGATACCCCTGCAGCAGATAAATACGATTTTGTTGGCGGAACTCCAGTTTCG

GTCACTGAGCCGAATGTTGATGAAGTCCTTATCCAAATTAGAAATAAACAAATCTTT

TTGAAGAACCCATGGACTGGACAAGAAGAACAAGTTCTAGTACTGGAACGACAAAGT

GAAGAACCCATTCTGATTGTGGCGAGGACAAGACAAACACTTGAAGGATATCTTGGT

AGTCAAGCTCTTGCACAGGACGGAAAGACTGCTAAAGAAGAGAAAGTTGAAGGAGGC

AAAACTCACAGAAGATATAAAGTCAAGAGCAGCGACCCAGGATATGGATTCCCATAC

ACCACGGTGCTCGACGGGGTTCCTGTGGGAACAGACGAAGACGGATACGTCGTCGAA

GTTCTTATGAAAACCGGACCCCATGGAGGAGTCGACATGATGACTAGCACAGCATCA

CAAGGAAAATTCTGCGGAGTGCTTATGGATGACGGAAAAGGAAACCTAGTCGATGGA

CAAGGGAGAAAAATTACCGCCGTTATCGGCATGCTAACTCAACCGGATACCGAGTTT

AGAAGCGGACCAGGAGACGACGAGGACGACGAGTGA
``` or parts thereof such as the nucleotide sequence (B) which corresponds to the nucleotide sequence (A)(SEQ ID NO: 2) but lacks essentially the first 60 nucleotides encoding the signal peptide sequence. An ATG codon is preferably added at the beginning of the DNA consisting of a partial sequence of the DNA having the nucleotide sequence (A)(SEQ ID NO: 2)using methods well-known in the art. The present invention still further provides recombinant vectors containing and capable of directing the expression of the said DNA in compatible host organisms, and microorganisms containing such vectors.

This invention still further provides a method for producing the polypeptides defined above, which method comprises:

(a) culturing a microorganism containing a recombinant vector comprising a DNA having a nucleotide sequence encoding the said polypeptide such as the DNA having the nucleotide sequence (A)(SEQ ID NO: 2)or a fragment thereof, such as the nucleotide sequence (B), under conditions in which the DNA sequence or fragment is expressed; and (b) isolating the recombinant polypeptide from the culture.

This invention still further provides vaccines for the protection of subjects against coccidiosis comprising an effective amount of one or more of the polypeptides of the invention and a physiologically acceptable carrier. A preferred subject is fowl or poultry.

This invention still further provides vaccines for the protection of subjects against coccidiosis comprising a recombinant virus containing a DNA sequence encoding a polypeptide of the present invention, which recombinant virus is capable of causing the expression of the said DNA sequence, and a physiologically acceptable carrier.

This invention still further provides a method for the protection of subjects against coccidiosis, which method comprises administering an effective amount of a vaccine of the invention to a subject such as a young fowl which is susceptible to coccidiosis.

The Eimeria polypeptides of the present invention are important vaccine antigens because they were identified by the use of antibodies in the sera of animals that had been immunized against the coccidiosis organism and had developed immunity thereto. Because of this, it is most likely that these polypeptides play a significant role in the protection of poultry against coccidiosis.

BRIEF DESCRIPTION OF THE FIGURES

The invention can be more readily understood by reference to the figures, in which:

FIGS. 1*a*–1*e* show the nucleotide sequence of the 1.2 kb cDNA molecule encoding the Eimeria precursor protein recognized by antigen-select antibodies from rabbit and by chicken immune sera. As can be seen from FIGS. 1A–1C, the nucleotide sequence encoding the said precursor protein is contained between the ATG at nucleotide 68 and the stop codon TM at nucleotide 1013 (coding for 315 amino acids). FIGS. 1A–1C also shows the amino acid sequence of the Eimeria precursor protein predicted from the nucleotide sequence provided. Standard single-letter abbreviations are used to represent nucleotides and amino acids. The meanings of these abbreviations can be found in standard biochemistry textbooks, such as Lehninger, Principles of Biochemistry, 1984, Worth Publishers, Inc., New York, pp. 96, 798.

FIG. 2 shows the results of an SDS PAGE analysis of various Eimeria merozoite proteins. Panel A is an immunoblot of total merozoite proteins probed with control (a) or antigen-select (b) antibodies. The arrow in Panel A indicates the position of a band containing a protein having molecular weight of about 23 kilodaltons. Panel B is an autoradiogram of $^{125}$I-surface-labeled merozoite proteins immunoprecipitated with control (a) or antigen-select (b) antibodies. Panel C shows the complete mixture of products produced by the in vitro translation of merozoite polyA mRNA (c) and translation products which had been immunoprecipitated with antibodies selected using the lambda 5-7 clone (b), antibodies selected using another phage clone which produced proteins reactive with anti-merozoite serum (a) and control antibodies selected from merozoite serum using non-recombinant phage (d). The bands were visualized by fluorography. The positions of molecular weight markers having the indicated molecular weight in kilo Daltons (kDa) are shown to the right of the figure.

FIG. 3 shows the results of Southern Blot analysis of *Eimeria tenella* sporulated oocyst genomic DNA which has been digested with PvuII (lane 1), HincII (lane 2), PstI (lane 3), SphI (lane 4) or SacI (lane 5). The positions of standard DNAs having the indicated sizes in kb are shown to the right of the figure.

FIG. 4 shows a schematic drawing of the plasmid pDS56/RBSII. In this diagram and in FIGS. 6, 8 and 10, the abbreviations and symbols B, E, H, P, S, X and Xb indicate cleavage sites for restriction enzymes BamHI, EcoRI, HindIII, PstI, SalI, XhoI and XbaI, respectively. ▭▨ represents the regulatable promoter/operator element N25OPSN25OP29; ▨ represents ribosomal binding sites RBSII, RBSII(-1) or RBSII(-2) as indicated; ⟶ represents coding regions under control of these ribosomal binding sites; ▥ represents terminators $t_o$ or T1 as indicated; ⬌ represents the region required for DNA replication in *E. coli* (repl.); ▶ represents coding regions for chloramphenicol acetyltransferase (cat), beta-lactamase (bla), lac repressor (lacI) and neomycin phosphotransferase (neo), respectively.

FIGS. 5a–5e display the complete nucleotide sequence of the plasmid pDS56/RBSII. In this sequence, the recognition sequences of the restriction enzymes depicted in FIG. 4 are indicated. The amino acid sequence shown represents the open reading frame under control of ribosomal binding site RBSII.

FIG. 6 is a schematic drawing of the plasmid pDS56/RBSII(-1).

FIGS. 7a–7e display the complete nucleotide sequence of plasmid pDS56/RBSII(-1). In this sequence, the recognition sequences of the restriction enzymes depicted in FIG. 6 are indicated. The amino acid sequence shown represents the open reading frame under control of ribosomal binding site RBSII(-1).

FIG. 8 is a schematic drawing of the plasmid pDS56/RBSII(-2).

FIGS. 9a–9e display the complete nucleotide sequence of plasmid pDS56/RBSII(-2). In this sequence, the recognition sequences of the restriction enzymes depicted in FIG. 8 are indicated. The amino acid sequence shown represents the open reading frame under control of ribosomal binding site RBSII(-2).

FIG. 10 is a schematic drawing of the plasmid pDMI.1.

FIGS. 11a–11d display the complete nucleotide sequence of plasmid pDMI.1. In this sequence, the recognition sequences of the restriction enzymes depicted in FIG. 10 are indicated. The amino acids shown enclose the open reading frames encoding the neomycin phosphotransferase (Met to Phe) and the lac repressor (Met to Gln; please note the reverse orientation of this gene).

FIG. 12 is a schematic drawing of the plasmid pUC8-TK-7.5K. In this diagram and in FIGS. 13 and 15 the abbreviation TK stands for the thymidine kinase gene sequence of vaccinia virus, 7.5K stands for the vaccinia virus 7.5K promoter, lac Z contains regulatory sequences and coding information for a part of the N-terminus of the beta-galactosidase gene, ori represents the region required for DNA replication in *E. coli* and AmpR stands for the coding region of the beta-lactamase gen.

FIGS. 14a–14q shows the complete nucleotide sequence of the recombinant plasmid pR3. The amino acid sequence shown represents the open reading frame under the control of the vaccinia 7.5K promoter.

DESCRIPTION OF THE INVENTION

Figure 2A:
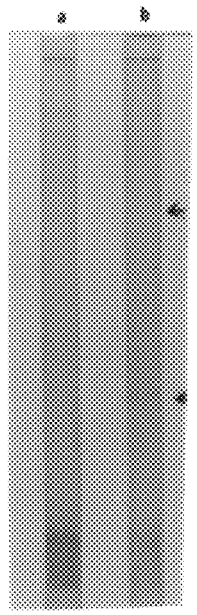

All references cited herein are hereby incorporated in their entirety by reference.

As used herein, the following terms shall have the following meanings:

"Eimeria surface antigen" means a protein having an apparent molecular weight of about 23 kilodaltons in SDS PAGE which is present in the merozoite stage of *Eimeria tenella*. This protein appears to be produced by post-translational processing of the in vivo expression product of a gene having the nucleotide sequence shown in FIGS. 1a–1e.

"Precursor protein" means a protein having an apparent molecular weight of about 33 kilodaltons in SDS PAGE. This protein is believed to be processed by proteolysis in vivo to the Eimeria surface antigen. The nucleotide sequence of a cDNA molecule encoding the precursor protein and the amino acid sequence predicted therefrom are shown in FIGS. 1a–1e.

The term "immunogenic polypeptides having the amino acid sequence (1) which polypeptides are capable of inducing an immune response against Eimeria parasites" means polypeptides capable of eliciting a B-cell and/or T-cell mediated protective immune response against Eimeria parasites comprising the said merozoite surface antigen which corresponds to sequences of the immunogenic polypeptides. The said immunogenic polypeptides may be the mature Eimeria merozoite surface antigen protein free of other Eimeria proteins per se, or fragments of the said Eimeria surface antigen protein which fragments are still capable of specifically binding to antibodies which are present in the sera of animals that are infected with an Eimeria parasite. These polypeptides correspond to T-cell and B-cell epitopes of the Eimeria surface antigen defined above. The polypeptides of the present invention may also be functional equivalents of the said Eimeria merozoite surface antigen protein, which polypeptides have an amino acid sequence related to the amino acid sequence of FIGS. 1a–1e by amino acid substitutions, which substitutions do not substantially alter the immunological activity (i.e., which do not substantially destroy the immunoreactive and/or antigenic determinants).

An example of a fragment is an immunogenic polypeptide which has the amino acid sequence (1)(SEQ ID NO. 1) except that it lacks the first 20 residues, which constitute the signal sequence. Another example is an immunogenic polypeptide which has an apparent molecular weight of 23 kilodaltons on an SDS-polyacrylamide gel. Preferred fragments are as follows:

SNNQQTSV (2)                              (SEQ ID NO: 3)

CGDEEDADEGTSQQASRRRRKPDTPAADK (3)         (SEQ ID NO: 4)

```
                              -continued
PNV (4)                                     (SEQ ID NO:  5)

RNKQIF (5)                                  (SEQ ID NO:  6)

NPWTGQEE (6)                                (SEQ ID NO:  7)

RQSEE (7)                                   (SEQ ID NO:  8)

TRQTLE (8)                                  (SEQ ID NO:  9)

QDGKTAKEEKVEGGKTHRRYKVKSSDPGYG (9)          (SEQ ID NO:10)

TDEDG (10)                                  (SEQ ID NO: 11)

TGPHG (11)                                  (SEQ ID NO: 12)

ASQGK (12)                                  (SEQ ID NO: 13)

DDGKGNLVDGQGRK (13)                         (SEQ ID NO: 14)
                                            and

TQPDTEFRSGPGDDEDDE (14)                     (SEQ ID NO: 15).
```

The fragments of this invention, like the immunogenic polypeptide of sequence (1)(SEQ ID NO. 1), are capable of inducing an immune response against coccidiosis in a subject. Preferred subjects are fowl such as chickens.

Figure 6:
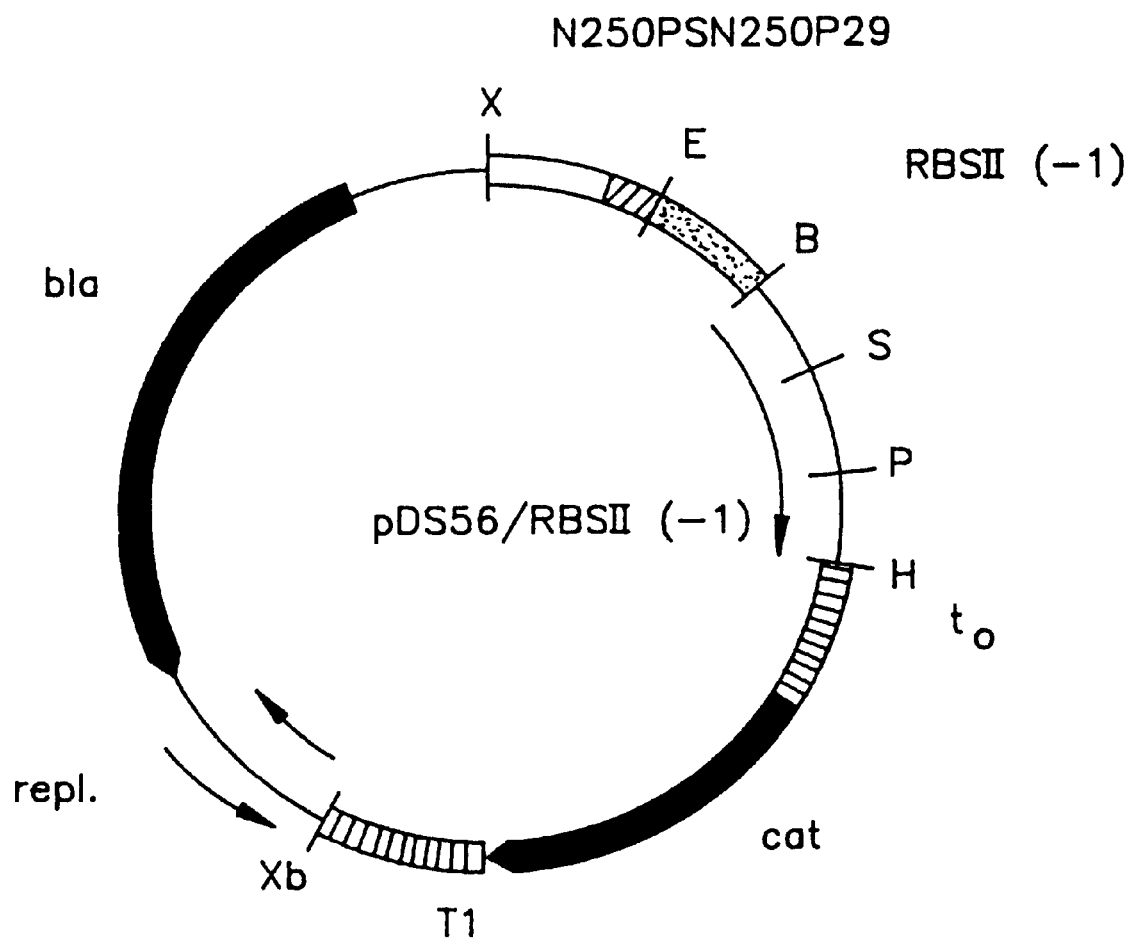

Amino acid substitutions in proteins which do not substantially alter biological and immunological activities have been known to occur and have been described, e.g., by Neurath et al., in "The Proteins", Academic Press, New York (1979), in particular in FIG. 6 at page 14. The most frequently observed amino acid substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and vice versa.

Because of the degeneracy of the genetic code, it will be understood that there are many potential nucleotide sequences (functional equivalents) that could code for the amino acid sequence (1)(SEQ ID NO. 1). It should also be understood that the nucleotide sequences of the DNA sequences and fragments of the invention inserted into vectors may include nucleotides which are not part of the actual structural genes, as long as the recombinant vectors containing such sequence or fragments are capable of directing the production in an appropriate host organism of a polypeptide of the present invention.

DNA sequences encoding the polypeptides which are functional equivalents of the said Eimeria merozoite surface antigen can readily be prepared using appropriate synthetic oligonucleotides in primer-directed site-specific mutagenesis on the exemplary cDNA of this invention (SEQ ID NO. 1), as described by Morinaga et al. [Biotechnology 2:636 (1984)].

Fragments or parts of the Eimeria merozoite surface antigen protein or the DNA encoding it can be produced by enzymatic cleavage of the larger molecules, using restriction endonucleases for the DNA and proteases for the proteins. The fragments of the invention, however, are not limited to the products of any form of enzymatic cleavage but include sub-sequences, the termini of which do not correspond to any enzymatic cleavage points. Such fragments can be made, e.g., by chemical synthesis, using the sequence data provided herein. DNA fragments can also be produced by incomplete complementary DNA (cDNA) synthesis from isolated messenger RNA (mRNA). Protein fragments can also be produced by expressing DNA fragments encoding the protein fragments. Such protein fragments can be useful in the present invention if they contain a sufficient number of amino acid residues to constitute an immunoreactive and/or antigenic determinant. Generally, at least about 7 or 8 residues are needed. As explained below, it may be necessary to couple such fragments to an immunogenic carrier molecule, to make them immunoreactive.

Immune reactivity may include both production of antibodies by B-cells (humoral immunity) and activation of T-cells (cellular immunity). The polypeptides of the subject invention include B-cell antigenic determinants, or epitopes, and T-cell epitopes. Humoral immunity may be demonstrated by the induction of antibody production by B-cells in vivo or in vitro. Cell-mediated immunity may be demonstrated by T-cell activation, for example by increased T-cell protein synthesis, or by the stimulation of B-cells by activated T-cells. Assays for both types of immunity are well known in the art.

The polypeptides of the present invention can be made by methods known in the art such as by recombinant DNA methodology, chemical synthesis or by isolation from Eimeria preparations. When produced in accordance with this invention, the polypeptide of sequence 1(SEQ ID NO.1) and fragments thereof are substantially free of other proteins produced by Eimeria parasites.

DNA needed to make the proteins of this invention could be chemically synthesized, using the nucleotide sequence information provided in (SEQ ID NO. 2) and in the figures. Such chemical synthesis can be carried out using any of the known methods such as the phosphoramidite solid support method of Matteucci et al. [J. Am. Chem. Soc. 103:3185 (1981)].

Alternatively, cDNA can be made from Eimeria mRNA. Messenger RNA can be isolated from Eimeria merozoites using standard techniques. These mRNA samples can be used to produce double-stranded cDNA as described by Maniatis et al. [Molecular Cloning: A Laboratory Manual, 1982, Cold Spring Harbor Laboratory, Cold Spring Harbor, N.Y.]. This cDNA can then be inserted into an appropriate cloning vector which can be used to transform *E. coli*, to produce a cDNA library.

The cDNA library can then be screened using the cloned gene of this invention, or fragments thereof, as probes. Such gene or fragments can be radiolabeled, e.g., by nick-translation using Pol I DNA polymerase in the presence of the four deoxyribonucleotides, one of which contains $^{32}$p in the alpha position (Maniatis et al., supra, p. 109), for use as probes. The probes may also be prepared by oligonucleotide synthesis based on the known sequence of the cDNA of the Eimeria surface antigen.

Although *Eimeria tenella* was used as an mRNA source in the Examples below, the cloned genes from this species can be used as probes to isolate genes from other species of Eimeria, due to DNA sequence homology among the various species.

Once identified and isolated, the Eimeria DNAs of this invention are inserted into an appropriate expression vehicle or vector which contains the elements necessary for transcription and translation of the inserted gene sequences. Useful cloning vehicles may consist of segments of chromosomal, nonchromosomal and synthetic DNA sequences such as various known bacterial plasmids, virus DNA, such as phage DNA, combinations of plasmids and viral or phage DNA such as plasmids which have been modified to employ phage DNA or other expression control sequences, or yeast plasmids. Specific cloning vehicles which could be used include but are not limited to the pEV-vrf plasmids (pEV-vrfl, −2 and −3 which are described in Crowl et al., Gene 38:31 (1985)); SV40; adenovirus; yeast; lambda gt-WES-lambda B; Charon 4A and 28; lambda-gt-2; M13-derived vectors such as pUC8, 9, 18 and 19, pBR313, 322 and 325; pAC105; pVA51; pACY177; pKH47; pACYC184; pUB110; pMB9; colE1; pSC101; pML21; RSF2124; pCR1 or RP4; fowlpox; vaccinia or a member of the herpesvirus family.

The insertion of the Eimeria genes into a cloning vector is easily accomplished when both the genes and the desired cloning vehicle have been cut with the same restriction enzyme or enzymes, since complementary DNA termini are thereby produced. If this cannot be accomplished, it may be necessary to modify the cut ends that are produced by digesting back single-stranded DNA to produce blunt ends, or by achieving the same result by filling in the single-stranded termini with an appropriate DNA polymerase. In this way, blunt-end ligation with an enzyme such as T4 DNA ligase may be carried out. Alternatively, any site desired may be produced by ligating nucleotide sequences (linkers) onto the DNA termini. Such linkers may comprise specific oligonucleotide sequences that encode restriction site recognition sequences. The cleaved vector and the Eimeria genes or fragments may also be modified by homopolymeric tailing, as described by Morrow [Methods in Enzymology 68:3 (1979)].

Many of the cloning vehicles that may be used in this invention contain one or more marker activities that may be used to select for desired transformants, such as ampicillin and tetracycline resistance in pBR322, ampicillin resistance and beta-galactosidase activity in pUC8, and ampicillin resistance in the pEV-vrf plasmids. Selection of host cells into which such vectors have been inserted is greatly simplified when the host cells otherwise lack the activities contributed by the vectors.

It should be understood that the nucleotide sequences of the Eimeria genes inserted at a selected site in a cloning vehicle may include nucleotides which are not part of the actual structural genes. Alternatively, the genes may contain only part of the complete wild-type gene. All that is required is that the gene fragments after insertion into a cloning vehicle are capable of directing the production in an appropriate host organism of a polypeptide or protein having at least one immunoreactive and/or antigenic determinant of the Eimeria surface antigen. Thus, the recombinant vectors comprising a DNA having a nucleotide sequence encoding a protein of the present invention may be prepared by:

(a) inserting a DNA having a nucleotide sequence encoding the said protein into a vector;

(b) replicating the said vector in a microorganism; and (c) isolating the recombinant vector from the microorganism.

The selection of an appropriate host organism is affected by a number of factors known in the art. These factors include, for example, compatibility with the chosen vector, toxicity of proteins encoded by the hybrid plasmid, ease of recovery of the desired protein, expression characteristics, biosafety and costs. A balance of these factors must be considered, and it must be understood that not all hosts will be equally effective for expression of a particular recombinant DNA molecule.

Suitable host microorganisms which can be used in this invention include but are not limited to plant, mammalian or yeast cells and bacteria such as *Escherichia coli, Bacillus subtilis, Bacillus stearothermophilus* and Actinomyces. *Escherichia coli* strain MC1061, which has been described by Casadaban et al. [J. Mol. Biol. 138:179 (1980)], can be used, or any other strain of *E. coli* K-12 containing the plasmid pRK248clts. Plasmid pRK248clts for use in other *E. coli* K-12 strains is described by Bernhard et al. [Meth. of Enzymol. 68:482 (1979)] and is also available from the American Type Culture Collection under accession No. ATCC 33766. The *E. coli* strain MC1061 is commercially available e.g. from CLONTECH Laboratories, Inc., Palo Alto, Calif., USA and is also available from the American Type Culture Collection under accession No. ATCC 53338. Plasmids pDMI.1, pDS56/RBSII, −1 or −2 for use in *E. coli* strain M15 are described infra.

Transfer of the recombinant cloning vector into the host cell may be carried out in a variety of ways. Depending upon the particular vector/host cell system chosen, such transfer may be effected by transformation, transduction, transfection or electroporation. Once such a modified host cell is produced, the cell can be cultured and the protein expression product may be isolated from the culture.

Transformant clones producing the precursor protein of the Eimeria surface antigen are identified by screening with serum from animals immunized against glutaraldehyde-fixed sporozoites or merozoites of *E. tenella*. In the examples below, rabbit anti-merozoite serum was used for screening and characterizing the gene product. Parallel immunologic screening with immune chicken serum resulted in the independent isolation of the cDNA encoding the merozoite surface antigen precursor.

The specificity of the antisera used for immunological screening or immunoprecipitation can be increased by using a variation of the antibody select method of Hall et al. [Nature 311:379 (1984)]. In this method, which is described more fully below, antibodies that are specific for Eimeria proteins made by the clones are adsorbed out on filters.

The detection of Eimeria antigen producing clones can be achieved by the use of well known standard assay methods, including immunoprecipitation, enzyme-linked immunoassay (ELISA) and radioimmunoassay techniques which have been described in the literature [see, e.g., Kennet et al. (editors), Monoclonal Antibodies and Hybridomas: A New Dimension in Biological Analyses, 1980, Plenum Press, New York, pp. 376–384].

Recombinant vectors comprising a DNA encoding a variant polypeptide of the Eimeria surface antigen of the present invention may be prepared using methods well-known in the art, e.g. by site-specific mutagenesis.

Large amounts of the recombinant Eimeria polypeptides of the present invention may be produced by growing the transformed microorganisms obtained in this way in a fermentation broth comprising the necessary nutrients under conditions suitable for expression of the recombinant DNA. As produced in *E. coli*, the recombinant Eimeria polypeptides are usually present in the cytoplasm or in inclusion bodies of the bacteria. To free the proteins it is thus necessary to disrupt the outer membrane of the bacteria. This is accomplished by sonication, or by other mechanically disruptive means, such as by using a French pressure cell or Gaulin homogenizer [Charm et al., Meth. Enzymol. 22, 476–556 (1971)].

Cell disruption can also be accomplished by chemical or enzymatic means. Since divalent cations are often required for cell membrane integrity, treatment with appropriate chelating agents such as EDTA or EGTA might prove sufficiently disruptive to facilitate the leakage of the proteins from the cells. Similarly, enzymes such as lysozyme have been used to achieve the same result. That enzyme hydrolyzes the peptidoglycan backbone of the cell wall.

Osmotic shock can also be employed. Briefly, this can be accomplished by first placing the cells in a hypertonic solution which would cause them to lose water and shrink. Subsequent placement in a hypotonic "shock" solution would then lead to a rapid influx of water into the cells with an expulsion of the desired proteins.

Once freed from the cells, the Eimeria proteins may be concentrated by precipitation with salts such as sodium or ammonium sulfate, ultrafiltration or other methods well known to those skilled in the art. Further purification could be accomplished by conventional protein purification techniques including but not limited to gel filtration, ion-exchange chromatography, preparative disc-gel or curtain electrophoresis, isoelectric focusing, low temperature organic solvent fractionation, or countercurrent distribution. Purification can also be carried out by immunoaffinity chromatography.

Specific methods for purifying Eimeria proteins from the organisms are known in the art (see e.g., Newman et al., European Patent Application, Publication No. 164 176).

The proteins of this invention or fragments thereof can also be chemically synthesized by a suitable method such as by exclusive solid phase synthesis, partial solid phase methods, fragment condensation or classical solution synthesis. Solid phase synthesis as described by Merrifield [J. Am. Chem. Soc. 85:2149 (1963)] is preferred.

Such synthesis is carried out with amino acids that are protected at the alpha-amino-terminus. Trifunctional amino acids with labile side-chains are also protected with suitable groups which will prevent a chemical reaction from occurring at that site during the assemblage of the peptide. The alpha-amino protecting group is selectively removed to allow subsequent reaction to take place at the amino-terminus. The conditions for the removal of the alpha-amino protecting group do not cause deprotection of the side-chain protecting groups.

The alpha-amino protecting groups are those known to be useful in the art of stepwise synthesis of peptides. Included are acyl type protecting groups (e.g., formyl, trifluoroacetyl, acetyl), aromatic urethane type protecting groups (e.g., benzyloxycarbonyl (Cbz) and substituted benzyloxycarbonyl), aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). The preferred protecting group is Boc. The side-chain protecting groups for Tyr include tetrahydropyranyl, tert.-butyl, triyl, benzyl, Cbz, 4-Br-Cbz and 2,6-dichlorobenzyl. The preferred side-chain protecting group for Tyr is 2,6-dichlorobenzyl. The side-chain protecting groups for Asp include benzyl, 2,6-dichlorobenzyl, methyl, ethyl and cyclohexyl. The preferred side-chain protecting group for Asp is cyclohexyl. The side-chain protecting groups for Thr and Ser include acetyl, benzoyl, trityl, tetrahydropyranyl, benzyl, 2,6-dichlorobenzyl and Cbz. The preferred protecting group for Thr and Ser is benzyl. The side-chain protecting groups for Arg include nitro, Tos, Cbz, adamantyloxycarbonyl or Boc. The preferred protecting group for Arg is Tos. The side-chain amino group of Lys may be protected with Cbz, 2-ClCbz, Tos or Boc. The 2-Cl-Cbz group is the preferred protecting group for Lys. The selection of the side-chain protecting group is based on the following: The side-chain protecting group remains intact during coupling and is not split off during the deprotection of the amino-terminus protecting group or during coupling conditions. The side-chain protecting group must be removable upon the completion of the synthesis of the final peptide, using reaction conditions that will not alter the target peptide.

Solid phase synthesis is usually carried out from the carboxy-terminus by coupling the alpha-amino protected (side-chain protected) amino acid to a suitable solid support. An ester linkage is formed when the attachment is made to a chloromethylated or hydroxymethyl resin and the resultant target peptide will have a free carboxyl group at the C-terminus. Alternatively, a benzhydrylamine or p-methylbenzhydrylamine resin is used in which case an amide bond is formed and the resultant target peptide will have a carboxamide group at the C-terminus. These resins are commercially available and their preparation is described by Stewart et al., "Solid Phase Peptide Synthesis" (2nd Edition, Pierce Chemical Co., Rockford, Ill., 1984).

The C-terminal amino acid, Arg, protected at the side-chain with Tos and at the alpha-amino function with Boc is coupled to the benzhydrylamine resin using various activating agents including dicyclohexylcarbodiimide (DCC), N,N'-diisopropylcarbodiimide and carbonyldiimidazole. Following the attachment to the resin support the alpha-amino protecting group is removed by using trifluoroacetic acid (TFA) or HCl in dioxane at a temperature between 0° and 25° C. Dimethylsulfide is added to the TFA after the introduction of methionine (Met) to suppress possible S-alkylation. After removal of the alpha-amino protecting group, the remaining protected amino acids are coupled stepwise in the required order to obtain the desired peptide sequence.

Various activating agents can be used for the coupling reactions including DDC, N,N'-diisopropylcarbodiimide, benzotriazol-1-yl-oxy-tris-(dimethylamino)-phosphonium hexafluorophosphate (BOP) and DCC-hydroxybenzotriazole (HOBt). Each protected amino acid is used in excess (>2.5 equivalents), and the couplings are usually carried out in DMF, $CH_2Cl_2$ or mixtures thereof. The extent of completion of the coupling reaction is monitored at each stage by the ninhydrin reaction as described by Kaiser et al. [Anal. Biochem. 34:595 (1970)]. In cases where incomplete coupling is determined the coupling reaction is repeated. The coupling reactions can be performed automatically on a Vega 250, Applied Biosystems synthesizer or other commercially available instrument. After the entire assemblage of the target peptide, the peptide-resin is deprotected with TFA/dithioethane and then cleaved with a reagent such as liquid HF for 1–2 hours at 0° C. which cleaves the peptide from the resin and removes all side-chain protecting groups.

Side-chain to side-chain cyclization on the solid support requires the use of an orthogonal protection scheme which enables selective cleavage of the side-chain functions of the acidic amino acids (e.g., Asp) and the basic amino acids (e.g., Lys). The 9-fluorenylmethyl (OFm) protecting group for the side-chain of Asp and the 9-fluorenylmethoxycarbonyl (Fmoc) protecting group for the side-chain of Lys can be used for this purpose. In these cases the side-chain protecting groups of the Boc-protected peptide-resin are selectively removed with piperidine in DMF. Cyclization is achieved on the solid support using various activating agents including DCC, DCC/HOBt or BOP. The HF reaction is carried out on the cyclized peptide-resin as described above.

Purification and screening of the synthetic proteins can be carried out as described above for the recombinantly produced proteins.

Eimeria proteins can also be recovered from the organisms, from extracts of membrane proteins. Such methods can produce the complete, wild-type proteins. Monoclonal antibodies for this purpose can be produced as described by Köhler and Milstein [Nature 256:495 (1975)], using synthetic or natural Eimeria proteins as the antigen. These methods can be used to purify the 23 kd Eimeria surface antigen of this invention.

One or more of the polypeptides of this invention can be formulated into vaccines comprising the polypeptides and a physiologically acceptable carrier. Suitable carriers include, e.g., 0.01 to 0.1 M phosphate buffer of neutral pH or physiological saline solution.

Enhanced immunity against coccidiosis can be produced in one of two ways. First, an adjuvant or immunopotentiator can be added to the vaccine. Secondly, the proteins of the invention can be presented to a subject that is to be immunized in a larger form, either as a cross-linked complex of conjugated to a carrier molecule.

Suitable adjuvants for the vaccination of subjects include but are not limited to Adjuvant 65 (containing peanut oil, mannide monooleate and aluminum monostearate); mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The proteins could also be administered following incorporation into liposomes or other microcarriers.

Incorporation into liposomes or other microcarriers provides a means by which the release of the vaccines can be sustained over a prolonged period of time. A pump such as an Alza osmotic pump could be used for the same purpose.

The immunogenicity of the polypeptides of the invention, especially the smaller fragments, can be enhanced by cross-linking or by coupling to an immunogenic carrier molecule (i.e., a macromolecule having the property of independently eliciting an immunological response in a host animal, to which the proteins and protein fragments of the invention can be covalently linked). Cross-linking or conjugation to a carrier molecule may be required because small protein fragments sometimes act as haptens (molecules which are capable of specifically binding to an antibody but incapable of eliciting antibody production, i.e., they are not immunogenic). Conjugation of such fragments to an immunogenic carrier molecule renders the fragments immunogenic through what is commonly known as the "carrier effect".

Suitable carrier molecules include, e.g., proteins and natural or synthetic polymeric compounds such as polypeptides, polysaccharides, lipopolysaccharides etc. A useful carrier is a glycoside called Quil A, which has been described by Morein et al. [Nature 308:457 (1984)]. Protein carrier molecules are especially preferred, including but not limited to mammalian serum proteins such as keyhole limpet hemocyanin, human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the Eimeria proteins are to be elicited.

Covalent coupling to the carrier molecule can be carried out using methods well known in the art, the exact choice of which will be dictated by the nature of the carrier molecule used. When the immunogenic carrier molecule is a protein, the proteins or fragments of the invention can be coupled, e.g., using water soluble carbodiimides such as dicyclohexylcarbodiimide, or glutaraldehyde.

Coupling agents such as these can also be used to cross-link the proteins and fragments to themselves without the use of a separate carrier molecule. Such cross-linking into protein or protein fragment aggregates can also increase immunogenicity.

Administration of an effective amount of the vaccines of this invention can protect against coccidiosis, for example as caused by E. tenella infection or infection by other Eimeria species. Monoclonal antibodies against the E. tenella antigens cross-react with E. acervulina and E. maxima in vitro. Preferred subjects are poultry such as chickens, but other subjects are within the scope of this invention. In accordance with this invention, any effective amount of vaccine may be used. The effective amount may be determined by routine experimentation using methods described below. An effective amount of the polypeptides and fragments of this invention that ranges from about 5 to about 50 micrograms/kg of body weight of the vaccinated subject is preferred, in particular a dose of about 25–50 μg/kg. Initial vaccinations are preferably followed by booster vaccinations given from one to several weeks later. Multiple boosters may be administered. The dosages of such boosters generally range from about 5 to 50 μg/kg, preferably about 20–50 μg/kg. Standard routes of administration can be used such as subcutaneous, intradermal, intramuscular, oral, anal or in ovo administration (direct injection into embryos). Single or multiple booster vaccinations may be followed by an induced minor coccidiosis infection, which can enhance protection.

The presentation of the coccidial antigens of the invention to the immune systems of subjects, for example fowl, can also be achieved by cloning genes coding for the antigens into bacteria (e.g., E. coli or Salmonella) or into viruses (e.g., poxviruses or herpesviruses) and administering the live vector system or, when appropriate, its inactivated form to the subjects, orally, by injection or by other commonly used routes. Carbit et al. [in: Vaccines, 1987, Cold Spring Harbor Laboratory, pp. 68–71] have described the use of E. coli, while Clements [Pathol. Immunopathol. Res. 6:137 (1987)] has described the use of Salmonella. Moss et al. [Ann. Rev. Immunol. 5:305 (1987)] have reviewed the use of viral vector systems employing recombinant poxviruses.

One kind of poxvirus, vaccinia virus, can be used to test the delivery of coccidial antigens in cell culture and in animals. Fowlpox virus is another poxvirus carrier that can be used for performing the present invention. For analytical studies, vaccinia virus has been found to be more practical than fowlpox virus. This is because vaccinia virus multiplies more rapidly than the avian virus and has a host range that is not restricted to chicken cells. Large amounts of heterologous DNA can be inserted into the vaccinia viral genome without inhibiting viral maturation and infectivity [Smith et al., Gene 25:21 (1983)]. The insertion and expression of multiple heterologous genes using the virus elicits antibody production against expressed antigens in infected animals [Perkus et al., Science 229:981 (1985)].

The techniques used to produce recombinant vaccinia viruses can be readily adapted by routine procedures to fowlpox or herpesvirus systems. A recombinant virus comprising a DNA having a nucleotide sequence encoding a protein of the present invention may be prepared by:

(a) inserting a DNA having a nucleotide sequence encoding the said protein into the genome of a virus without inhibiting viral maturation and infectivity;

(b) amplifying the said recombinant virus in a cell culture; and (c) purifying the recombinant virus from the culture.

The use of recombinant viruses as carriers in vaccines against coccidiosis is especially advantageous in that vaccinated fowl develop immunity against both the coccidial antigen and the viral carrier (i.e., such vaccines are bivalent). The utility of such vaccines can be further enhanced by inserting additional genes into the carrier virus. For example, parts of the Newcastle disease viral genome can be inserted together with a coccidial antigen gene into a fowlpox virus, thereby conferring immunity against Newcastle disease, coccidiosis and fowlpox, all with a single vaccine.

The administration of the live vector vaccines of the invention can be carried out by numerous methods well known in the art. For example, the "stick" method commonly used to vaccinate poultry against fowlpox virus can be used. This method consists of sticking or pricking the skin of the wing web with a sharp needle dipped into the vaccine. The needle usually has an eye near the tip like a sewing machine needle which carries a drop of vaccine. Alternatively, the live vaccines can be injected subcutaneously or intradermally into the wing web or any other site.

The recombinant live vector vaccines can also be added to drinking water or even sprayed over subjects, such as chicks, that are to be vaccinated. They can also be administered in feed, preferably after protective encapsulation [Balancou et al., Nature 322:373 (1986)], or in ovo. In the latter method, the viral vaccines are injected directly into embryos, in particular, chicken embryos. [Sharma, Avian Dis. 25:1155 (1985)].

All references cited herein are hereby incorporated by reference in their entirety.

Unless otherwise specified, percentages given below for solids in solid mixtures, liquids in liquids, and solids in liquids are on a wt/wt, vol/vol and wt/vol basis, respectively. Furthermore, unless otherwise specified, the suppliers of reagents and instruments mentioned below are not meant to be mandatory. The skilled person is in a position to select similar reagents or instruments from other suppliers.

EXAMPLE 1

Purification of Merozoites

Merozoites of *E. tenella* were harvested from the ceca of 50 infected chickens (3 week old Hubbard Cross; Avian Services, Frenchtown, N.J., USA) 5 days after infection with 50,000 of the above sporulated oocysts/bird. Similar chickens from other sources may be used. The ceca were removed and washed with phosphate buffered saline (PBS) for 15 minutes on a magnetic stirrer. The epithelial debris was partially removed by low speed centrifugation (50×g), and the crude merozoites were recovered by centrifugation at 2,000 x g at 4° C. for 10 minutes. The pellet was resuspended in Lysing Buffer (8.29 g/l $NH_4Cl$, 0.372 g/l $Na_2EDTA$, 1.0 g/l $KHCO_3$, pH 7.6) and incubated on ice for 30 minutes. The merozoites were collected by centrifugation, washed once in PBS and passed over a column containing 1.0 g of spun nylon fiber (Scrub Nylon Fiber, Fenwall Laboratories, Deerfield, Ill.) in a separatory funnel. The merozoites were collected by centrifugation as before and frozen on dry ice for RNA isolation, or further purified in diethylaminoethyl cellulose (DEAE, Whatman DE52, Whatman Bio Systems, Inc., Clifton, N.J., USA) for Western blot analysis.

For purification in DEAE cellulose, approximately $1\times10^9$ merozoites were applied in PBS to a 10-ml bed volume column and eluted with PBS. The merozoites were recovered in the first 100 ml of flow-through, essentially free of red blood cells and other cellular debris.

Immunoprecipitation of $^{125}$I-Labeled Surface Proteins

The surface proteins of purified merozoites were labeled with $^{125}$I by the IODOGEN™ method (Pierce Chemical Co.) or by use of IODOBEADS™ (Pierce Chemical Co.). For the latter procedure, 4 IODOBEADS™ were washed 3 times with 0.2 M sodium phosphate, pH 7.5, and 1–3 mCi of $^{125}$I-Na were added and incubated for 5 minutes at room temperature. Purified merozoites ($3\times10^8$) in 200 ml of PBS, pH 7.0, were added to the reaction vial, and the incubation was continued for 15 minutes. At the end of the incubation, phenylmethanesulfonyl fluoride (PMSF) was added to a final concentration of 5 mM.

The labeled merozoites were recovered from the incubation mixture by centrifugation at 12,000×g for 30 seconds and solubilized in 1 ml of either 2% sodium dodecysulfate (SDS) or 1% Triton X-100 in PBS, pH 7.0. Insoluble material was removed by centrifugation for 3 minutes at 12,000×g. The solubilized proteins were dialyzed against 3 liters of PBS, pH 7.0, at 4° C. using a 3,500 molecular weight cutoff membrane to remove any residual free $^{125}$I. The $^{125}$I-labeled proteins (typically about $1.5\times10^8$ cpm incorporated into protein) were stored at 4° C. until used. The TCA precipitable radioactivity was typically in excess of 95% of the total radioactivity.

Rabbit antiserum against glutaraldehyde-fixed merozoites was prepared as follows:

Approximately $1\times10^9$ purified merozoites were suspended in 1% glutaraldehyde in PBS and incubated at room temperature for 5 minutes. The fixed parasites were harvested by centrifugation at 2000×g for 5 minutes, washed three times with PBS and resuspended in 1 ml PBS. New Zealand white rabbits were given multiple intradermal injections in the skin of the back with a total of 0.5 ml of the fixed parasite solution emulsified with 0.5 ml complete Freund's adjuvant. Rabbits received two booster injections containing the same parasite protein in incomplete Freund's adjuvant at two week intervals. Blood was harvested from the ear vein two weeks after the last boost and serum containing antibodies was obtained by centrifugation of coagulated blood samples for 15 minutes at 2500×g.

Samples of labeled proteins for immunoprecipitation (5 ml, containing $5\times10^5$ cpm) were diluted into 100 ml of IP buffer (0.25% NP-40, 20 mM Tris-HCl, pH 7.5, 0.15 M NaCl), pre-cleared by incubation for 20 minutes on ice with 5 mg of Staph-A protein (Pansorbin™, Calbiochem Corp., San Diego, Calif.), and incubated for several hours at 4° C. with 5–10 ml of the rabbit anti-merozoite serum. The antibody complexes were collected by a second incubation with 5 mg of Staph-A protein for 20 minutes on ice and centrifuged for 15 seconds in an Eppendorf centrifuge. The pellets were washed 4 times with IP buffer, and the labeled proteins immunoprecipitated by the antibody reagent were eluted from the complex by heating to 100° C. for 5 minutes in SDS gel sample buffer (65 mM Tris pH 6.8, 0.5% SDS, 5% beta-mercaptoethanol, 10% glycerol, 0.1% bromophenol blue). SDS polyacrylamide gelelectrophoresis (SDS PAGE) was carried out as described by Laemmli [Nature 227:680 (1970)].

Results obtained with the rabbit antiserum were confirmed using immune chicken serum prepared as follows:

Chickens were immunized by repeated infection with viable sporulated oocysts of *E. tenella* (100,000 oocysts, given 3 times at 2 week intervals). Blood was harvested by cardiac puncture and the serum containing antibodies was separated from coagulated debris following centrifugation at 2500×g for 5 minutes.

Comparison studies were carried out in which both the anti-merozoite rabbit serum and the immune chicken serum were used to immunoprecipitate $^{125}$I-surface-labeled Eimeria merozoite proteins and the in vitro products of the translation of poly(A)-containing merozoite RNA. The precipitated proteins were then subjected to SDS PAGE and visualized by fluorography using standard fluorography techniques and reagents.

These studies showed that the many proteins from both sources were precipitated by both sera. Thus, either serum could be used to screen genetic recombinants expressing Eimeria proteins. For convenience, the rabbit anti-merozoite serum was used first in the screening procedures described below. However, immune chicken serum was used in parallel screening of the cDNA library as described below. This was essential for the identification of proteins likely to be important in the immune response to the infectious organism, because only the chicken serum was produced in response to challenge with live organisms. Only the immunized chickens were demonstrably resistant to such organisms.

To increase the specificity of the rabbit anti-merozoite serum for Eimeria proteins, antibody select was carried out on the sera essentially as described by Hall et al. [Nature 311:379 (1984)]. Briefly, antibodies specific for the precursor protein expressed by a recombinant phage clone (see below) were purified from the rabbit anti-merozoite serum as follows.

The positive phage was plated to high density and grown at 42° C. for 3.5 hours. Expression of the fusion protein was induced by overlayering the plate with a nitrocellulose filter saturated with 10 mM isopropylthiogalactoside (IPTG), and incubation was continued at 37° C. for 6–8 hours. The antigen-loaded filters were washed in TBS (20 mM Tris-HCl, pH 8.0, 150 mM NaCl) and incubated for 8–10 hours at 4° C. with excess anti-merozoite serum which had been pre-absorbed with the E. coli host bacteria. The filters were washed 3 times with TBS to remove non-specific antibodies.

The antibodies specifically bound to the fusion protein on the filters were eluted with 2.0 ml of 0.1 M glycine, pH 2.6, 0.15 M NaCl (15 minutes at 20° C). The eluted antibodies were neutralized immediately with an equal volume 0.1 M Tris-HCl, pH 8.0. The selected antibodies (hereinafter referred to as "antigen-select antibodies") were then used in the immunoprecipitation of surface-labeled merozoites or in vitro translation products, or as probes in Western blots of whole merozoite protein. Control sera were prepared using non-recombinant phage in the antigen-select procedure.

Figure 2B:
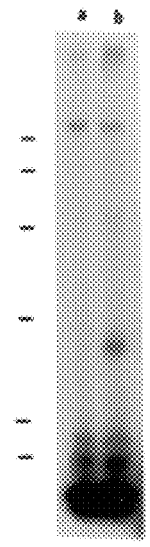
Figure 2C:
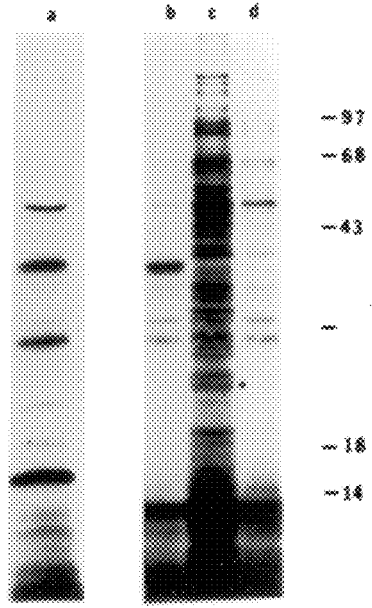

The results of Western blot and immunoprecipitation analyses using the antigen-select antibodies are shown in FIG. 2. The products of the immunoprecipitation of labeled proteins were visualized by fluorography as described by Bonner et al. [Eur. J. Biochem, 46:83 (1974)]. Numbers to the right of the figure show the positions of molecular weight marker proteins having the indicated sizes in kilodaltons.

Panel A of FIG. 2 shows an immunoblot of total merozoite proteins probed with control (a) or antigen-select antibodies (b). Panel B shows [125]I-surface-labeled merozoite proteins that had been immunoprecipitated with control (a), or antigen-select (b) antibodies.

Isolation and In vitro Translation of Merozoite mRNA

Frozen merozoite pellets containing $1 \times 10^9$ to $1 \times 10^{10}$ organisms were thawed into 10 ml of TEL/SDS buffer (0.2 M Tris-HCl, 0.1 M LiCl, 25 mM EDTA, 1% (w/v) sodium dodecyl sulfate (SDS), pH 8.8) containing 1 mM dithiothreitol (DTT) and 300 units of RNasin (Promega Biotec, Madison, Wis.) and homogenized with 10–12 strokes in a teflon-coated tissue homogenizer. Insoluble debris was separated by centrifugation in the cold at 3,000×g. The supernatant fluid was extracted twice with phenol:chloroform:isoamyl alcohol (24:24:1,v/v) which had been equilibrated with the TEL buffer.

The aqueous phase was digested with 100 mg/ml proteinase K at 37° C. for 30 minutes and reextracted with an equal volume of phenol:chloroform (1:1), and the nucleic acid was precipitated with two volumes of ethanol for 1 hour on dry ice, or overnight at −20° C. The pellet, after centrifugation at 10,000×g for one hour, was resuspended in TE (10 mM Tris-HCl, pH 7.5, 2 mM EDTA) and spun through a 4 ml CsCl cushion (5.7 M CsCl, 0.1 M EDTA) at 150,000×g for 20 hours at 15° C. The RNA pellet was reprecipitated from 0.2 M potassium acetate with 2.5 volumes of ethanol. This total RNA was passed once over oligo-dT cellulose to enrich for poly(A)$^+$ RNA, as described by Maniatis, supra, page 197. A typical yield of 1.9 mg of total RNA from $5 \times 10^9$ merozoites contained approximately 20 μg of poly(A)$^+$ RNA.

Between 0.1 and 0.5 μg of mRNA was used to program in vitro protein synthesis in a nuclease-treated rabbit reticulocyte lysate (Amersham Corp., Arlington Heigths, Ill., USA or Promega Biotec) supplemented with 10–20 mCi of $^{35}$S-methionine per 20 ml of reaction mixture. The in vitro translation products were analyzed by immunoprecipitation followed by SDS PAGE and visualized by fluorography as described above, with the results shown in FIG. 2, Panel C.

Lane c of Panel C shows the complete mixture of products programmed by the poly (A)-containing merozoite RNA. Lane b, a and d show translation products immunoprecipitated by antibodies selected by a recombinant phage clone designated lambda 5-7 (see below; this clone expresses a gene encoding the 33 kilodalton Eimeria precursor protein), another phage clone reacting with anti-merozoite serum and a non-recombinant lambda gt11 clone, respectively.

It should be noted that a major protein having an apparent molecular weight of about 33 kilodaltons can be seen in lanes a and b, FIG. 2, Panel C. This protein is not present in the lane containing total merozoite proteins probed with antigen-select antibodies (Panel A, lane b), but a 23 kilodalton band can be seen in this gel (Panel A, lane b, arrow). A protein of 23 kilodaltons was also immunoprecipitated by the antigen-select antibodies from [125]I-labelled merozoite proteins as shown in FIG. 2, panel B, lane b. These observations together suggest that the 33 kilodalton precursor protein may be processed by proteolytic cleavage in mature merozoites to the 23 kilodalton surface antigen.

Preparation of a Merozoite cDNA Expression Library

Double-stranded cDNA was synthesized from 6 μg of the merozoite poly (A)$^+$RNA as described by Gubler et al., Gene 25:263 (1983), using reverse transcriptase (BRL, Gaithersburg, Md., USA) to elongate from an oligo(dT) primer and RNase H (BRL) and E. coli DNA polymerase I (New England Biolabs, Beverly, Mass., USA) to synthesize the complementary strand. The double-stranded cDNA was then blunt-ended with T4 DNA polymerase (BRL), and Eco RI linkers (GGAATTCC, Collaborative Research Inc., Bedford, Mass., USA) were added after treatment with EcoRI methylase (New England Biolabs), following the manufacturers' protocols.

Following digestion with EcoRI, the cDNAs were fractionated in Biogel A-50M to remove excess linker molecules and cDNAs smaller than approximately 300 bp, as described by Huynh et al., infra. The cDNA was then concentrated by precipitation from ethanol.

A library was prepared in λgt11 (Stratagene Cloning Systems, San Diego, Calif.) as described by Huynh et al., in D. Glover (ed.), DNA Cloning Vol. I: A Practical Approach, 1985, IRL Press, Washington, D.C., USA, pp. 49–78. The EcoRI cDNA fragments were ligated to EcoRI digested, dephosphorylated λgt11 arms (Stratagene Cloning Systems), and the resulting DNA was packaged into phage with the Gigapack™ kit (Stratagene Cloning Systems), following the manufacturers protocol.

The resulting library was amplified by plating on Y1088 host cells. The percentage of recombinants was estimated from the ratio of blue to colorless plaques on X-gal plates (Maniatis, supra, page 24) in the presence of isopropyl thiogalactoside (IPTG, Sigma Chemical Co.) to be about 90%.

Immunological Screening of the cDNA Library

The λgt11 merozoite cDNA expression library was plated on Y1090 cells at a density of about 10,000 plaques per 150 mm plate. Six such plates were incubated for 3.5 hours at 42° C., overlayered with nitrocellulose filters previously soaked in 10 mM IPTG to induce the expression of the beta-galactosidase fusion protein, and incubated for an additional 4–5 hours to overnight at 37° C. The filters were removed from the plates and subjected to several batchwise washes with TBS (20 mM Tris HCl, pH 8.0, 0.15 M NaCl). Nonspecific protein binding sites were blocked by incubation in 20% fetal calf serum (FCS) in TBS for one hour at room temperature.

The filters were then incubated for one hour with rabbit anti-merozoite serum which had been preadsorbed with the Y1090 cells, at 1:100 dilution in TBS containing 20% calf serum. Nonspecific antibodies were removed in successive washes with TBS, one of which contained 0.1% NP-40. The filters were incubated with goat anti-rabbit peroxidase conjugate (BioRad, Richmond, Calif.) at 1:1000 dilution in TBS plus calf serum for one hour at room temperature. The color reaction was developed with 4-chloro-1-naphthol (BioRad) following the manufacturer's instructions.

Serum from immune chicks was also used for the screening. This serum was preadsorbed with Y1090 cells and used at the same dilution as the rabbit serum. Rabbit anti-chicken antibody was used as the secondary antibody, and goat anti-rabbit horseradish peroxidase conjugate was used as the detecting antibody. Single plaques were isolated in a secondary screen using the same reagents.

One clone, designated lambda 5-7, produced a protein that was strongly reactive with antibodies from the rabbit serum, A second isolate, I-5 was identified by screening with immune chick serum, and proved to contain a cDNA insert of the same size as the 5-7 clone. The DNA sequence analysis indicated that these phage clones encoded the same merozoite antigen.

Expression of the Lambda 5-7 cDNA in E. coli

A 1.2 kb insert from lambda 5-7 was isolated by EcoRI digestion and agarose gel electrophoresis [Maniatis et al., supra, pp. 157–170]. The EcoRI ends were repaired with Klenow polymerase in the presence of dATP and dTTP, and BamHI linkers (GGGATCCC) were ligated to both ends. The modified fragment was inserted into each of the three expression vectors pDS56/RBSII, pDS56/RBSII,-1 and pDS56/RBSII,-2 at the BamHI site. These three vectors are described below. Plasmids containing the inserts in both possible orientations were transformed as described by Mandel et al. [J. Mol. Biol. 53:159 (1970)] into *E. coli* strain M15 carrying the compatible plasmid pDMI.1. The *E. coli* strain M15 harboring plasmids pDS56/RBSII and pDMI.1 is described in European Patent Application, Publication No. 316 695.

Plasmid Construction

Generally, plasmids pDS56/RBSII, -1 and -2 contain the regulatable promoter/operator element N25OPSN25OP29 and the ribosomal binding sites RBSII, RBSII(-1) and RBSII(-2), respectively. These ribosomal binding sites were derived from the ribosomal binding site of the promoter $P_{G25}$ of the *E. coli* phage T5 [European Patent Application, Publication No. 207 459] and were obtained via DNA synthesis.

Due to the high efficiency of expression, the above-mentioned plasmids can be maintained in *E. coli* cells only if the promoter/operator element is repressed by the binding of a lac repressor to the operator. The lac repressor is coded in the lacI gene. N25OPSN25OP29 can be repressed efficiently only when a sufficient number of repressor molecules is present in the cells. Therefore, the $lacI^q$ allele, which contains a promoter mutant responsible for an increased expression of the repressor gene, was used. This $lacI^q$ allele is present on the plasmid pDMI.1, as described below.

The pDMI.1 plasmid carries, in addition to the lac I gene, the neomycin phosphotransferase gene, which confers kanamycin resistance to the bacteria and which is used as the selection marker. pDMI.1 is compatible with the pDS56/RBSII, -1 and -2 plasmids. *E. coli* cells which are transformed with expression vectors PDS56/RBSII, -1 and -2 must contain pDMI.1 to guarantee that the expression vector is held stable in the cells. Induction of this system is achieved by adding IPTG to the medium.

Plasmid pDS56/RBSII

Figure 4:
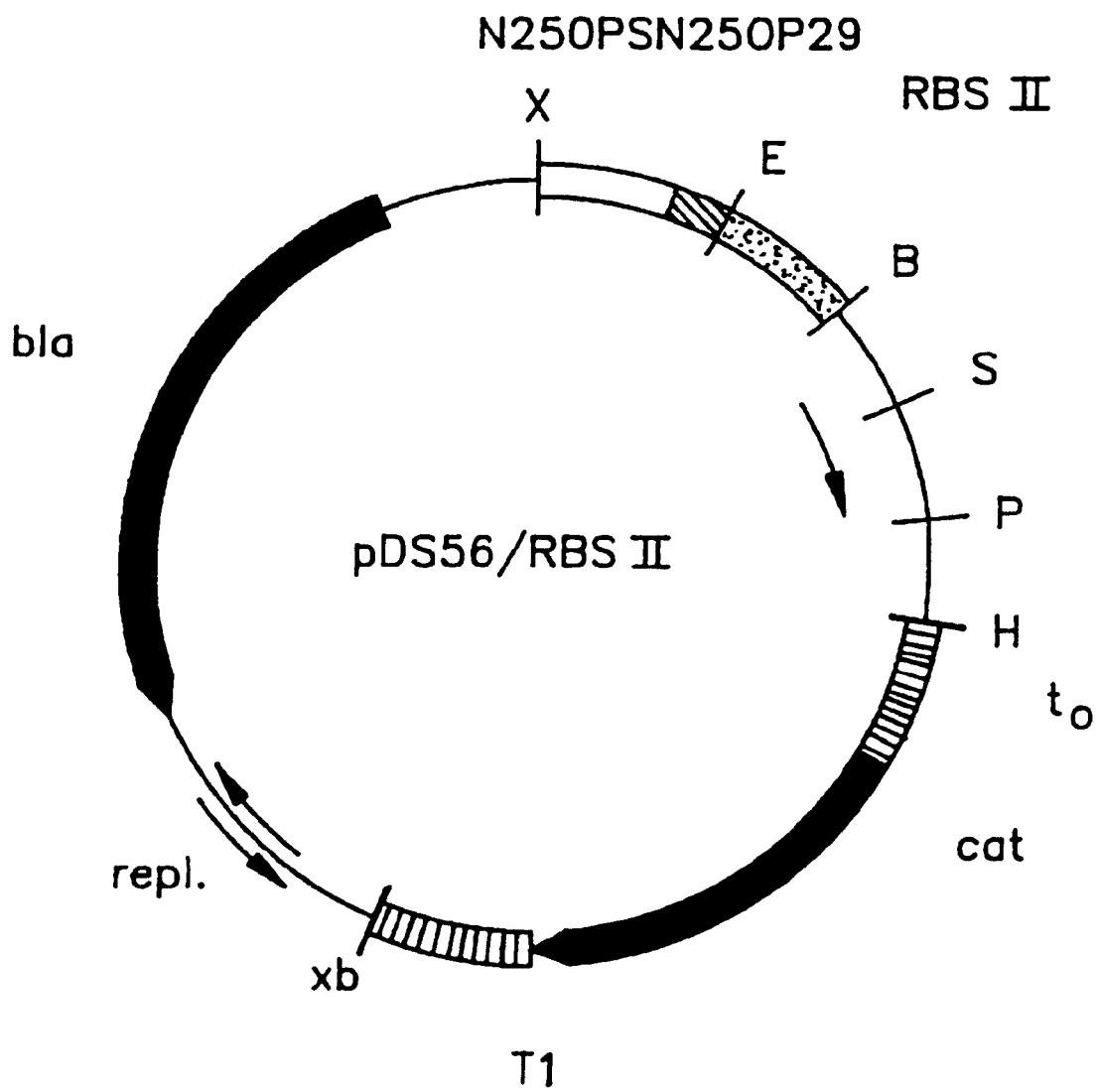

The part of pDS56/RBSII which lies between the restriction cleavage sites for XbaI and XhoI and which contains the replication region and the gene for beta-lactamase (which confers ampicillin resistance to the cells) (FIGS. 4 and 5) was derived originally from the plasmid pBR322 [Bolivar et al., Gene 2: 95–113 (1977); Sutcliffe, Cold Spring Harbor Symp. Quant. Biol. 43: 77–90 (1979)]. However, the gene for beta-lactamase is modified by elimination of the cleavage sites for the restriction enzymes HincII and PstI. These alterations in the DNA sequence have no effect on the amino acid sequence of the beta-lactamase. The remaining part of the plasmid carries the regulatable promoter/operator element N25OPSOP29 followed, by the ribosomal binding site RBSII, which is part of an EcoRI/BamHI fragment, cleavage sites for the restriction enzymes SalI, PstI and HindIII, the terminator to of *E. coli* phage lambda [Schwarz et al., Nature 272: 410–414 (1978)], the promoter-free gene of chloramphenicol acetyltransferase [Marcoli et al., FEBS Letters, 110: 11–14 (1980)] and the terminator T1 of the *E. coli* rrnB operon [Brosius et al., J. Mol. Biol. 148: 107–127 (1981)].

Plasmid pDS56/RBSII(-1)

Plasmid pDS56/RBSII(-1) (FIGS. 6 and 7) is similar to plasmid pDS56/RBSII but contains the ribosomal binding site RBSII(-1).

Plasmid pDS56/RBSII(-2)

Figure 8:
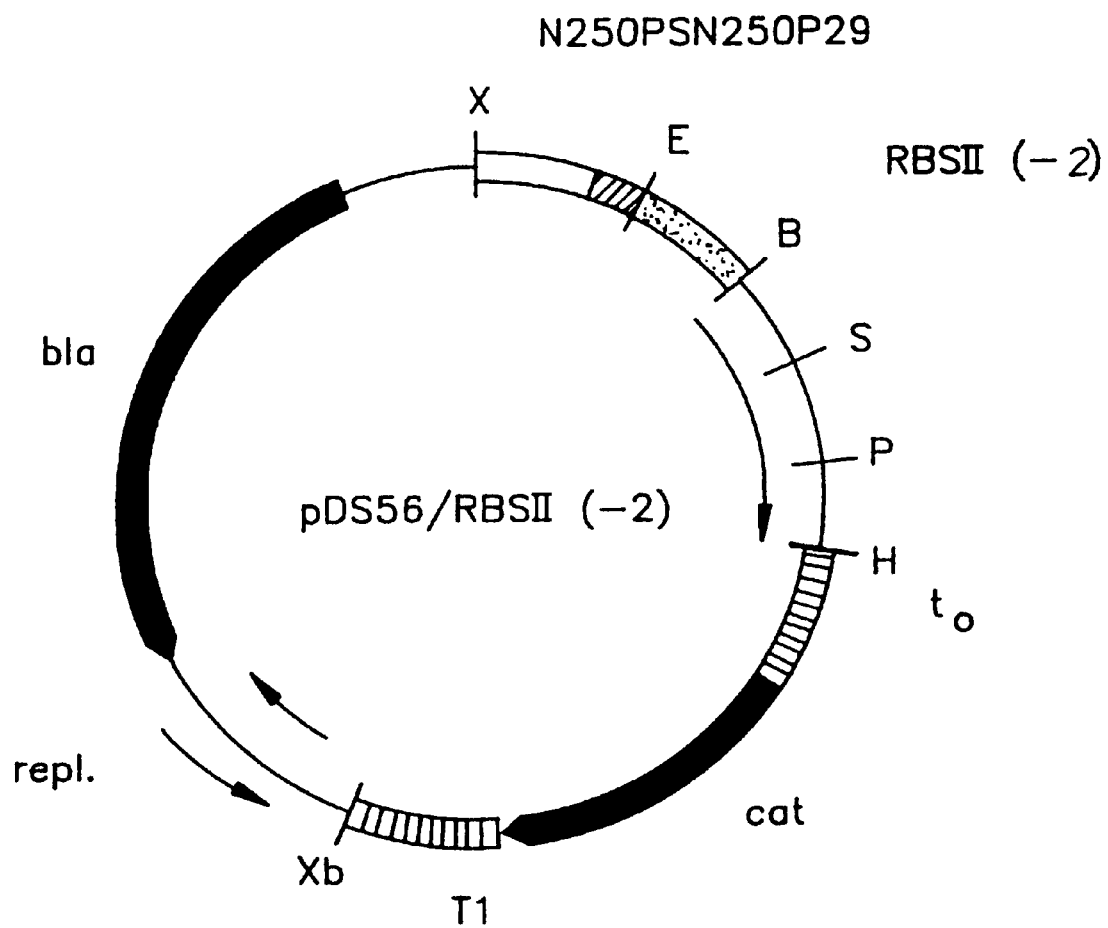

Plasmid pDS56/RBSII(-2) (FIGS. 8 and 9) is similar to plasmid pDS56/RBSII but contains the ribosomal binding site RBSII(-2).

The difference in these three plasmids is that they differ by one nucleotide following the ATG start codon resulting in protein expression from all three potential reading frames.

Plasmid pDMI.1

Figure 10:
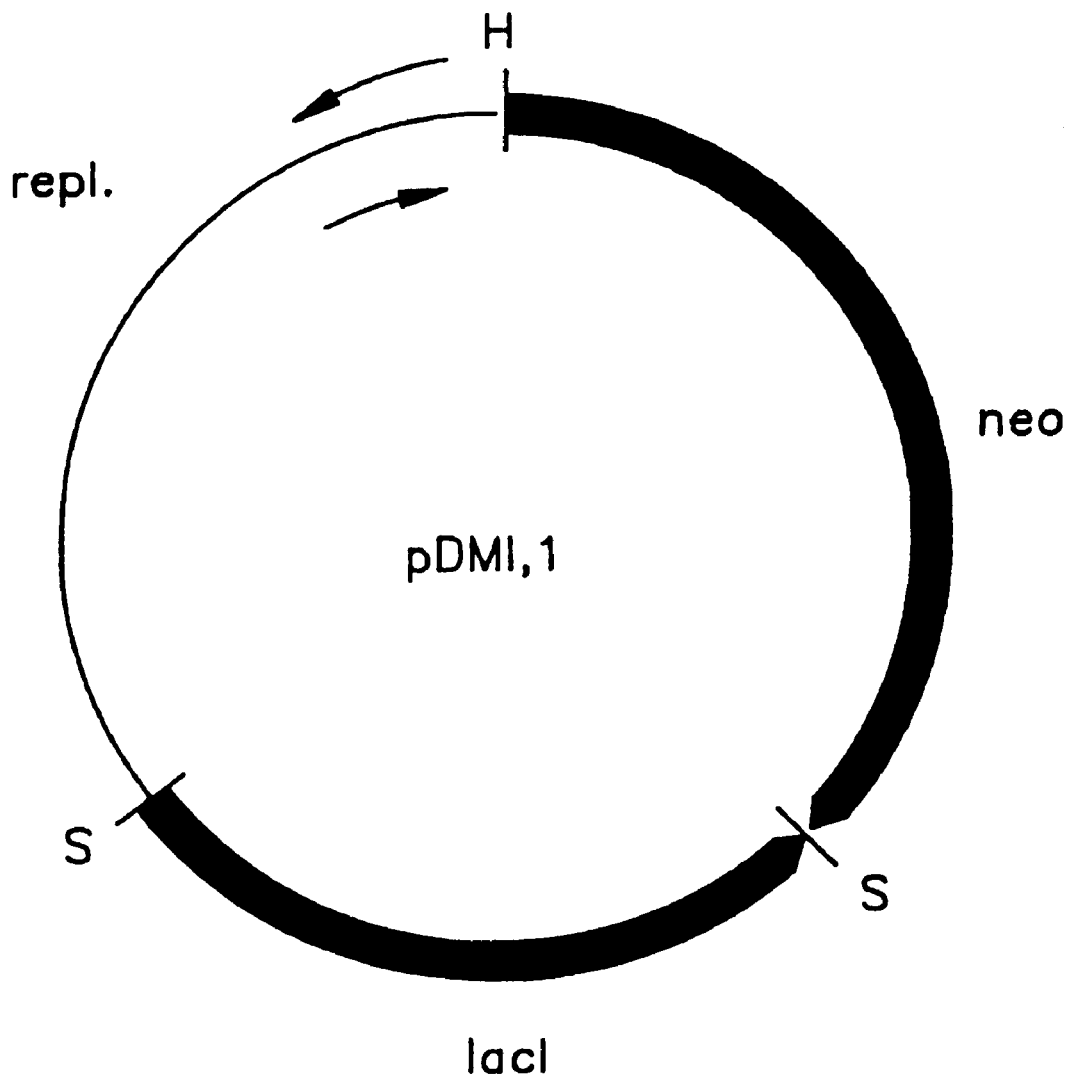

Plasmid pDMI.1 (FIGS. 10 and 11) carries the gene for neomycin phosphotransferase from the transposon Tn5 [Beck et al., Gene 19: 327–336 (1982)], which confers kanamycin resistance to E. coli cells, and the lacI gene [Farabough, Nature 27: 765–769 (1978)] with the promoter mutation I$^q$ [Calos, Nature 274: 762–765 (1978)], which codes for the lac repressor. Moreover, plasmid pDMI.1 contains a region of the plasmid pACYC184 [Chang and Cohen, J. Bacteriol. 134: 1141–1156 (1978)], which contains all information required for the replication and stable transmission to the daughter cells.

It should be understood that in addition to the above-described plasmid, any E. coli expression system is contemplated to be useful in this experiment.

The bacterial transformants were grown at 37° C. in LB medium [Maniatis et al., supra, page 68] and expression of protein induced by addition of 1 mM IPTG to the medium. After incubating for 1 hour, 1-ml samples were taken, and the cells in the samples were collected by centrifugation. The cell pellets were treated as described by Crowl et al., supra, and the lysates were subjected to SDS PAGE. Following electrophoresis, the proteins in the gels were either stained with Coomassie brilliant blue or transferred to nitrocellulose membranes for Western blot analysis [Towbin et al., Proc. Natl. Acad. Sci. USA 76:4350 (1979); Burnetti, Anal. Biochem. 112:195 (1981)], using the rabbit anti-merozoite serum as described above.

The analysis showed that the 1.2 kb cDNA molecule encoded in one orientation in all three reading frames a protein that migrated with an apparent molecular weight of about 33 kilodaltons as measured by SDS-PAGE and reacted with the antibodies from the rabbit anti-merozoite serum.

DNA Sequence Analysis

In general, small scale isolation of plasmid DNA from 1 ml of saturated overnight cultures were carried out using the procedure of Birnboim et al. [Nucleic Acids Research 7: 1513 (1979)]. This procedure allows the isolation of a small quantity of DNA from a bacterial colony for analytical purposes. Larger amounts of plasmid DNA were prepared using 1-liter cultures following a standard protocol with cesium chloride centrifugation [Maniatis et al., supra, page 93].

The DNA sequence of the 1.2 kb EcoRI cDNA insert from lambda 5-7 was determined as follows. The insert was digested with EcoRI, purified by gel electrophoresis, and ligated to the EcoRI digested pEV-vrf plasmid described by Crowl et al. [Gene 38: 31 (1985)]. This plasmid was designated pEV/5-7 and was used to propagate the 1.2 kb cDNA insert for hybridization analysis (as described below) and in preliminary DNA sequence analysis by the method of Zagursky etal. [Gene Anal. Tech. 2: 89 (1983)].

To determine the complete DNA sequence, the 1.2 kb cDNA insert from pEV/5-7 was further subcloned into the M13mp19 single-stranded phage vector using the BIO-RAD™ M13 Cloning Kit and the SEQUENASE™ sequencing Kit. The sequence was determined by the dideoxy chain termination method of Sanger et al. [Proc. Natl. Acad. Sci. USA 74: 5463 (1977)] following the recommended protocols in the SEQUENASE™ Kit (United States Biochemical Corp., Cleveland Ohio, USA).

The complete nucleotide sequence of the 1.2 kb cDNA from pEV/5-7 including 5' and 3' untranslated regions is shown in FIGS. 1a–1e.

The cDNA sequence predicts an open reading frame extending from the ATG at position 68 to the TGA stop codon at position 1013 encoding 315 amino acid residues as shown in FIGS. 1a–1e.

The theoretical size of 33,375 Dalton for this protein correlates with the immunoprecipitated product from the in vitro translation of merozoite mRNA (see FIG. 2, panel C, lane a) using the antigen-select reagent and with the protein expressed from the cDNA in the E. coli expression vectors described above.

Analysis of the deduced amino acid sequence of the protein encoded by the lambda 5-7 cDNA insert (FIGS. 1a–1e) shows that the first twenty amino-terminal amino acid residues have a overall hydrophobic character, suggestive of a possible signal peptide sequence.

For a number of regions of the polypeptide, with the stated amino acid sequence, epitopes can be designated based on a combination of the hydrophilicity criteria according to J. P. Hopp and K. R. Woods [Proc.Natl.Acad.Sci.USA 78: 3824–3828 (1981)] and secondary structure criteria according to P. Y. Chou and G. D. Fasman [Advances in Enzymology 47: 45–148 (1987)].

The following regions contain probable epitopes for antibodies:

$S_{79}$-$V_{86}$ (SEQ ID NO: 3)
$C_{95}$-$K_{123}$ (SEQ ID NO: 4)
$P_{137}$-$V_{139}$ (SEQ ID NO: 5)
$R_{147}$-$F_{152}$ (SEQ ID NO: 6)
$N_{155}$-$E_{162}$ (SEQ ID NO: 7)
$R_{169}$-$E_{173}$ (SEQ ID NO: 8)
$T_{181}$-$E_{186}$ (SEQ ID NO: 9)
$Q_{196}$-$G_{225}$ (SEQ ID NO: 10)
$T_{239}$-$G_{243}$ (SEQ ID NO: 11)
$T_{252}$-$G_{256}$ (SEQ ID NO: 12)
$A_{265}$-$K_{269}$ (SEQ ID NO: 13)
$D_{276}$-$K_{289}$ (SEQ ID NO: 14)
$T_{298}$-$E_{315}$ (SEQ ID NO: 15)

In addition, T-cell epitopes may be derived on theoretical grounds according to Berzofsky's amphiphilicity criterion [Good et al. Science 235,1059–1062 (1987)]. T-cell epitopes are processed from antigens [H. M. Grey and R. Chestnut, Immunol. Today 6:101–106 (1985), transported intracellularly [Schwartz A. L., Ann.Rev.Immun. 8: 195–229 (1990)], and recognized by the T-cell receptor complex. Although some of the algorithms were designed primarily to identify Class II antigenic sites, because of the similarities with Class I peptide interactions, they also appear to be useful for the identification of peptide targets for cytotoxic T lymphocytes [Feller and de la Cruz, Nature 349: 720–721 (1991)]

In addition a potential glycosylation site is located at the amino acid asparagine at position 20 ($D_{20}$). The carbohydrate groups are known to confer important physical properties such as conformational stability, resistance to proteases, charge and waterbinding capacity. The importance of carbohydrate groups in biological recognition where sequence diversity provides signals for protein targeting, cell-cell interactions and more important host-pathogen interactions are well described in the literature [for review see J. C. Paulson, TIBS 14: 272–276 (1989)].

Hybridization Analysis

DNA was isolated from excysted, sporulated oocysts following treating with trypsin and bile and washing with PBS as follows:

The parasite material (approximately 1×10$^9$ oocysts) was suspended in 20 ml of 0.5 M EDTA, pH 8.0, 0.5% sarcosyl (Sigma, St. Louis, Mo., USA) and digested with proteinase K (Boehringer-Mannheim, BRD) at 0.1 mg/ml for 2 hours at 50° C., with RNase (10 mg/ml) for 1 hour at 37° C., and again with proteinase K for 1 hour at 50° C. The protein was removed with 2 extractions with phenol saturated with 20 mM Tris HCl, pH 7.5, 1 mM EDTA (TE), and one extraction with phenol/chloroform (1:1). The aqueous phase was dialysed extensively against TE and concentrated by ethanol precipitation. A typical yield of 0.4 mg DNA per $1 \times 10^6$ oocysts was obtained.

The parasite DNA was digested with various restriction endonucleases following the manufacturers' protocols and the resulting DNA fragments were resolved by electrophoresis at 40 V for 2.5 hours in 0.8% agarose in Loening Buffer (4.7 g $NaH_2PO_4$, 4.36 g Tris base, 0.372 g $Na_2EDTA$ per liter, pH 7.6). The gel was treated with 0.25 M HCl for 30 minutes, and transferred to a Zeta-Probe membrane (BIO-RAD™) in 0.4 M NaOH overnight. The filter was neutralized in 2× SSC (pH 6.8) and baked for one hour at 80° C. under vacuum.

The filter was prehybridized for 3 hours at 65° C. in 7% SDS, 1% BSA (Boehringer, fraction V), 0.5 M $NaHPO_4$ buffer, pH 7.2. The 5-7 gene EcoRI insert was gel isolated following digestion of the pEV/5-7 plasmid, as described above, with EcoRI, and labeled by random-priming with Klenow fragment in the presence of $^{32}P$-labeled deoxynucleotides. The labelled insert was separated from unincorporated nucleotides in Spin-Columns (BIO-RAD™), denatured and added to the hybridization solution. Following incubation for 12 hours at 65° C., the filters were washed 3 times with 2× SSC/0.1% SDS, and twice with 0.1× SSC/ 0.1% SDS at 65° C. The genomic DNA fragments hybridizing to the probe were detected by autoradiography. Although the pEV/5-7 plasmid was used here, it is understood that any equivalent vector containing the 1.2 kb cDNA insert of the merozoite 5-7 gene would also perform in an acceptable manner.

Figure 3:
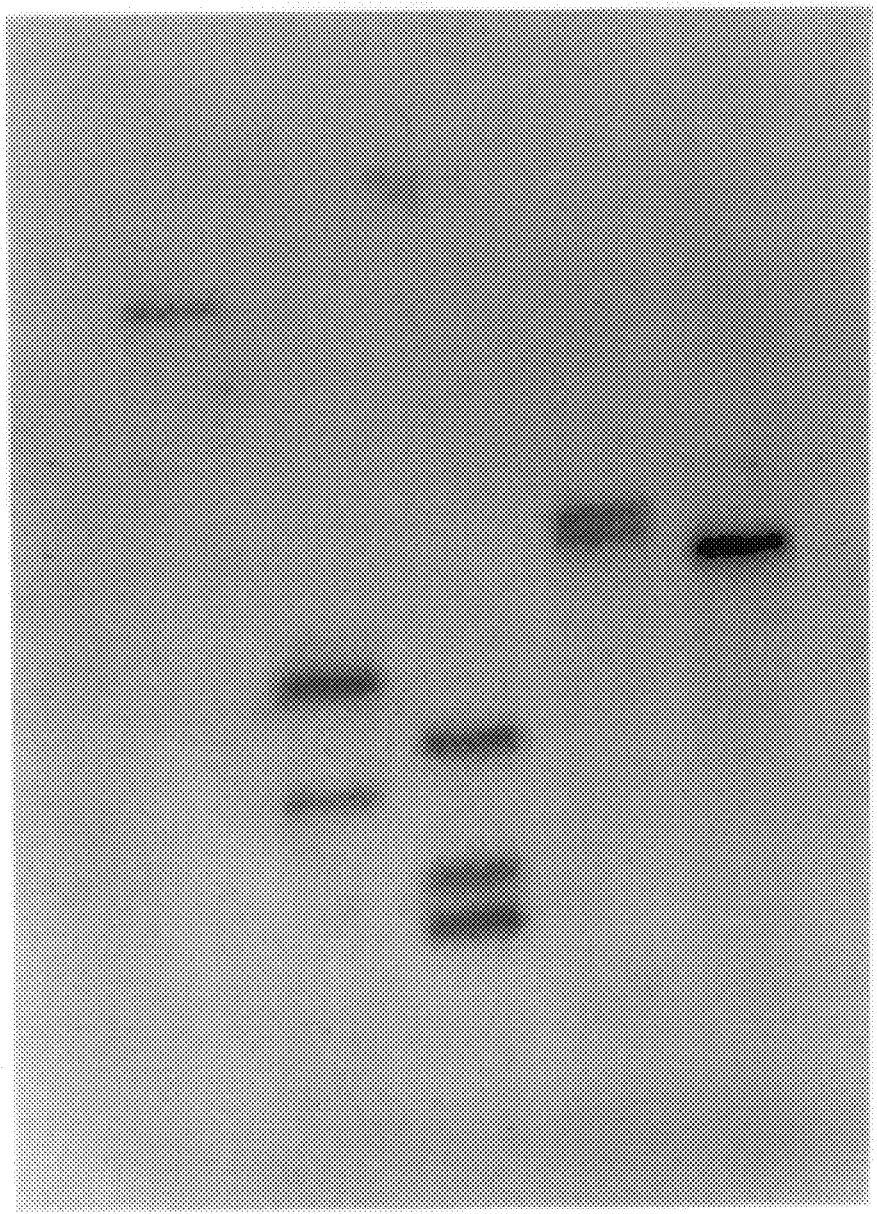

The results of this analysis are shown in FIG. 3, where the results of digestion by PvuII (1), HincII (2), PstI (3), SphI (4) or SacI (5) can be seen.

Genomic DNA fragments of 6.5 and 3.6 kb were detected following digestion with PvuII and SacI, in lanes 1 and 5, respectively. Since there are no sites for these enzymes in the cDNA clone, the maximum size of the Eimeria gene can be estimated to be 3.6 kb. Digestion of genomic DNA with EcoRI produced a 1.2 kb genomic fragment corresponding in size to the cDNA fragment. Double digestion with HincII and EcoRI produced a 0.9 kb fragment predicted from the cDNA sequence flanked closely by EcoRI sites.

Three fragments were detected following digestion with PstI (lane 3). Two PstI sites are predicted from the cDNA sequence, which would produce an internal fragment of 305 bp and two joint fragments. The appearance of a third large PstI fragment is probably the result of incomplete digestion at the internal PstI sites.

The pattern of fragments produced by SphI (lane 4), which also cuts twice in the cDNA, provides no definitive information. The small internal SphI fragment predicted from the cDNA sequence could not have been detected in this gel.

In a Northern blot analysis [Alwine et al., Proc. Natl. Acad. Sci. USA 74: 5350 (1977)] of poly(A)-containing mRNA isolated from merozoites, the 1.2 kb cDNA fragment of the lambda 5-7 gene hybridized to a single mRNA species of approximately 1.3 kb in length. From the size correlation, it is apparent that the 5-7 clone, together with the 5' extension determined from the I-5 isolate mentioned above, represents the full-length sequence of the cDNA, with the possible exception of the extreme 5' nucleotides.

Taken together, the foregoing observations are consistent with co-linearity of the cDNA and genomic sequences.

EXAMPLE 2

In order to produce a more effective way of immunizing chicks with the E. tenella merozoite antigen 5-7, the 1.2 kb cDNA described above was cloned into vaccinia virus. The recombinant vaccinia virus obtained in this way was used as a subunit coccidiosis vaccine to vaccinate chicks.

Construction of the Vector

All forms of recombinant vaccinia virus (rVV) made were based on homologous recombination into the viral thymidine kinase (TK) locus as described by Macket et. al. [Proc.Natl.Acad.Sci.USA 79: 7415 (1982)]. The TK locus has been mapped to the vaccinia virus (VV) HindIII J fragment [Hruby et al., J. Virol. 43: 403 (1982)], and part of this fragment has been sequenced [Weir et al., J. Virol. 46: 530 (1983)].

Figure 12:
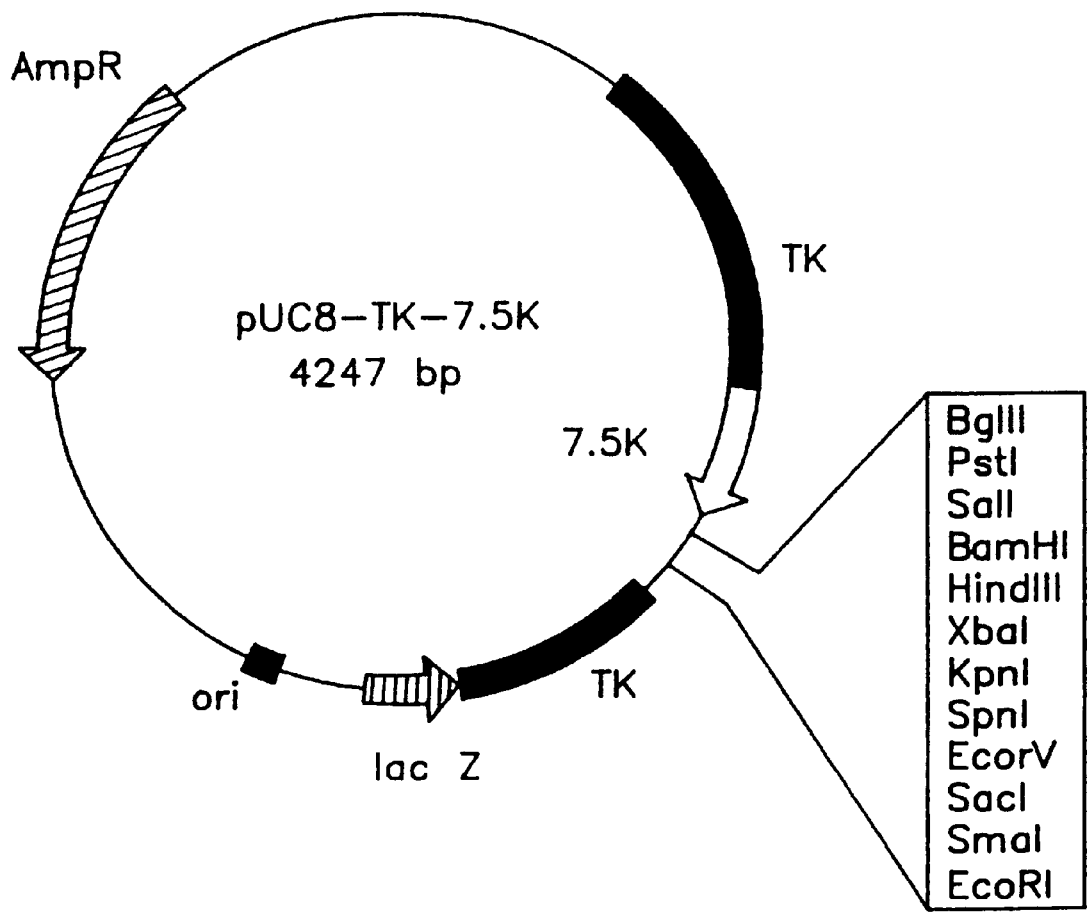

The construction of the vector for recombination pUC8-TK-7.5K is basically described in European Patent Application, Publication No. 344 808. Briefly, the vector consists of a pUC8 plasmid backbone carrying the vaccinia virus TK gene disrupted by the VV 7.5K promoter [Venkatesan et al., Cell 25: 805 (1981)]. Downstream of the promoter in the direction of the transcription, a multiple cloning site has been constructed to allow the introduction of the gene to be expressed. FIG. 12 shows the schematic drawing of the pUC8-TK-7.5K plasmid.

Figure 13:
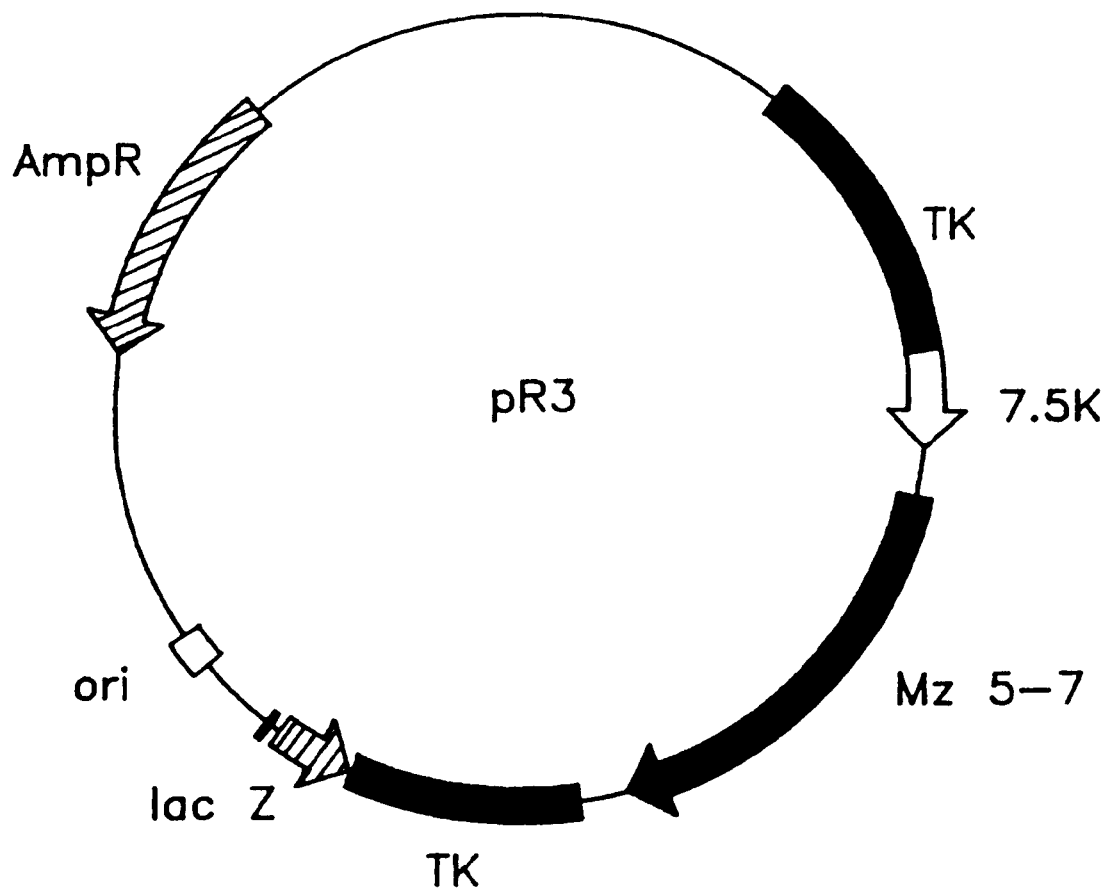
FIG. 13 is a schematic drawing of the recombinant plasmid pR3.

To generate our construct the EcoRI fragment encoding the merozoite 5-7 gene was cloned into the EcoRI site of the polylinker contained in the basic vector shown in FIG. 12. Constructs containing the fragment in the correct orientation were propagated and modified as described below to delete an in-frame start codon situated 97 nucleotides upstream of the natural start codon of the merozoite 5-7 gene. For this purpose the plasmid was digested with the restriction enzymes SmaI and BglII. After rendering the BglII site blunt with Klenow enzyme in the presence of the four deoxyribonucleotides, the plasmid was religated and the construct pR3 (FIG. 13), carrying the expected deletion, was propagated and used for recombination into the vaccinia virus. FIGS. 14a–q show the complete sequence of this recombination plasmid.

Figure 15:
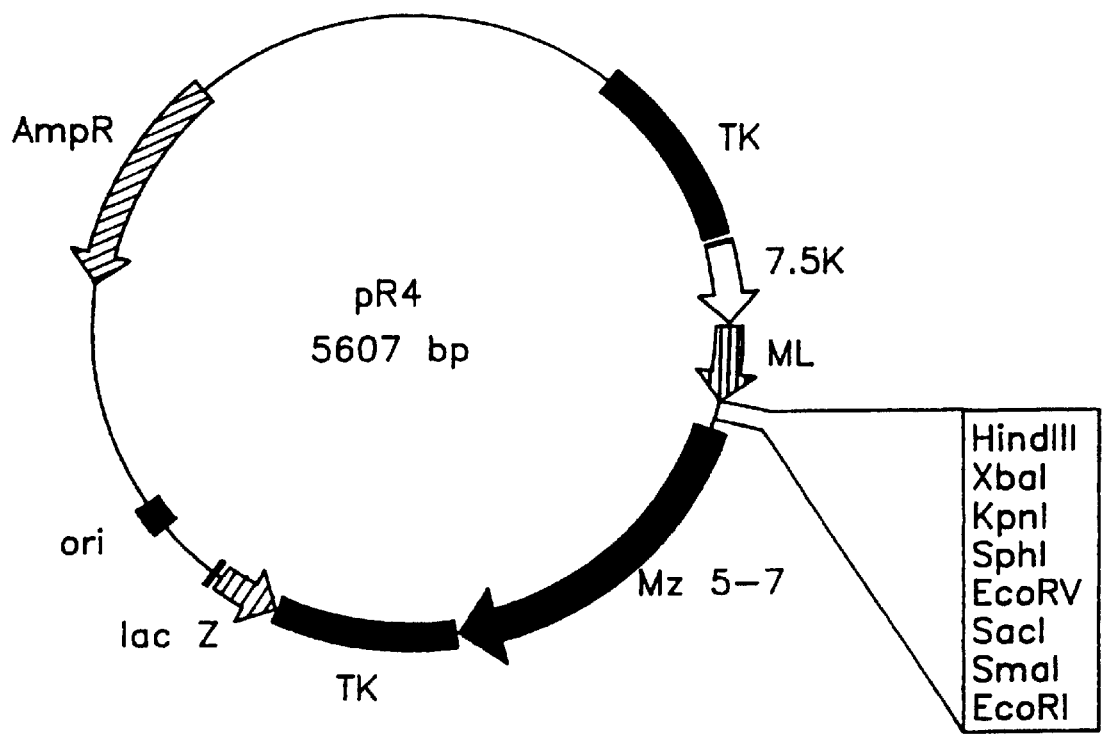
FIG. 15 is a schematic drawing of the plasmid pR4. ML stands for the malaria leader sequence.

In addition the merozoite 5-7 gene was also introduced into the vector for recombination containing the DraI-HindIII malarial antigen leader. This vector, which is described in European Patent Application, Publication No. 344 808, is based on vector pUC8-TK-7.5K but has in addition, downstream of the 7.5K promoter, the sequence of the 190 kDa malaria antigen leader. Adjacent to this leader sequence a multiple cloning site has been constructed to allow the introduction of the gene to be expressed. The resulting transcript driven by the VV 7.5K promoter will be translated into a protein, carrying at the N-terminus the 190 kDa malaria antigen leader. In vivo processing at the potential cleavage site of the leader sequence leads to the maturated protein. FIG. 15 shows the schematic drawing of this construct pR4 carrying the merozoite 5-7 gene.

Construction of Recombinant Vaccinia Virus

CV1 cells plated on a 8 $cm^2$ culture plate were adapted to 33° C. and grown to 80–90% confluency were infected with 0.1 plaque forming units (pfu) per cell of the vaccinia virus temperature sensitive mutant ts N7 [Drillien, R. and Spehner, D. Virology 131: 385–393 (1983)]. After 2 hours at the permissive temperature of 33° C. in a $CO_2$ incubator [Kieny et al., Nature 312: 163 (1984)] the cells were transfected with 0.25 ml of a calcium phosphate DNA precipitate as described in Weir et al., [Proc.Natl.Acad.Sci.USA 79: 1210–1214 (1982)]. The calcium-phosphate-DNA precipitate mixture consisted of: (0.8% NaCl, 0.038% KCl, 0.0134 M $Na_2HPO_4.2H_2O$, 0.1% Glucose; pH 7.0 and 125 mM $CaCl_2$, 200 ng of the vaccinia wild type DNA (WR strain) and 100 ng of the appropriate recombinant plasmid pR3 or pR4. After one hour at room temperature additional medium was added to the plate followed by an incubation for 2 hours at 39.5° C. in a 5% $CO_2$ incubator. At this temperature, the ts N7 virus cannot replicate, resulting in a selection for viruses which have recombined at least in the ts 7 locus.

After two days of incubation at 39.5° C. the cells were harvested by scraping and the suspension was further disrupted by sonication. This homogenate was then used to obtain TK negative (TK⁻) virus by titration on human TK⁻ 143 cells in the presence of 30 μg/ml of bromodeoxyuridine (BUdR). Plaques were picked and the virus was further plaque-purified two more times in human TK⁻ 143 cells in the presence of 30 μg/ml of BUdR. Virus stocks were then made in CV1 cells in the absence of BUdR. The recombinant vaccinia virus R3.2 and R4.1 respectively were checked for the presence of the 1.2 kb cDNA merozoite gene inserted into the TK gene, by digesting the viral DNA with HindIII and comparing the rVV DNA pattern to a pattern of wild type (WR) vaccinia DNA digested with the same restriction enzyme. If recombination had occurred a shift in the HindIII J DNA fragment should be seen after electrophoresis in a 1% agarose gel. This was indeed observed. The shift correlated with the calculated values deducted from the insert size.

Test for Expression

To test for the expression of the merozoite 5-7 antigen by the recombinant virus, CV1 cells were infected with either rVV R3.2 or rVV R4.1 and harvested 48 hours later. After centrifugation of the cells, the pellets were solubilized in Laemmli sample buffer [Nature 277: 680 (1970)] in the presence of beta-mercaptoethanol as a reducing agent. After boiling for 5 minutes, the samples were loaded on a 12.5% SDS-PAGE slab gel. After electrophoretic separation the proteins were blotted onto nitrocellulose membranes (Trans-Blot, BIO RAD) in Blot-buffer: 25 mM Tris-HCl, 0.19 M glycine; pH 8.3 and 20% (v/v) methanol at 80 V constant voltage in a Transblot transfer cell (BIO RAD Laboratories) for 2 hours at 4° C. [Towbin et al., Proc. Natl. Acad. Sci.USA 76: 4350–4354 (1979)].

For immuno-detection the nitrocellulose was pretreated with 5% non-fat milk powder in TBS (20 mM Tris-HCl, 150 mM NaCl, adjusted to pH 8) for 45 minutes and incubated for 2 hours or overnight at room temperature with a 1:50 dilution of the rabbit anti-E. tenella merozoite serum in TBS buffer containing 20% (v/v) fetal calf serum. The nitrocellulose was then washed three times for 10 minutes in TBS containing 0.1% NP40 before incubation for 2 hours at room temperature with an affinity-purified goat-anti-mouse IgG (H+L) peroxidase conjugate (BIO-RAD) at a 1:1000 dilution in TBS and 5% non-fat milk powder (H+L stands for heavy and light chaines of IgG). The blots were then washed three times as described above. Binding of the peroxidase conjugate was detected by reacting the nitrocellulose in 0.018% 4-chloro-1-naphthol in $H_2O$ and 0.02% (v/v) $H_2O_2$. The reaction was stopped by washing the blot extensively in H20.

It was found that the rabbit anti E. tenella merozoite serum reacted in Western blots (Towbin et al; supra) with CV1 cells, infected with the rVV R3.2, with two distinct protein bands of 33 kDa and 23 kDa respectively. BIO-RAD prestained SDS-PAGE molecular weight standards (low range) were used as a reference. CV1 cells infected with wild type WR vaccinia virus did not react with the rabbit anti E. tenella merozoite serum. The size of the 33 kDa protein correlates with theoretically expected value of the precursor protein as shown in FIG. 2, panel C, lane a). The smaller 23 kDa protein could be the processed version of the precursor protein mentioned above, which was also seen on the surface of the merozoite (see FIG. 2, panel A and B, lane b). The same results were observed with CV1 cells infected with the rVV R4.1.

In addition it could further be shown by Western blot analysis that immune serum from chickens infected with sporulated E. tenella oocysts recognized the merozoite 5-7 proteins (33 kDa and 23 kDa) expressed in CV1 cells infected with the vaccinia virus recombinants R3.2 and R4.1 respectively.

Production of Virus

The WR strain virus can multiply in almost all cell types [Drillien et al., J. Virology 48: 843 (1978)], and its multiplication can be observed directly through formation of plaques. In most cases we used CV1 cells to prepare large stocks of the virus.

For infection, the medium was removed from 80–90% confluent CV1 cells growing in 175 $cm^2$ culture flasks (e.g. Falcon 3028), and the cells were incubated in a PBS solution containing virus (0.1 pfu/ml, 0.01 ml/$cm^2$) for one hour at room temperature (20° C.). Medium I was then added (0.2 ml/$cm^2$), and the flasks were incubated at 37° C. for 2–3 days until about 80% of the cells had lysed. The resulting stock solution was stored directly with cells and medium in the original culture flasks at −30° C. before virus purification.

The following purification steps were used to obtain a virus preparation free of host cell specific components. Infected cell cultures which had been stored at −30° C. were thawed and the remaining cells were freed from the surface of the flasks by shaking or scraping. The cells and viruses were centrifuged out of the medium (Sorvall centrifuge GSA rotor, one hour at 5000 rpm, 10° C.). The pellet of cells with the virus particles was resuspended in PBS (10–20× the volume of the pellet) and centrifuged as above. This pellet was then resuspended in a 10-fold volume of RSB Buffer (10 mM Tris-HCl adjusted to pH 8.0, 10 mM KCl, 1 mM $MgCl_2$).

To lyse the remaining intact cells and free the virus from the cell membranes, the above suspension was subjected to sonication (twice, 10 seconds at 60 watts at room temperature in a sonifier, e.g. Labsonic 1510 with a 4 mm probe). The mixture was centrifuged in a Sorval GSA rotor for 3 minutes at 3000 rpm, 10° C. A virus suspension, free from cell nuclei and large cell debris, was thus produced. The supernatant was carefully removed, and the pellet was resuspended in RSB buffer, sonicated and centrifuged as above.

The second supernatant was combined with the first, layered onto a 10 ml 35% sucrose cushion (in 10 mM Tris-HCl pH 8.0) and centrifuged for 90 minutes at 14000 rpm in a Beckman SW 27 rotor at 10° C. The supernatant was decanted and the pellet of virus particles was resuspended in 10 ml of 10 mM Tris-HCl, pH 8.0, sonicated to homogenize the mixture (2 times for 10 seconds at room temperature as described above) and loaded onto a step gradient for further purification.

The step gradient consisted of 5 ml aliquots of sucrose in 10 mM Tris-HCl pH 8.0, of the following concentrations:

20%, 25%, 30%, 35% and 40%. This gradient was centrifuged in a Beckman SW27 rotor for 35 minutes at 14000 rpm, 10° C. Several bands containing virus particles were visible in the 30%–40% sucrose region. This region of the gradient was removed and diluted with PBS and the virus particles were sedimented (Beckmann SW27 rotor for 90 minutes at 14000 rpm at 10° C.). The pellet containing almost exclusively virus particles was resuspended in PBS so that the virus concentration was on the average 0.5–1× $10^{10}$ pfu/ml. This virus stock was used either directly or diluted with PBS.

To determine the virus concentration and the purity of the virus stock, two methods were used. The absolute concentration of virus particles was conveniently obtained by measuring the optical density (OD) of the stock solution in a spectrophotometer at the wavelength 260 nm (OD/260 nm), where 1 OD/260 equals about $1.2 \times 10^{10}$ particles per ml [Joklik, Virology 18: 9 (1962)]. Virus concentration was also obtained by titrating the virus on cells (plaque assay), assuming that only one out of 60 virus particles can infect a cell.

To titer the virus concentration on cultured cells, chick embryo fibroblasts (CEF) cells were grown in Medium I on 8 $cm^2$ culture plates (Falcon 3001). After the cells reached 80%–90% confluency, the medium was removed, replaced with 0.2 ml of a diluted virus solution in PBS, and left at room temperature for one hour. The virus stock solution was diluted in 10-fold steps. Two ml of semi-solid Medium I (Medium I+1% agarose) were added to each plate and the plates were then placed for 16–24 hours in a $CO_2$ incubator at 37° C. Subsequently, 2 ml of semi-solid Medium I containing 0.2% neutral red was layered on to stain the living cells, and the plates were incubated for an additional 16–24 hours. The colorless plaques were then counted under a microscope.

EXAMPLE 3

Chick Immunization

To determine whether the vaccinia viral vector rVV-R3.2, harboring the gene merozoite 5-7 could protect chicks against challenge by sporulated oocysts of a pathogenic strain of E. tenella, the following vaccinations were carried out.

repeated twice, but for one treatment group the last virus injection was replaced by an inoculation with 5000 sporulated oocysts of a virulent strain of E. tenella (e.g. strain T7-776/21), in order to simulate the natural exposure of chicks to infectious coccidia under field conditions. One week after the last immunization all chicks were bled for analytical purposes and another week later (day 45) the birds were challenged with 50000 sporulated oocysts of E. tenella (e.g. strain T7-776/21). The parasites were allowed to conclude their developmental cycle of 7 days and on day 52 the chicks were bled, sacrificed and necropsied. The infected ceca were removed, the lesions due to the parasitic development were scored and the whole tissue was homogenized to determine its oocyst content. Moreover, the performance of the chicks (daily weight gain and feed conversion) was recorded.

Protection Experiment

The data in Table 1 shows clearly that the vaccination with the recombinant vaccinia virus R3.2 had a considerable protective effect against the severe coccidial challenge. The lesion scores were reduced by 18% and the oocyst content in the ceca by 35% in comparison to the infected control. Performance, which is economically the most important parameter, was improved by 62% for the daily weight gain and by 56% for the feed conversion. However, when the last virus injection was replaced by a mild coccidiosis infection, the protection of chicks against coccidiosis was nearly complete. Performance of these chicks was equivalent to the non-infected controls and lesion scores as well as oocyst content of the ceca was low. Since a single inoculation with E. tenella has never been demonstrated to confer such a high degree of protection, it was concluded that the virus based vaccination had strongly primed the immune system of the chicks so that the subsequent mild coccidial infection could exhibit a booster effect, resulting in such an effective immune protection against coccidiosis.

Humoral status of the chickens

The humoral status of the chickens was analyzed by indirect ELISA and Western blot using the following method.

TABLE 1

Performance and parasitological parameters of chicks, vaccinated with recombinant vaccinia virus rVV-R3.2 after challenge with 50'000 oocysts of E. tenella

| Treatment | | | | Number of | Mean Body Weight | | Daily Weight | Mean Feed | Cecal | Oocyst Content |
|---|---|---|---|---|---|---|---|---|---|---|
| Immunization | | | Chal- | Groups/ | (g) on | | Gain (g) | Conversion | Lesion | of the Ceca |
| 1. | 2. | 3. | lenge | Chicks | Day 45 | Day 52 | Day 45–52 | Day 45–52 | Score | (Mio/g of Ceca) |
| *) | *) | *) | − | 3/12 | 788.2 | 985.8 | 28.2 | 2.66 | 0 | 0 |
| V | V | V | + | 3/12 | 778.1 | 860.4 | 11.8 | 5.19 | 1.58 | 1.73 |
| V | V | C | + | 3/12 | 779.3 | 960.6 | 25.9 | 2.98 | 0.75 | 0.18 |
| — | — | — | + | 3/12 | 783.0 | 834.3 | 7.3 | 11.88 | 1.92 | 2.67 |

*) V = Injection with $3 \times 10^8$ PFU of recombinant virus in 100 μl per chick,
C = Inoculation with 5000 E. tenella oocysts per chick Cockerels of the layer breed WARREN, supplied by the hatchery E. Wuethrich in Belp (Switzerland), were kept in wire-floored cages on a commercial broiler type grower diet, consisting predominantly of maize, wheat and soya-bean. On day 17, the chicks were inoculated with $3 \times 10^8$ pfu of the recombinant vaccinia virus R3.2 in 100 ml of PBS, whereas 50 ml were injected subcutaneously into the wing web, another 50 ml were given intramuscularly into the breast. With intervals of one week each, this procedure was The Western blot analysis was done as described above, except that one additional incubation step before the chicken sera samples was performed. This step consisted in incubation of the blotted nitrocellulose with hyperimmune rabbit anti vaccinia serum (2 hours at room temperature, 1:50 dilution) to cover all vaccinia specific proteins.

For the indirect ELISA, third generation merozoites of E. tenella harvested from in vitro primary chicken kidney cell cultures were used. The microtiter plates were coated with 3000 merozoites per well dissolved in 100 ml of sodium carbonate-bicarbonate buffer (pH 9.6) and incubated overnight at 4° C. The plates were washed three times with deionized water and refilled with 200 ml of blocking buffer (0.1 M $Na_2HPO_4$ adjusted to pH 6.5 with HCl, 1% BSA, 0.5 g/l sodium ethylmercurithiosalicylate). The blocking lasted overnight at 4° C. Two serum samples per animal were tested. One sample was taken one week after the last immunization the second just before challenge of the animals with coccidia. The samples were diluted in two fold steps in PBS containing 3% milk powder starting with a 1 to 50 fold dilution. Incubation was done for 4 hours at 37° C. (100 ml). The plate was washed as described above followed by addition of 100 ml per well of the conjugate goat anti-chicken (H+L) labeled with peroxidase (1:2000 dilution in PBS containing 3% milk powder). Incubation was done at 37° C. for 2 hours. Antibody-antigen complexes were visualized by adding 100 ml of TMB-substrate. The TMB-substrate consisted of one part of TMB (0.24 g tetramethylbenzidin dissolved in 5 ml acetone and brought up to 50 ml with methanol) and 20 parts of substrate (0.2 M citric acid pH 4.0, 275 ml/l of $H_2O_2$ 30%).

The reaction was stopped with 0.5 M $H_2SO_4$ before the plates were read in a ELISA reader (Titertek Multiskan MCC/340, Flow Laboratories) at 450 nm.

It was found that the vaccination of the chickens with the recombinant viruses R3.2 and R4.1 failed to elicit a humoral antibody response to the coccidia merozoites (average titer 1:100), compared to the control animals (average titer >1:1600) immunized with low doses of sporulated oocysts. This suggests that the positive protection and performance data of the vaccinated chicken (see Table 1 and results discussed above) may result from a cell-mediated effector mechanism.

In order to confirm the presence of specific antibodies against the merozoite 5-7 antigen, blood samples with the highest antibody titer in the ELISA were tested on Western blot, using CV1 cells infected with the rVV 3.2 as antigen source. All sera recognized two proteins of 33 kDa and 23 kDa respectively showing that a succesfull immunization had taken place.

Many modifications and variations of this invention may be made without departing from its spirit and scope, as will become apparent to those skilled in the art. The specific embodiments described herein are offered by way of example only, and the invention is to be limited only by the terms of the appended claims.

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 315 amino acids
      (B) TYPE: amino acid
      (D) TOPOLOGY: linear (ii) MOLECULE TYPE: protein (iii) HYPOTHETICAL: NO (vi) ORIGINAL SOURCE:
      (A) ORGANISM: Eimeria tenella
      (D) DEVELOPMENTAL STAGE: merozoite (xi) SEQUENCE DESCRIPTION: SEQ ID NO:1:

```
Met Ala Lys Ser Met Leu Ser Gly Ile Val Phe Ala Gly Leu Val Ala
 1               5                  10                  15

Ala Ala Ala Ala Ser Ser Ala Asn Ser Ala Ala Asn Val Ser Val Leu
                20                  25                  30

Glu Ser Gly Pro Ala Val Gln Glu Val Pro Ala Arg Thr Val Thr Ala
            35                  40                  45

Arg Leu Ala Lys Pro Leu Leu Leu Leu Ser Ala Leu Ala Ala Thr Leu
        50                  55                  60

Ala Ala Ala Phe Leu Val Leu Gln Cys Phe Asn Ile Ile Ser Ser Asn
65                  70                  75                  80

Asn Gln Gln Thr Ser Val Arg Arg Leu Ala Ala Gly Gly Ala Cys Gly
                85                  90                  95

Asp Glu Glu Asp Ala Asp Glu Gly Thr Ser Gln Gln Ala Ser Arg Arg
               100                 105                 110

Arg Arg Lys Pro Asp Thr Pro Ala Ala Asp Lys Tyr Asp Phe Val Gly
           115                 120                 125
```

-continued

```
Gly Thr Pro Val Ser Val Thr Glu Pro Asn Val Asp Glu Val Leu Ile
            130                 135                 140

Gln Ile Arg Asn Lys Gln Ile Phe Leu Lys Asn Pro Trp Thr Gly Gln
145                 150                 155                 160

Glu Glu Gln Val Leu Val Leu Glu Arg Gln Ser Glu Glu Pro Ile Leu
                165                 170                 175

Ile Val Ala Arg Thr Arg Gln Thr Leu Glu Gly Tyr Leu Gly Ser Gln
            180                 185                 190

Ala Leu Ala Gln Asp Gly Lys Thr Ala Lys Glu Glu Lys Val Glu Gly
            195                 200                 205

Gly Lys Thr His Arg Arg Tyr Lys Val Lys Ser Ser Asp Pro Gly Tyr
        210                 215                 220

Gly Phe Pro Tyr Thr Thr Val Leu Asp Gly Val Pro Val Gly Thr Asp
225                 230                 235                 240

Glu Asp Gly Tyr Val Val Glu Val Leu Met Lys Thr Gly Pro His Gly
                245                 250                 255

Gly Val Asp Met Met Thr Ser Thr Ala Ser Gln Gly Lys Phe Cys Gly
            260                 265                 270

Val Leu Met Asp Asp Gly Lys Gly Asn Leu Val Asp Gly Gln Gly Arg
            275                 280                 285

Lys Ile Thr Ala Val Ile Gly Met Leu Thr Gln Pro Asp Thr Glu Phe
290                 295                 300

Arg Ser Gly Pro Gly Asp Asp Glu Asp Glu
305                 310             315
```

(2) INFORMATION FOR SEQ ID NO:2:

(i) SEQUENCE CHARACTERISTICS:
        (A) LENGTH: 948 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Eimeria tenella (xi) SEQUENCE DESCRIPTION: SEQ ID NO:2:

```
ATGGCTAAGT CTATGCTTTC TGGAATTGTT TTTGCTGGTC TTGTTGCTGC TGCAGCGGCC      60
AGTTCGGCCA ACAGCGCCGC CAACGTCTCC GTTTTGGAGA GTGGGCCCGC TGTGCAGGAA     120
GTGCCAGCGC GCACGGTCAC AGCTCGCCTG GCGAAGCCTT TGCTGCTTCT TTCTGCTCTT     180
GCTGCGACTT TGGCAGCAGC TTTCCTCGTT TTGCAATGCT TCAACATCAT CTCCAGCAAC     240
AACCAGCAAA CCAGCGTCAG GAGACTGGCC GCCGGAGGTG CATGCGGAGA TGAGGAAGAT     300
GCAGATGAGG GAACTTCACA GCAGGCCAGC CGGAGGAGGA GAAAACCTGA TACCCCTGCA     360
GCAGATAAAT ACGATTTTGT TGGCGGAACT CCAGTTTCGG TCACTGAGCC GAATGTTGAT     420
GAAGTCCTTA TCCAAATTAG AAATAAACAA ATCTTTTTGA AGAACCCATG GACTGGACAA     480
GAAGAACAAG TTCTAGTACT GGAACGACAA AGTGAAGAAC CCATTCTGAT TGTGGCGAGG     540
ACAAGACAAA CACTTGAAGG ATATCTTGGT AGTCAAGCTC TTGCACAGGA CGGAAAGACT     600
GCTAAAGAAG AGAAAGTTGA AGGAGGCAAA ACTCACAGAA GATATAAAGT CAAGAGCAGC     660
GACCCAGGAT ATGGATTCCC ATACACCACG GTGCTCGACG GGGTTCCTGT GGGAACAGAC     720
```

-continued

```
GAAGACGGAT ACGTCGTCGA AGTTCTTATG AAAACCGGAC CCCATGGAGG AGTCGACATG      780

ATGACTAGCA CAGCATCACA AGGAAAATTC TGCGGAGTGC TTATGGATGA CGGAAAAGGA      840

AACCTAGTCG ATGGACAAGG GAGAAAAATT ACCGCCGTTA TCGGCATGCT AACTCAACCG      900

GATACCGAGT TTAGAAGCGG ACCAGGAGAC GACGAGGACG ACGAGTGA                  948
```

(2) INFORMATION FOR SEQ ID NO:3:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Eimeria tenella (xi) SEQUENCE DESCRIPTION: SEQ ID NO:3:

```
Ser Asn Asn Gln Gln Thr Ser Val
1               5
```

(2) INFORMATION FOR SEQ ID NO:4:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Eimeria tenella (xi) SEQUENCE DESCRIPTION: SEQ ID NO:4:

```
Cys Gly Asp Glu Glu Asp Ala Asp Glu Gly Thr Ser Gln Gln Ala Ser
1               5                   10                  15
Arg Arg Arg Arg Lys Pro Asp Thr Pro Ala Ala Asp Lys
            20                  25
```

(2) INFORMATION FOR SEQ ID NO:5:

(i) SEQUENCE CHARACTERISTICS:
        (A) LENGTH: 3 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Eimeria tenella (xi) SEQUENCE DESCRIPTION: SEQ ID NO:5:

```
Pro Asn Val
1
```

(2) INFORMATION FOR SEQ ID NO:6:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (iii) HYPOTHETICAL: YES (v) FRAGMENT TYPE: internal (vi) ORIGINAL SOURCE:
            (A) ORGANISM: Eimeria tenella (xi) SEQUENCE DESCRIPTION: SEQ ID NO:6:

Arg Asn Lys Gln Ile Phe
1               5

(2) INFORMATION FOR SEQ ID NO:7:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (iii) HYPOTHETICAL: YES (v) FRAGMENT TYPE: internal (vi) ORIGINAL SOURCE:
            (A) ORGANISM: Eimeria tenella (xi) SEQUENCE DESCRIPTION: SEQ ID NO:7:

Asn Pro Trp Thr Gly Gln Glu Glu
1               5

(2) INFORMATION FOR SEQ ID NO:8:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (iii) HYPOTHETICAL: YES (v) FRAGMENT TYPE: internal (vi) ORIGINAL SOURCE:
            (A) ORGANISM: Eimeria tenella (xi) SEQUENCE DESCRIPTION: SEQ ID NO:8:

Arg Gln Ser Glu Glu
1               5

(2) INFORMATION FOR SEQ ID NO:9:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (iii) HYPOTHETICAL: YES (v) FRAGMENT TYPE: internal (vi) ORIGINAL SOURCE:
            (A) ORGANISM: Eimeria tenella

```
    (xi) SEQUENCE DESCRIPTION: SEQ ID NO:9:

Thr Arg Gln Thr Leu Glu
1               5

(2) INFORMATION FOR SEQ ID NO:10:

(i) SEQUENCE CHARACTERISTICS:
         (A) LENGTH: 30 amino acids
         (B) TYPE: amino acid
         (D) TOPOLOGY: linear (ii) MOLECULE TYPE: peptide (iii) HYPOTHETICAL: YES (v) FRAGMENT TYPE: internal (vi) ORIGINAL SOURCE:
         (A) ORGANISM: Eimeria tenella (xi) SEQUENCE DESCRIPTION: SEQ ID NO:10:

Gln Asp Gly Lys Thr Ala Lys Glu Glu Lys Val Glu Gly Gly Lys Thr
1               5                   10                  15

His Arg Arg Tyr Lys Val Lys Ser Ser Asp Pro Gly Tyr Gly
            20                  25                  30

(2) INFORMATION FOR SEQ ID NO:11:

(i) SEQUENCE CHARACTERISTICS:
         (A) LENGTH: 5 amino acids
         (B) TYPE: amino acid
         (D) TOPOLOGY: linear (ii) MOLECULE TYPE: peptide (iii) HYPOTHETICAL: YES (v) FRAGMENT TYPE: internal (vi) ORIGINAL SOURCE:
         (A) ORGANISM: Eimeria tenella (xi) SEQUENCE DESCRIPTION: SEQ ID NO:11:

Thr Asp Glu Asp Gly
1               5

(2) INFORMATION FOR SEQ ID NO:12:

(i) SEQUENCE CHARACTERISTICS:
         (A) LENGTH: 5 amino acids
         (B) TYPE: amino acid
         (D) TOPOLOGY: linear (ii) MOLECULE TYPE: peptide (iii) HYPOTHETICAL: YES (v) FRAGMENT TYPE: internal (vi) ORIGINAL SOURCE:
         (A) ORGANISM: Eimeria tenella (xi) SEQUENCE DESCRIPTION: SEQ ID NO:12:

Thr Gly Pro His Gly
1               5

(2) INFORMATION FOR SEQ ID NO:13:

(i) SEQUENCE CHARACTERISTICS:
         (A) LENGTH: 5 amino acids
         (B) TYPE: amino acid
```

-continued

```
           (D) TOPOLOGY: linear (ii) MOLECULE TYPE: peptide (iii) HYPOTHETICAL: YES (v) FRAGMENT TYPE: internal (vi) ORIGINAL SOURCE:
           (A) ORGANISM: Eimeria tenella (xi) SEQUENCE DESCRIPTION: SEQ ID NO:13:

Ala Ser Gln Gly Lys
1               5

(2) INFORMATION FOR SEQ ID NO:14:

(i) SEQUENCE CHARACTERISTICS:
           (A) LENGTH: 14 amino acids
           (B) TYPE: amino acid
           (D) TOPOLOGY: linear (ii) MOLECULE TYPE: peptide (iii) HYPOTHETICAL: YES (v) FRAGMENT TYPE: internal (vi) ORIGINAL SOURCE:
           (A) ORGANISM: Eimeria tenella (xi) SEQUENCE DESCRIPTION: SEQ ID NO:14:

Asp Asp Gly Lys Gly Asn Leu Val Asp Gly Gln Gly Arg Lys
1               5                  10

(2) INFORMATION FOR SEQ ID NO:15:

(i) SEQUENCE CHARACTERISTICS:
           (A) LENGTH: 18 amino acids
           (B) TYPE: amino acid
           (D) TOPOLOGY: linear (ii) MOLECULE TYPE: peptide (iii) HYPOTHETICAL: YES (v) FRAGMENT TYPE: C-terminal (vi) ORIGINAL SOURCE:
           (A) ORGANISM: Eimeria tenella (xi) SEQUENCE DESCRIPTION: SEQ ID NO:15:

Thr Gln Pro Asp Thr Glu Phe Arg Ser Gly Pro Gly Asp Asp Glu Asp
1               5                   10                  15
Asp Glu
```

What is claimed is:

1. An isolated DNA molecule encoding an immunogenic polypeptide having an amino acid sequence SEQ ID NO. 1.

2. A recombinant vector comprising a DNA molecule of claim 1 which recombinant vector is capable of directing the expression of said DNA in a compatible host organism.

3. A recombinant vector of claim 2 which is a virus.

4. A recombinant vector of claim 3 which is a poxvirus or herpesvirus.

5. A transformed microorganism containing a recombinant vector of claim 2.

6. An isolated DNA molecule having a nucleotide sequence

```
ATGGCTAAGTCTATGCTTTCTGGAATTGTTTTGCTGGTCTTGTTGCTGCTGCAGCG  (SEQ ID NO:2)
GCCAGTTCGGCCAACAGCGCCGCCAACGTCTCCGTTTTGGAGAGTGGGCCCGCTGTG
CAGGAAGTGCCAGCGCGCACGGTCACAGCTCGCCTGGCGAAGCCTTTGCTGCTTCTT
TCTGCTCTTGCTGCGACTTTGGCAGCAGCTTTCCTCGTTTTGCAATGCTTCAACATC
ATCTCCAGCAACAACCAGCAAACCAGCGTCAGGAGACTGGCCGCCGGALGTGCATGC
GGAGATGAGGAAGATGCAGATGAGGGAACTTCACAGCAGGCCAGCCGGAGGAGGAGA
AAACCTGATACCCCTGCAGCAGATAAATACGATTTTGTTGGCGGAACTCCAGTTTCG
GTCACTGAGCCAATGTTGATGAAGTCCTTATCCAAATTAGAAATAAACAAATCTTT
TTGAAGAACCCATGGACTGGACAAGAAGAACAAGTTCTAGTACTGGAACGACAAAGT
GAAGAACCCATTCTGATTGTGGCGAGGACAAGACAAACACTTGAAGGATATCTTLGT
AGTCAAGCTCTTGCACAGGACGGAAAGACTGCTAAAGAAGAGAAAGTTGAAGGAGGC
AAAACTCACAGAAGATATAAAGTCAAGAGCAGCGACCCAGGATATGGATTCCCATAC
ACCACLGTGCTCGACGGLGTTCCTGTGGGAACAGACGAAGACGGATACGTCGTCGAA
GTTCTTATGAAAACCGGACCCCATGGAGGAGTCGACATGATGACTAGCACAGCATCA
CAAGGAAAATTCTGCGGAGTGCTTATGGATGACGGAAAAGGAAACCTAGTCGATGGA
CAAGGGAGAAAAATTACCGCCGTTATCGGCATGCTAACTCAACCGGATACCGAGTTT
AGAAGCGGACCAGGAGACGACGAGGACGACGAGTGA  (A)
``` encoding an immunogenic polypeptide capable of inducing an immune response against Eimeria parasites.

* * * * *

UNITED STATES PATENT AND TRADEMARK OFFICE
CERTIFICATE OF CORRECTION

PATENT NO.    : 6,008,342
DATED         : December 28, 1999
INVENTOR(S)   : Mary-Helen Binger et al.

It is certified that error appears in the above-identified patent and that said Letters Patent is hereby corrected as shown below:

<u>Title page,</u>
Item [56], References Cited, OTHER PUBLICATIONS, please insert
-- Jenkins et al., FASEB J. 4(2) abstract 3399 (1988) --.

Signed and Sealed this

Eighth Day of April, 2003

JAMES E. ROGAN
*Director of the United States Patent and Trademark Office*